United States Patent
Muzerelle et al.

(10) Patent No.: US 8,741,923 B2
(45) Date of Patent: Jun. 3, 2014

(54) OXADIAZOLE FUSED HETEROCYCLIC DERIVATIVES USEFUL FOR THE TREATMENT OF MULTIPLE SCLEROSIS

(75) Inventors: Mathilde Muzerelle, Gaillard (FR); Anna Quattropani, Geneva (CH); Cyril Montagne, Saint-Genis-Pouilly (FR); Jérôme Dorbais, Annecy (FR)

(73) Assignee: Merck Serono SA, Coinsins, Vaud (CH)

( * ) Notice: Subject to any disclaimer, the term of this patent is extended or adjusted under 35 U.S.C. 154(b) by 189 days.

(21) Appl. No.: 13/130,411

(22) PCT Filed: Dec. 15, 2009

(86) PCT No.: PCT/EP2009/067171
§ 371 (c)(1),
(2), (4) Date: May 20, 2011

(87) PCT Pub. No.: WO2010/069949
PCT Pub. Date: Jun. 24, 2010

(65) Prior Publication Data
US 2011/0230518 A1    Sep. 22, 2011

Related U.S. Application Data

(60) Provisional application No. 61/238,261, filed on Aug. 31, 2009.

(30) Foreign Application Priority Data

Dec. 18, 2008  (EP) .................................... 08172177

(51) Int. Cl.
*A61K 31/4245* (2006.01)
*A61K 31/4725* (2006.01)
*C07D 413/14* (2006.01)
*C07D 413/10* (2006.01)

(52) U.S. Cl.
USPC ........... 514/307; 514/322; 514/323; 514/364; 546/145; 546/148; 546/199; 546/201; 548/131

(58) Field of Classification Search
USPC .......... 514/307, 322, 323, 364; 546/145, 148, 546/199, 201; 548/131
See application file for complete search history.

(56) References Cited

U.S. PATENT DOCUMENTS

| 7,462,629 | B2 * | 12/2008 | Pan et al. ...................... 514/307 |
| 7,678,820 | B2 * | 3/2010 | Harada et al. ................. 514/364 |
| 7,951,825 | B2 * | 5/2011 | Harada et al. ................. 514/340 |
| 8,101,775 | B2 * | 1/2012 | Ahmed et al. ................ 548/131 |
| 8,324,254 | B2 * | 12/2012 | Ahmed et al. ................ 514/338 |

FOREIGN PATENT DOCUMENTS

| EP | 2003132 | 12/2008 |
| WO | WO 2006/047195 | 5/2006 |
| WO | WO 2008/074821 | 6/2008 |
| WO | WO 2008/128951 | 10/2008 |

OTHER PUBLICATIONS

Written Opinion in International Application No. PCT/EP2009/067171, Feb. 23, 2010, pp. 1-6.

* cited by examiner

*Primary Examiner* — Celia Chang
(74) *Attorney, Agent, or Firm* — Saliwanchik, Lloyd & Eisenschenk

(57) ABSTRACT

The invention provides compounds of Formula (I) for the treatment of multiple sclerosis and other diseases.

9 Claims, No Drawings

OXADIAZOLE FUSED HETEROCYCLIC DERIVATIVES USEFUL FOR THE TREATMENT OF MULTIPLE SCLEROSIS

CROSS-REFERENCE TO RELATED APPLICATIONS

This application is the U.S. national stage application of International Patent Application No. PCT/EP2009/067171, filed Dec. 15, 2009, which claims the benefit of U.S. Provisional Patent Application No. 61/238,261, filed Aug. 31, 2009.

The present invention relates to oxadiazoles, their use as medicaments and their use for treating multiple sclerosis and other diseases.

In particular, the invention relates to compounds of formula (I):

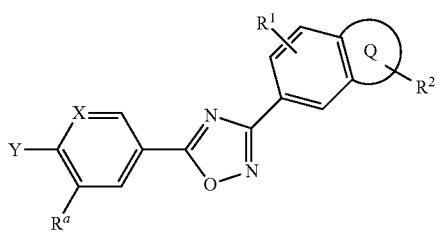

wherein $R^1$, $R^2$ denote independently from one another H, $COOR^3$, $CONHR^3$, Hal, $CF_3$, $OCF_3$, CN, $NO_2$, OH, A, OA, or $(CH_2)_m V(CH_2)_m W$ V denotes O—, —$NR^3$—, —COO— or —$CONR^3$ W denotes $COOR^3$, $SO_2NH_2$, $CON(R^3)_2$ Q denotes a saturated or unsaturated 5 or 6 membered heterocyclic ring containing 1, 2 or 3 N atoms, X denotes —CH— or —N—, Y denotes Het, Ar or Cyc $R^a$ is, A, Hal, $CF_3$, $OR^3$, $OCF_3$, $(CH_2)_n OH$, $(CH_2)_n OA$, $(CH_2)_n OR^3$, CN, $NO_2$, $N(R^3)_2$, $CH_2N(H)_{2-p}(A)_p$, $(CH_2)_n SO_2N(R^3)_2$, $SO_2N(R^3)_2$, $(CH_2)_n NR^3 SO_2A$, $(CH_2)_n SO_2A$, $(CH_2)_n N(SO_2A)_2$, $NR^3CON(R^3)_2$ or $NR^3COA$, $NR^3SO_2N(R^3)_2$, A is a branched or linear alkyl having 1 to 12 C-atoms, wherein one or more, preferably 1 to 7 H-atoms may be replaced by Hal, $OR^3$, CN, $COOR^3$, or $N(R^3)_2$ and wherein one or more, preferably 1 to 7 non-adjacent $CH_2$-groups may be replaced by O, $NR^3$ or S and/or by —CH=CH— or —C≡C— groups, or denotes cycloalkyl or cycloalkylalkylen having 3-7 ring C atoms Ar denotes a monocyclic or bicyclic, unsaturated or aromatic carbocyclic ring having 6 to 14 carbon atoms, which is monosubstituted, disubstituted or trisubstituted by A, $OR^3$, $N(R^3)_2$, $NO_2$, CN, $COOR^3$, $CF_3$, $OCF_3$, $CON(R^3)_2$, $NR^3COA$, $NR^3CON(R^3)_2$, $NR^3SO_2A$, $COR^3$, $SO_2N(R^3)_2$, SOA or $SO_2A$, Or, when $R^a$ is Hal, $OR^3$, $OCF_3$, $(CH_2)_n OH$, $(CH_2)_n OA$, $(CH_2)_n OR^3$, CN, $NO_2$, $N(R^3)_2$, $CH_2N(H)_{2-p}(A)_p$ $(CH_2)_n SO_2N(R^3)_2$, $SO_2N(R^3)_2$, $(CH_2)_n NR^3 SO_2A$, $(CH_2)_n SO_2A$, $(CH_2)_n N(SO_2A)_2$, $NR^3CON(R^3)_2$ or $NR^3COA$, $NR^3SO_2N(R^3)_2$, Ar can also be substituted by Hal, such that at least one atom adjacent to the atom linking the group Ar to the rest of the molecule bears one of said substituents.

Het denotes a monocyclic or bicyclic, saturated, unsaturated or aromatic heterocyclic ring having 1 to 4 N, O and/or S atoms which is monosubstituted, disubstituted or trisubstituted by Hal, A, —$[C(R^3)_2]_n$—Ar, —$[C(R^3)_2]_n$-cycloalkyl, $OR^3$, $CF_3$, $OCF_3$, $N(R^3)_2$, $NR^3CON(R^3)_2$, $NO_2$, CN, —$[C(R^3)_2]_n$—$COOR^3$, —$[C(R^3)_2]_n$—$CON(R^3)_2$, $NR^3COA$, $NR^3SO_2A$, $COR^3$, $SO_2N(R^3)_2$, SOA, and/or $SO_2A$, such that at least one atom adjacent to the atom linking the group Het to the rest of the molecule bears one of said substituents.

Cyc denotes a saturated or unsaturated carbocyclic ring containing 3 to 7 carbon atoms which is substituted by Hal, A, —$[C(R^3)_2]_n$—Ar, —$[C(R^3)_2]_n$-cycloalkyl, $OR^3$, $CF_3$, $OCF_3$, $N(R^3)_2$, $NR^3CON(R^3)_2$, $NO_2$, CN, —$[C(R^3)_2]_n$—$COOR^3$, —$[C(R^3)_2]_n$—$CON(R^3)_2$, $NR^3COA$, $NR^3SO_2A$, $COR^3$, $SO_2N(R^3)_2$, SOA, and/or $SO_2A$, such that at least one atom adjacent to the atom linking the group Cyc to the rest of the molecule bears one of said substituents.

Hal is F, Cl, Br or I, $R^3$ is H or A p is 0, 1 or 2 n is 0, 1, 2, 3 or 4 m is 0, 1, 2, 3 or 4 and pharmaceutically acceptable derivatives, solvates, tautomers, salts and stereoisomers thereof, including mixtures thereof in all ratios.

The compounds of formula (I) and related formulae are preferably binding on receptors for sphingosine 1-phosphate ($S_1P$). $S_1P$ is a bioactive sphingolipid metabolite that is secreted by hematopoietic cells and stored and released from activated platelets. It acts as an agonist on a family of G protein-coupled receptors (GPCR). Five sphingosine 1-phosphate receptors have been identified ($S_1P_1$, $S_1P_2$, $S_1P_3$, $S_1P_4$, and $S_1P_5$, also known as endothelial differentiation genes, which are Edg1, Edg5, Edg3, Edg6 and Edg8 respectively), that have widespread cellular and tissue distribution and are well conserved in human and rodent species.

$S_1P$ is involved in a number of cellular functions such as survival, proliferation and immunological responses. The compounds of the present invention are preferably acting as $S_1P_1$/Edg1 receptor agonists and thus have immunosuppressive activities by modulating leukocyte trafficking, sequestering lymphocytes in secondary lymphoid tissues, and interfering with cell-cell interactions required for an efficient immune response. The invention is also directed to pharmaceutical compositions containing such compounds and methods of treatment or prevention.

FTY720 or fingolimod, a non selective $S_1P_1$ agonist, exerts immunosuppressive activity and shows therapeutic effects in the treatment of relapsing-remitting multiple sclerosis. Numerous publications have been already published using this compound: Cyster J G Annu Rev Immunol 23:127-59, 2005, Rosen H Nat Rev Immunol 5:560-570, 2005, Rosen H Trends Immunol 28:102-107, 2007, Yopp A C Clin Transplant 20:788-795, 2006, Kappos L N Engl J Med 355:1124-1140, 2006, Massberg S N Engl J Med 355:1088-1089, 2006.

Immunosuppressive agents are further useful in a wide variety of autoimmune and chronic inflammatory diseases, including systemic lupus erythematosus, chronic rheumatoid arthritis, type I diabetes mellitus, inflammatory bowel diseases, biliary cirrhosis, uveitis and other disorders such as Crohn's diseases, ulcerative colitis, bullous pemphigoid, sarcoidosis, psoriasis, autoimmune myositis, Wegener's granulomatosis, ichthyosis, Graves ophthalmopathy, atopic dermatitis and asthma. They are also useful as part of chemotherapeutic regimens for the treatment of cancers, lymphomas and leukemias.

It has been found that the compounds of the present invention are selective S1P1 agonists with improved pharmacological and/or other properties.

Thus, the present invention preferably comprises compounds which are agonists of the S1P1/Edg1 receptor, especially having selectivity over the S1P3/Edg3 receptor. An S1P1/Edg1 receptor selective agonist has advantages over current therapies and extends the therapeutic window of lymphocyte sequestration agents, allowing better tolerability with higher dosing and thus improving efficacy.

The invention further relates to the manufacture of a medicament for the improvement of vascular function, either alone or in combination with other active compounds or therapies.

The inventions further relates to the use of compounds according to formula (I) in combination with immunomodulating agents for example Fingolimod; cyclosporins, rapamycins or ascomycins, or their immunosuppressive analogs, e.g. cyclosporin A, cyclosporin G, FK-506, ABT-281, ASM981, rapamycin, 40-O-(2-hydroxy)ethyl-rapamycin etc.; corticosteroids; cyclophosphamide; azathioprene; methotrexate; leflunomide; mizoribine; mycophenolic add; mycophenolate mofetil; 15-deoxyspergualine; diflucortolone valerate; difluprednate; Alclometasone dipropionate; amcinonide; amsacrine; asparaginase; azathioprine; basiliximab; beclometasone dipropionate; betamethasone; betamethasone acetate; betamethasone dipropionate; betamethasone phosphate sodique; betamethasone valerate; budesonide; captopril; chlormethine chlorhydrate; cladribine; clobetasol propionate; cortisone acetate; cortivazol; cyclophosphamide; cytarabine; daclizumab; dactinomycine; desonide; desoximetasone; dexamethasone; dexamethasone acetate; dexamethasone isonicotinate; dexamethasone metasulfobenzoate sodique; dexamethasone phosphate; dexamethasone tebutate; dichlorisone acetate; doxorubicine chlorhydrate; epirubicine chlorhydrate; fluclorolone acetonide; fludrocortisone acetate; fludroxycortide; flumetasone pivalate; flunisolide; fluocinolone acetonide; fluocinonide; fluocortolone; fluocortolone hexanoate; fluocortolone pivalate; fluorometholone; fluprednidene acetate; fluticasone propionate; gemcitabine chlorhydrate; halcinonide; hydrocortisone, hydrocortisone acetate, hydrocortisone butyrate, hydrocortisone hemisuccinate; melphalan; meprednisone; mercaptopurine; methylprednisolone; methylprednisolone acetate; methylprednisolone hemisuccinate; misoprostol; muromonabcd3; mycophenolate mofetil; paramethasone acetate; prednazoline, prednisolone; prednisolone acetate; prednisolone caproate; prednisolone metasulfobenzoate sodique; prednisolone phosphate sodique; prednisone; prednylidene; rifampicine; rifampicine sodique; tacrolimus; thalidomide; thiotepa; tixocortol pivalate; triamcinolone; triamcinolone acetonide hemisuccinate; triamcinolone benetonide; triamcinolone diacetate; triamcinolone hexacetonide; immunosuppressive monoclonal antibodies, e.g., monoclonal antibodies to leukocyte receptors, e.g., MHC, CD2, CD3, CD4, CD7, CD25, CD28, B7, CD40, CD45 or CD58 or their ligands; or other immunomodulatory compounds, e.g. CTLA41g, or other adhesion molecule inhibitors, e.g. mAbs or low molecular weight inhibitors including Selectin antagonists and VLA-4 antagonists. A preferred composition is with Cyclosporin A, FK506, rapamycin or 40-(2-hydroxy)ethyl-rapamycin and Fingolimod.

The invention further relates to a kit or a set comprising at least one compound of Formula (I), preferably in combination with immunomodulating agents. Alternatively, the kit consists of separate packs of:

(a) an effective amount of a compound of the formula (I) and/or pharmaceutically usable derivatives, solvates and stereoisomers thereof, including mixtures thereof in all ratios, and (b) an effective amount of a further medicament active ingredient.

The compounds according to formula (I) and related formulae may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

The compounds of invention have been named according to the standards used in the program "ACD/Name Batch" from Advanced Chemistry Development Inc., ACD/Labs (7.00 Release). Product version: 7.10, build: 15 Sep. 2003.

Depending on the nature of X, $R^a$, $R^b$, $R^1$ and $R^2$, different synthetic strategies may be selected for the synthesis of compounds of formula (I) and related formulae. In the process illustrated in the following schemes, $R^a$, $R^b$, $R^1$ and $R^2$ are as above defined in the description. Compounds of formula (I), wherein X is defined as O or S, can be obtained analogously.

In general, the fused heterocyclic compounds according to formula (I) and related formulae of this invention may be prepared from readily available starting materials. If such starting materials are not commercially available they may be prepared by standard synthetic techniques. The following general methods and procedures described hereinafter in the examples may be employed to prepare compounds of formula (I) and related formulae.

The process for the preparation of compounds of formula (I) and related formulae, wherein X, $R^a$, $R^b$, $R^1$ and $R^2$ are defined as above, and as outlined in Schemes 1 to 14, is also object of the invention.

The following abbreviations refer respectively to the definitions below:

Ac (acetyl), ACN (acetonitrile), AcOH (Acetic acid), AIBN (azobisisobutyronitrile), Boc (tert-butoxycarbonyl), bs (broad singlet), Bu (butyl), cHex (cyclohexane), d (doublet), dba (dibenzylideneacetone), DCM (dichloromethane), DIEA (diisopropylethylamine), DMAP (1. 4-Dimethylaminopyridine), DMF (dimethylformamide), DMSO (dimethylsulfoxide), dppf (1. 1,1'-Bis(diphenylphosphino)ferrocene), EDC (1. 1-ethyl-3-(3-dimethylaminopropyl) carbodiimide), ESI (electro-spray ionization), Et (ethyl), g (gram), h (hour), HATU (O-(7-azabenzotriazol-1-yl)-N,N,N',N'-tetramethyluronium hexafluorophosphate), HPLC (high performance liquid chromatography), Hz (Hertz), iPr (isopropyl), L (liter), LC (liquid chromatography), LG (leaving group), m (meter), M (molar), m (multiplet), Me (methyl), mg (milligram), MHz (megaherz), min (minute), mL (milliliter), 4 (microliter), mm (millimeter), μm (micrometer), mmol (millimole), MS (mass spectrometry), Ms (mesyl), NBS (N-bromosuccinimide), NMM (1. N-methylmorpholine), NMP (1. N-methylpyrrolidone), NMR (nuclear magnetic resonance), Pd/C (palladium on charcoal), PG (protecting group), Ph (phenyl), Pt/C (platinum on charcoal), Py (pyridine), Rt (retention time), RT (room temperature), s (singlet), SPE (solid phase extraction), TBTU (1. O-(Benzotriazol-1-yl)-N,N,N',N'-tetramethyluronium tetrafluoroborate), tBu (tert-butyl), TEA (triethylamine), TFA (trifluoroacetic acid), THF (tetrahydrofuran), HPLC (ultra performance liquid chromatography), UV (ultraviolet), Compounds of formula (I) can be synthesized either from the deprotection of compounds of formula (Ia) and (Ic) to give compounds of formula (Ib) and (Id) respectively or by formation of the oxadiazole ring. Generally, compounds of formula (Ib), wherein $R^1$, $R^a$, X, Y, Q and A are defined as above, can be prepared by hydrolysis of the ester of formula (Ia), wherein $R^1$, $R^a$, X, Y, Q and A are as above defined and $R^3$ is more preferably a methyl or tert-butyl group. Hydrolysis and saponification can be performed by using conditions well known to those skilled in the art, such as a metal hydroxide, e.g. lithium hydroxide, sodium hydroxide or potassium hydroxide, in a suitable solvent such as THF, methanol, ethanol or water or mixtures thereof. The reaction can also be performed using an acid, e.g. HCl or TFA, in a suitable solvent such as DCM or a ether such as dioxane or Et$_2$O, at a temperature between about 20° C. to about 100° C., preferably at RT, for a few hours, e.g. one hour to 24 h (Scheme 1).

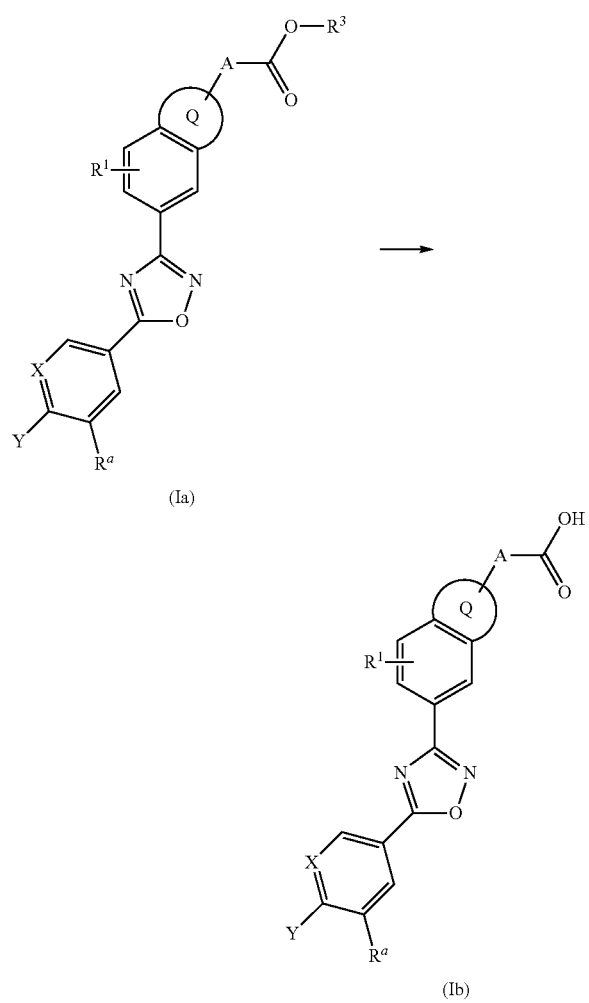

Alternatively, compounds of formula (Id), wherein $R^1$, $R^2$, $R^a$, X, Y and Q are defined as above, may be obtained by the deprotection of the amine compound of formula (Ic) as shown in Scheme 2 wherein X, Y, $R^1$, $R^2$ and Q are as above defined and wherein $R^3$ is an alkyl group. More preferably $R^3$ is a methyl, ethyl or tertiobutyl group. Conditions well known to those skilled in the art can be used. For example, an acidic cleavage using TFA or HCl in a suitable solvent such as DCM, Dioxane, Et$_2$O or mixtures thereof can be performed. The transformation of (Ic) to (Id) can be done at a temperature between about 10° C. to about 100° C. Preferably, the temperature is between about 20° C. and about 50° C., or RT, and the reaction is performed during a few hours, e.g. one hour to 24 h (Scheme 2).

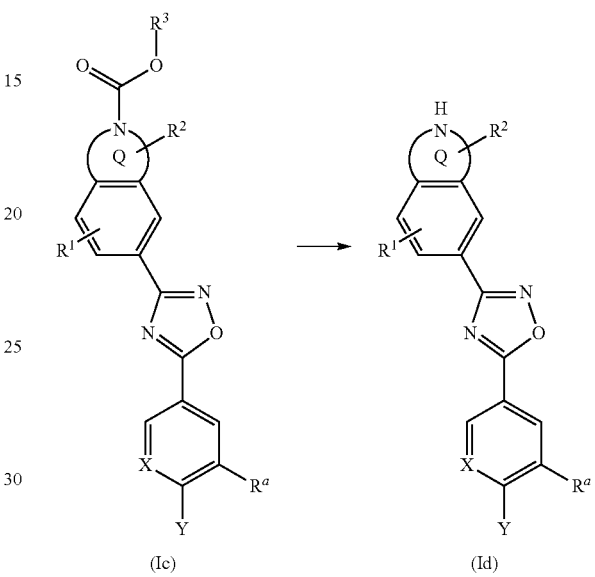

The compounds of formula (I), wherein $R^1$, $R^2$, $R^a$, X, Q, and Y are defined as above, can be obtained in a 2-step protocol as outlined in Scheme 3. The first step consists in the coupling of a carboxylic acid of formula (III) wherein X, Y and $R^a$ are as above defined, with an amidoxime of formula (II), wherein $R^1$, $R^2$, and Q are defined as above. General protocols for such coupling are given below in the examples, using conditions and methods well known to those skilled in the art. Standard coupling agents, such as but not limited to EDC, HATU, TBTU can be used, in the presence or absence of bases such as TEA, DIEA, NMM in a suitable solvent such as DCM, ACN, THF or DMF, at a temperature rising from about 0° C. to about 50° C., preferably at RT, for a few hours, e.g. one hour to 24 h.

Alternatively, a carboxylic acid derivative (e.g. acyl chloride IIIa) may be coupled with the amidoxime (II), using conditions and methods well known to those skilled in the art, in the presence of bases such as TEA, DIEA, NMM in a suitable solvent such as DCM, THF or DMF, at a temperature rising from about 0° C. to about 50° C., preferably at RT, for a few hours, e.g. one hour to 24 h (Scheme 4). The second step consists on the cyclization and dehydration of the O-substituted amidoximes (IV) to form oxadiazole (I). Conditions are given below in the examples, using methods well known to those skilled in the art to prepare oxadiazole, such as cyclodehydration at temperature rising from RT to about 150° C., typically 150° C., using possibly a microwave oven, for a time comprised between 15 minutes and 24 hours, preferably for 30 min, in a suitable solvent or mixture of solvents such as ACN, THF, Pyridine, DMF, toluene in the presence or absence of a base such as DIEA, TEA, or tetrabutyl ammonium fluoride.

Scheme 3

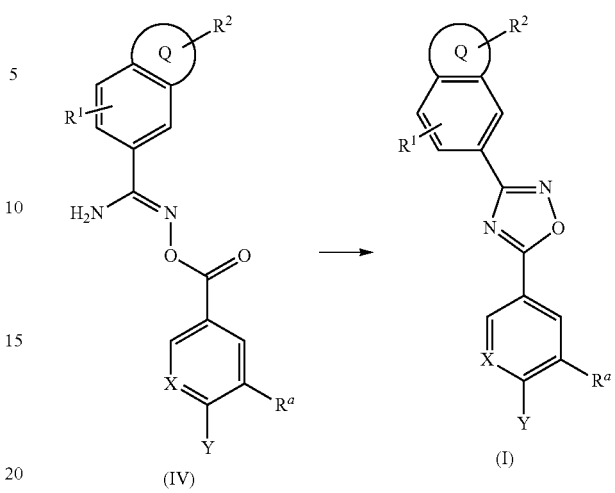

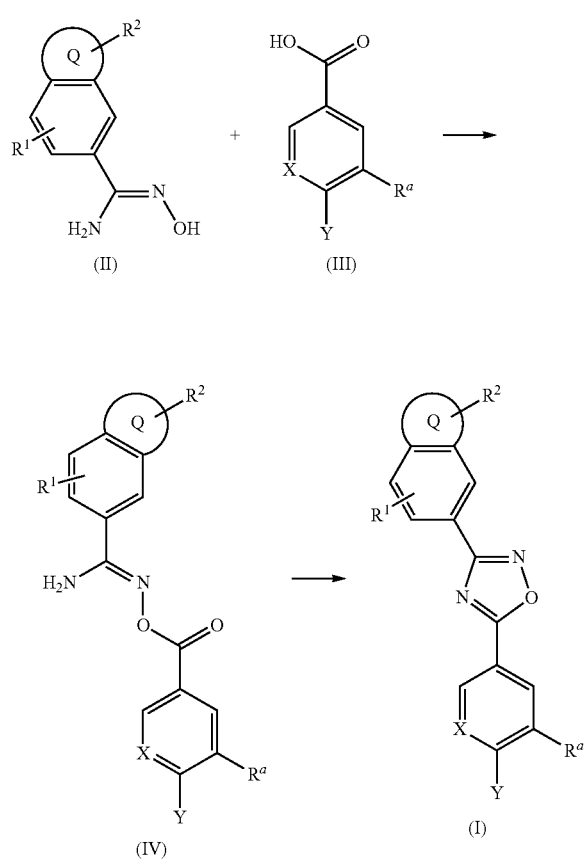

Scheme 4

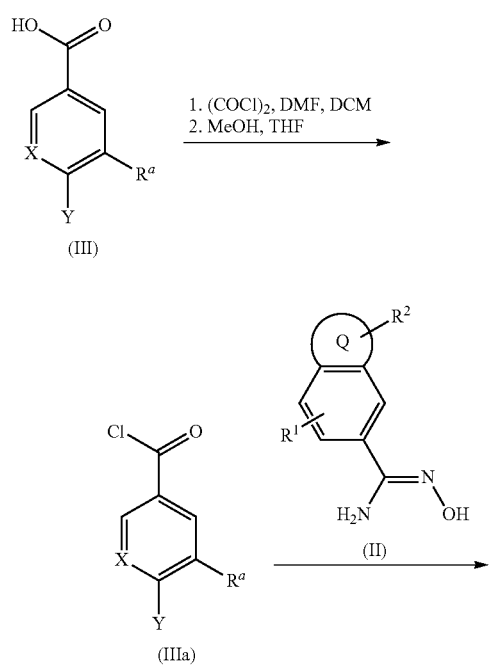

The method for preparing the compounds of formula (I) selected below:

5-{5-[4-(2-methylpiperidin-1-yl)-3-(trifluoromethyl)phenyl]-1,2,4-oxadiazol-3-yl}-1H-benzimidazole 5-[3-(1H-benzimidazol-5-yl)-1,2,4-oxadiazol-5-yl]-2-(2-methylpiperidin-1-yl)benzonitrile 5-{5-[5-methyl-6-(2-methylpiperidin-1-yl)pyridin-3-yl]-1,2,4-oxadiazol-3-yl}-1H-benzimidazole 5-{5-[2-(methoxymethyl)-2'-methylbiphenyl-4-yl]-1,2,4-oxadiazol-3-yl}-1H-benzimidazole 1-{4-[3-(1H-benzimidazol-6-yl)-1,2,4-oxadiazol-5-yl]-2'-methylbiphenyl-2-yl}-N,N-dimethylmethanamine 5-{5-[3-(methoxymethyl)-4-(2-methylpiperidin-1-yl)phenyl]-1,2,4-oxadiazol-3-yl}-1H-benzimidazole 7-fluoro-5-{5-[4-(2-methylpiperidin-1-yl)-3-(trifluoromethyl)phenyl]-1,2,4-oxadiazol-3-yl}-1H-benzimidazole 7-methyl-5-{5-[4-(2-methylpiperidin-1-yl)-3-(trifluoromethyl)phenyl]-1,2,4-oxadiazol-3-yl}-1H-benzimidazole 7-fluoro-5-{5-[2-(methoxymethyl)-2'-methylbiphenyl-4-yl]-1,2,4-oxadiazol-3-yl}-1H-benzimidazole 6-{5-[4-(2-methylpiperidin-1-yl)-3-(trifluoromethyl)phenyl]-1,2,4-oxadiazol-3-yl}-1,2,3,4-tetrahydroisoquinoline N-{2-(2-methylpiperidin-1-yl)-5-[3-(1,2,3,4-tetrahydroisoquinolin-7-yl)-1,2,4-oxadiazol-5-yl]phenyl}methanesulfonamide 2-(2-methylpiperidin-1-yl)-5-[3-(1,2,3,4-tetrahydroisoquinolin-7-yl)-1,2,4-oxadiazol-5-yl]benzonitrile tert-butyl 7-{5-[5-methyl-6-(2-methylpyrrolidin-1-yl)pyridin-3-yl]-1,2,4-oxadiazol-3-yl}-3,4-dihydroisoquinoline-2(1H)-carboxylate 7-{5-[5-methyl-6-(2-methylpyrrolidin-1-yl)pyridin-3-yl]-1,2,4-oxadiazol-3-yl}-1,2,3,4-tetrahydroisoquinoline 7-{5-[2-(methoxymethyl)-2'-methylbiphenyl-4-yl]-1,2,4-oxadiazol-3-yl}-1,2,3,4-tetrahydroisoquinoline

[7-{5-[2-(methoxymethyl)-2'-methylbiphenyl-4-yl]-1,2,4-oxadiazol-3-yl}-3,4-dihydroisoquinolin-2(1H)-yl]acetic acid 5-[5-(2,2'-dimethylbiphenyl-4-yl)-1,2,4-oxadiazol-3-yl]-1-methyl-1H-indole {5-[5-(2,2'-dimethylbiphenyl-4-yl)-1,2,4-oxadiazol-3-yl]-1H-indol-1-yl}acetic acid 1-methyl-5-{5-[4-(2-methylpiperidin-1-yl)-3-nitrophenyl]-1,2,4-oxadiazol-3-yl}-1H-indole ethyl 6-methoxy-5-{5-[4-(2-methylpiperidin-1-yl)-3-(trifluoromethyl)phenyl]-1,2,4-oxadiazol-3-yl}-1H-indole-2-carboxylate 6-methoxy-5-{5-[4-(2-methylpiperidin-1-yl)-3-(trifluoromethyl)phenyl]-1,2,4-oxadiazol-3-yl}-1H-indole-2-carboxylic acid N-[5-[3-(1H-indol-5-yl)-1,2,4-oxadiazol-5-yl]-2-(2-methylpiperidin-1-yl)phenyl]methanesulfonamide 5-[3-(1H-indol-5-yl)-1,2,4-oxadiazol-5-yl]-2-(2-methylpiperidin-1-yl)benzonitrile 5-{5-[3-methoxy-4-(4-methyl-3-thienyl)phenyl]-1,2,4-oxadiazol-3-yl}-1H-indazole 5-[5-(2,2'-dimethylbiphenyl-4-yl)-1,2,4-oxadiazol-3-yl]-1H-indazole 5-{5-[2-(methoxymethyl)-2'-methylbiphenyl-4-yl]-1,2,4-oxadiazol-3-yl}-7-methyl-1H-benzimidazole 5-{5-[4-(2-ethylpiperidin-1-yl)-3-(methoxymethyl)phenyl]-1,2,4-oxadiazol-3-yl}-1H-benzimidazole 5-{5-[4-[(2R)-2-methylpiperidin-1-yl]-3-(trifluoromethyl)phenyl]-1,2,4-oxadiazol-3-yl}-1H-benzimidazole 5-{5-[4-[(2S)-2-methylpiperidin-1-yl]-3-(trifluoromethyl)phenyl]-1,2,4-oxadiazol-3-yl}-1H-benzimidazole

[7-{5-[2'-ethyl-2-(methoxymethyl)biphenyl-4-yl]-1,2,4-oxadiazol-3-yl}-3,4-dihydroisoquinolin-2(1H)-yl]acetic acid 3-[7-{5-[2'-ethyl-2-(methoxymethyl)biphenyl-4-yl]-1,2,4-oxadiazol-3-yl}-3,4-dihydroisoquinolin-2(1H)-yl]propanoic acid 6-{5-[2-(methoxymethyl)-2'-methylbiphenyl-4-yl]-1,2,4-oxadiazol-3-yl}-1H-indole-2-carboxylic acid 3-[7-{5-[4-(2-ethylpiperidin-1-yl)-3-(methoxymethyl)phenyl]-1,2,4-oxadiazol-3-yl}-3,4-dihydroisoquinolin-2(1H)-yl]propanoic acid

[7-{5-[4-(2-ethylpiperidin-1-yl)-3-(methoxymethyl)phenyl]-1,2,4-oxadiazol-3-yl}-3,4-dihydroisoquinolin-2(1H)-yl]acetic acid 3-[7-{5-[2-(methoxymethyl)-2'-methylbiphenyl-4-yl]-1,2,4-oxadiazol-3-yl}-3,4-dihydroisoquinolin-2(1H)-yl]propanoic acid

[7-{5-[2'-methyl-2-(trifluoromethyl)biphenyl-4-yl]-1,2,4-oxadiazol-3-yl}-3,4-dihydroisoquinolin-2(1H)-yl]acetic acid 3-[7-{5-[4-(2-methylpiperidin-1-yl)-3-(trifluoromethyl)phenyl]-1,2,4-oxadiazol-3-yl}-3,4-dihydroisoquinolin-2(1H)-yl]propanoic acid

[7-{5-[4-(2-methylpiperidin-1-yl)-3-(trifluoromethyl)phenyl]-1,2,4-oxadiazol-3-yl}-3,4-dihydroisoquinolin-2(1H)-yl]acetic acid 3-[7-{5-[2'-methyl-2-(trifluoromethyl)biphenyl-4-yl]-1,2,4-oxadiazol-3-yl}-3,4-dihydroisoquinolin-2(1H)-yl]propanoic acid 3-{6-[5-(2-Methoxymethyl-2'-methyl-biphenyl-4-yl)-[1,2,4]oxadiazol-3-yl]-3,4-dihydro-1H-isoquinolin-2-yl}-propionic acid is more particularly described in the examples.

Compounds of formula (III), wherein $R^a$, Y and X are defined as above, are either commercially available or may be prepared by standard synthetic techniques, as hereinafter described in the examples, for example by metal catalyzed coupling reaction or aromatic nucleophilic substitution on the corresponding halogenated benzoic acid, alkyl benzoate. Alternatively, compounds of formula (III), wherein $R^a$, Y and X are defined as above, may be obtained by metal catalyzed cross-coupling reaction followed by hydrolysis of the resulting ester (VIII), as shown in Scheme 5 below. More particularly, they may be obtained by Suzuki-Miyaura coupling reaction between a compound of Formula (VI), wherein X, $R^a$ and $R^3$ are as above defined and wherein $R^c$ is a leaving group, and a boronic acid (VII) wherein Y is as above defined, or ester derivative as shown in Scheme 5 (Miyaura, N.; Suzuki, A. *Chem. Rev.* 1995, 95, 2457; Takahiro I. and Toshiaki M., *Tetrahedron Lett.* 2005, 46, 3573-3577). Preferably $R^c$ may be Br, I or a sulfonate ester such as triflate. In a typical procedure, compounds of Formula (VI) and boronic acid (VII) or ester are heated at various temperatures, e.g. at temperatures from 20° C. to 200° C., by traditional thermic methods or using microwave technology in the presence of a base such as but not limited to a carbonate salt, e.g. $K_2CO_3$, $Na_2CO_3$, $Cs_2CO_3$, and a catalytic amount of palladium catalyst such as $Pd(PPh_3)_4$, $PdCl_2(PPh_3)_2$, $Pd(OAc)_2$, with the possible addition of phosphine ligands such as $PPh_3$, S-Phos, X-Phos in an appropriate solvent or mixture of solvents such as THF, Toluene, Dioxane, MeOH, ACN, DMF, water. All the different combinations described above may be used. The resulting ester (VIII) can then be hydrolyzed using conditions well known to those skilled in the art, such as but not limited to the use of a metal hydroxide, e.g. lithium hydroxide, sodium hydroxide or potassium hydroxide, in a suitable solvent such as THF, methanol, ethanol or water or mixtures thereof, at a temperature rising from about 20° C. to about 60° C., preferably at RT, for a few hours, e.g. one hour to 24 h, to give compounds of formula (III).

Scheme 5

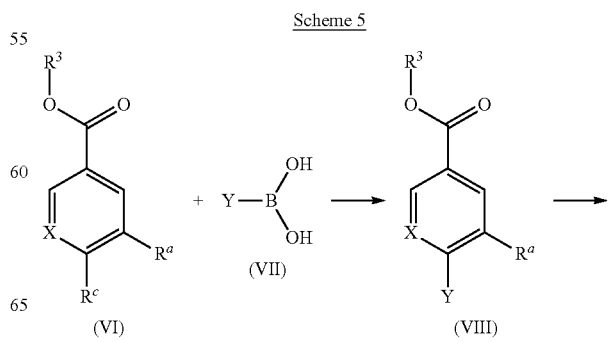

-continued

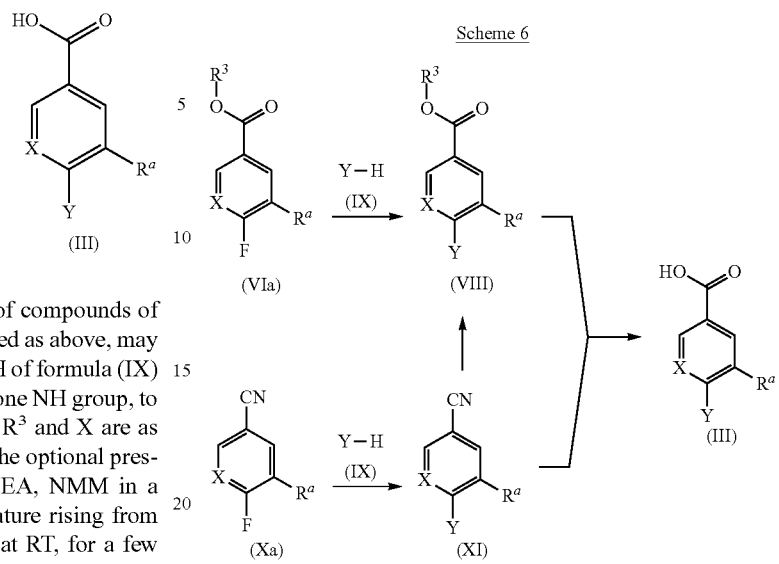

An alternative route for the preparation of compounds of formula (III), wherein $R^a$, Y and X are defined as above, may be the addition of an amino compound Y—H of formula (IX) wherein Y is Het or Cyc containing at least one NH group, to a compound of formula (VIa) wherein $R^a$, $R^3$ and X are as above defined, as outlined in Scheme 6, in the optional presence of a suitable base, such as TEA, DIEA, NMM in a solvent such as THF or DMF, at a temperature rising from about 20° C. to about 100° C., preferably at RT, for a few hours, e.g. one hour to 24 h. An amino compound Y—H of formula (IX) wherein Y is Het or Cyc containing at least one NH group, can be also used neat, as solvent. Ester of formula (VIII) can be hydrolyzed into compounds of formula (III) under conditions described above and in the examples below. Alternatively, an amino compound of formula (IX) wherein Y is Het or Cyc containing at least one NH group, can be added to a compound of formula (Xa) under similar conditions as the one described above and in the examples below. The resulting compound of formula (XI) can be hydrolyzed into the corresponding acid (III), using conditions well known to those skilled in the art, such as but not limited to the use of a base, e.g. NaOH, KOH in a suitable solvent such as but not limited to methanol or water or mixtures thereof, at a temperature rising from about 20° C. to about 100° C., preferably at 78° C., for 5 h to 24 h. Alternatively, a compound of formula (XI) can be transformed into the corresponding ester (VIII), using conditions well known to those skilled in the art, such as but not limited to the use of an acid, e.g. HCl, $H_2SO_4$ in a suitable solvent such as but not limited to methanol or ethanol or mixtures thereof, at a temperature rising from about 20° C. to about 100° C., preferably at 80° C., for 1 h to 48 h.

Aromatic heterocycles are preferably involved in the pathway described in scheme 5. Non-aromatic amines are preferably involved in the pathway described in scheme 6.

Compounds of formula (VIa) to (VIi) are either commercially available or may be prepared by standard synthetic techniques, as hereinafter described in the examples. Typically, when $R^c$ is F, Cl, Br, I or a sulfonate ester such as triflate and $R^3$ is as defined above, compounds of formula (VId), (VIf) and (VIh) may be prepared by bromination of the corresponding toluoyl derivative (VIb) followed by an $S_N2$ reaction on the bromine derivative (VIc) with a suitable group, such as but not exclusively an acetate salt, e.g. NaOAc in HOAc, an alcoholate salt, e.g. NaOA in the corresponding alcohol, THF or DMF, an alcohol, e.g. HOA, that can be used as solvent, an amine, e.g. $HN(R^3)_2$ or a thiolate salt, e.g. NaSA, in a suitable solvent, such as but not exclusively THF, MeCN, DMF, at a temperature ranging from RT to 130° C., with the possible use of the microwave (see Scheme 7). Hydrolysis of the acetate group on compounds of formula (VId), using conditions well known to those skilled in the art, such as but not limited to sodium hydroxide in EtOH at 60° C., afforded compounds of formula (VIe). Compounds of formula (VIe), can be further transformed into the corresponding alkyl sulfonate (VIg) that can be used as starting material for $S_N2$ reactions similarly to (VIc), as it is illustrated on Scheme 7.

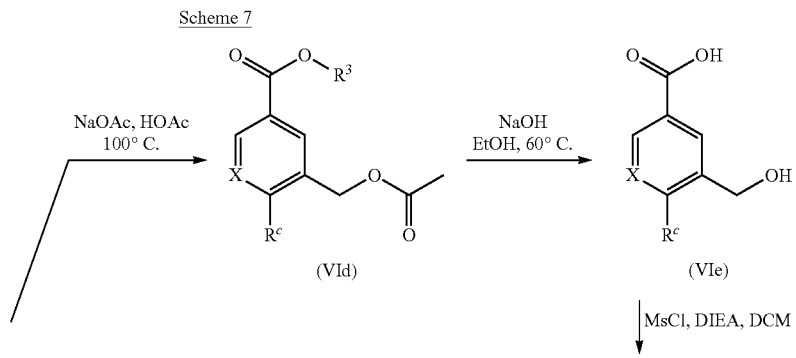

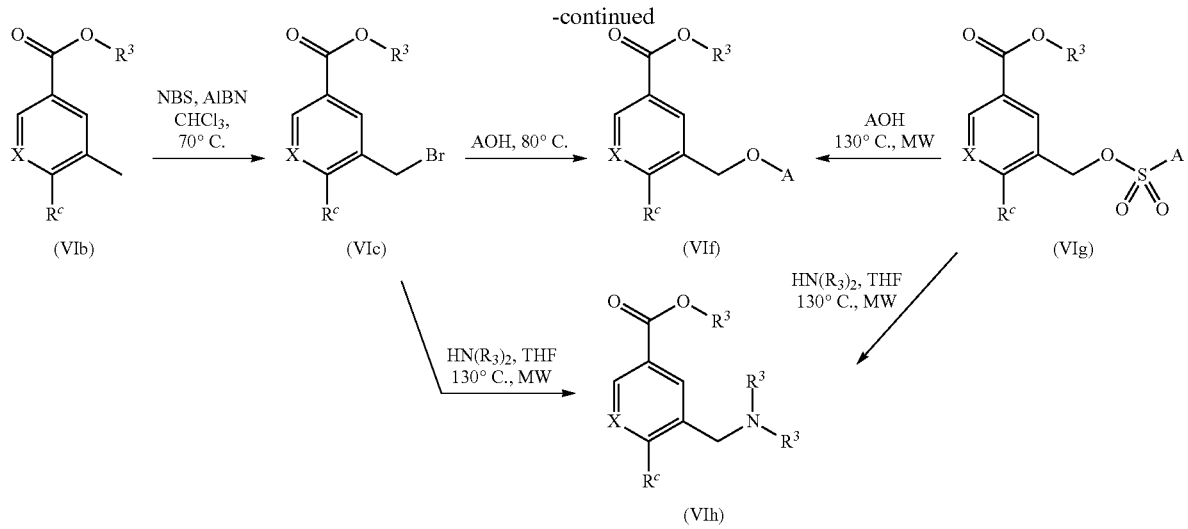

Alternatively, compounds of formula (VIe) can be prepared by reduction of the aldehyde of formula (VIi), with a suitable reducing agent, such as but not limited to NaBH$_4$ at a temperature rising from about 0° C. to about 50° C., preferably at RT, for 1 h to 24 h. Transformation of compounds of formula (VIi) by metal catalyzed cross coupling reaction or S$_N$Ar reaction can be performed first to give compounds of the formula (VIIIa). Then the reduction of compounds of the formula (VIIIa) by a suitable reducing agent, such as but not limited to NaBH$_4$ gives the corresponding alcohol of formula (VIIIb), as outlined in Scheme 8.

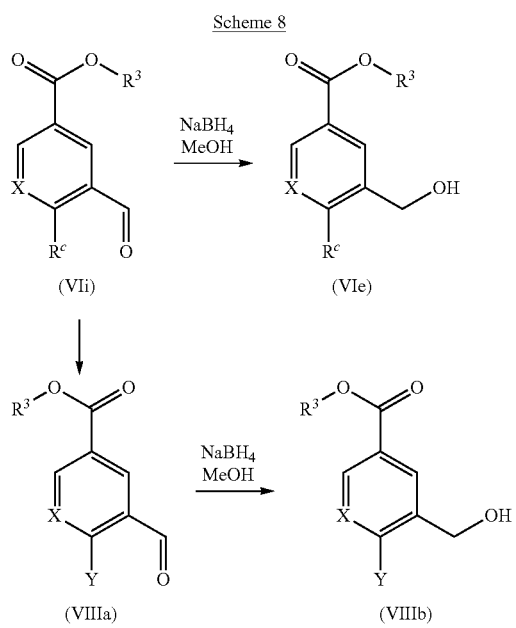

Compounds of Formula (VIIIe) wherein R$^a$ is (CH$_2$)$_n$ NR$^3$SO$_2$A, wherein n=0 and A is as defined above, and R$^3$, Y, and X are defined as above, can be synthesized from compounds of formula (VIIIc), as it is outlined in Scheme 9. After reduction of the nitro group, the resulting amine (VIIId) can be transformed into a sulphonamide (VIIIe) with ASO$_2$Cl addition, wherein A is as defined above, in the presence of a base, such as but not limited to TEA, DIEA, NMM, pyridine, in a solvent or a mixture of solvents such as DCM, DMF, Pyridine at a temperature rising from about 20° C. to about 100° C., preferably at 50° C., for 1 h to 48 h.

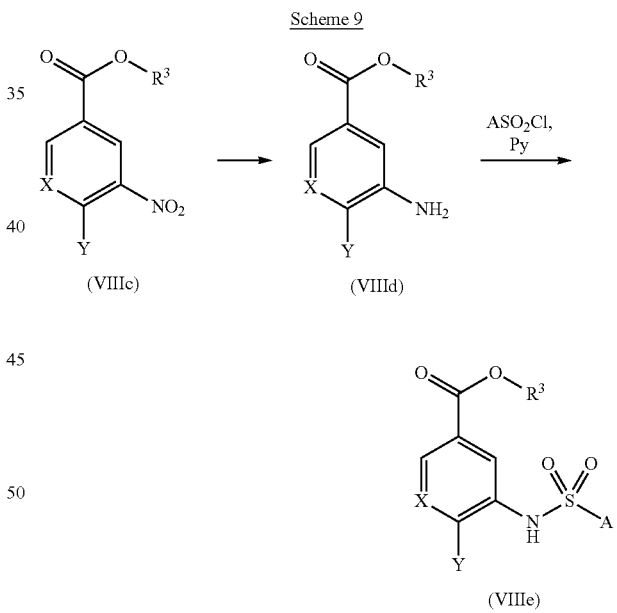

Alternatively, compounds of formula (III), wherein Ra, Y and X are defined as above, may be prepared from compounds of formula (XII) in a two steps process. The first step is a halogen-metal exchange with typically but not exclusively an alkyl lithium salt, such as nBuLi or tBuLi. This step is performed in a suitable solvent such as but not limited to Et2o or THF at temperatures comprised between −20° C. and −100° C., typically −78° C. The second step consists of the addition of CO2, as gas or solid state, as electrophile, as it is outlined in Scheme 10.

Scheme 10

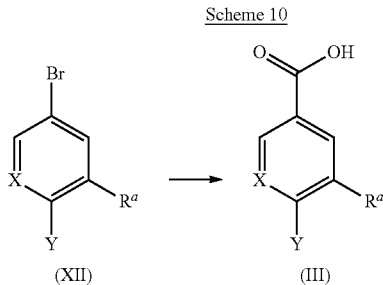

The method for preparing the compounds of formula (III) selected below:
4-(2-Methylpiperidin-1-yl)-3-(trifluoromethyl)benzoic acid
3-cyano-4-(2-methylpiperidin-1-yl)benzoic acid
5-methyl-6-(2-methylpiperidin-1-yl)nicotinic acid
2-(methoxymethyl)-2'-methyl biphenyl-4-carboxylic acid
2-[(dimethylamino)methyl]-2'-methylbiphenyl-4-carboxylic acid
3-(methoxymethyl)-4-(2-methylpiperidin-1-yl)benzoic acid
4-(2-methylpiperidin-1-yl)-3-[(methylsulfonyl)amino]benzoic acid
5-methyl-6-(2-methylpyrrolidin-1-yl)nicotinic acid
2,2'-dimethyl-1,1'-biphenyl-4-carboxylic acid
4-(2-methylpiperidin-1-yl)-3-nitrobenzoic acid
3-methoxy-4-(4-methyl-3-thienyl)benzoic acid
4-(2-ethylpiperidin-1-yl)-3-(methoxymethyl)benzoic acid
2'-ethyl-2-(methoxymethyl)-1,1'-biphenyl-4-carboxylic acid
2'-methyl-2-(trifluoromethyl)biphenyl-4-carboxylic acid
4-[(2R)-2-methylpiperidin-1-yl]-3-(trifluoromethyl)benzoic acid
4-[(2S)-2-methylpiperidin-1-yl]-3-(trifluoromethyl)benzoic acid
is more particularly described in the examples.

Compounds of formula (II), wherein, $R^1$, $R^2$ and Q are defined as above, can be prepared according to Scheme 11 by addition of hydroxylamine to the corresponding compound of formula (XIII) in a solvent or a mixture of solvents, such as EtOH, water, at a temperature ranging from about 20° C. to about 100° C., preferably at RT, for a few hours, e.g. one hour to 24 h.

Scheme 11

The method for preparing the compounds of formula (II) selected below:
N'-hydroxy-1H-benzimidazole-5-carboximidamide
7-fluoro-N'-hydroxy-1H-benzimidazole-5-carboximidamide
N'-hydroxy-7-methyl-1H-benzimidazole-5-carboximidamide
tert-butyl 7-[amino(hydroxyimino)methyl]-3,4-dihydroisoquinoline-2(1H)-carboxylate
tert-butyl [7-[amino(hydroxyimino)methyl]-3,4-dihydroisoquinolin-2(1H)-yl]acetate
N-hydroxy-1-methyl-1H-indole-5-carboximidamide
tert-butyl {5-[(hydroxyamino)(imino)methyl]-1H-indol-1-yl}acetate
ethyl 5-[amino(hydroxyimino)methyl]-6-methoxy-1H-indole-2-carboxylate
N'-hydroxy-1H-indole-5-carboximidamide
N'-hydroxy-1H-indazole-5-carboximidamide
tert-butyl 3-[7-[amino(hydroxyimino)methyl]-3,4-dihydroisoquinolin-2(1H)-yl]propanoate
6-[amino(hydroxyimino)methyl]-1H-indole-2-carboxylic acid
is more particularly described in the examples.

Alternatively, an amine of formula (XIIIa) wherein R1, R2 and Q are as above defined may be transformed into compounds of formula (XIIIb) by addition of a protecting group, using conditions known to the person skilled in the art and as described below in Scheme 12 and in the examples. Typically, protection of the amino group with LG-PG, where LG-is a leaving group, such as but not exclusively Br, I, OMs, and PG is a protecting group such as but not limited to, Boc, Fmoc, Cbz is performed in a solvent such as THF or DCM, in the presence of a base such as DMAP, DIEA, TEA, K2CO3 or Cs2CO3, at temperature ranging from RT to about 100° C. for 1 to 24 hour.

Alternatively, an amine of formula (XIIIa) may be transformed into compounds of formula (XIIIc) by a N-alkylation reaction, using conditions known to the person skilled in the art and as described below in Scheme 12 and in the examples. Typically, N-alkylation with LG-$(CH_2)_m$A, wherein A is as defined above and wherein LG-is a leaving group such as but not exclusively Br, I, OMs, is performed in a solvent such as THF or DMF, in the presence of a base such as DIEA, TEA, $K_2CO_3$ or $Cs_2CO_3$, at temperature ranging from RT to about 100° C.

Scheme 12

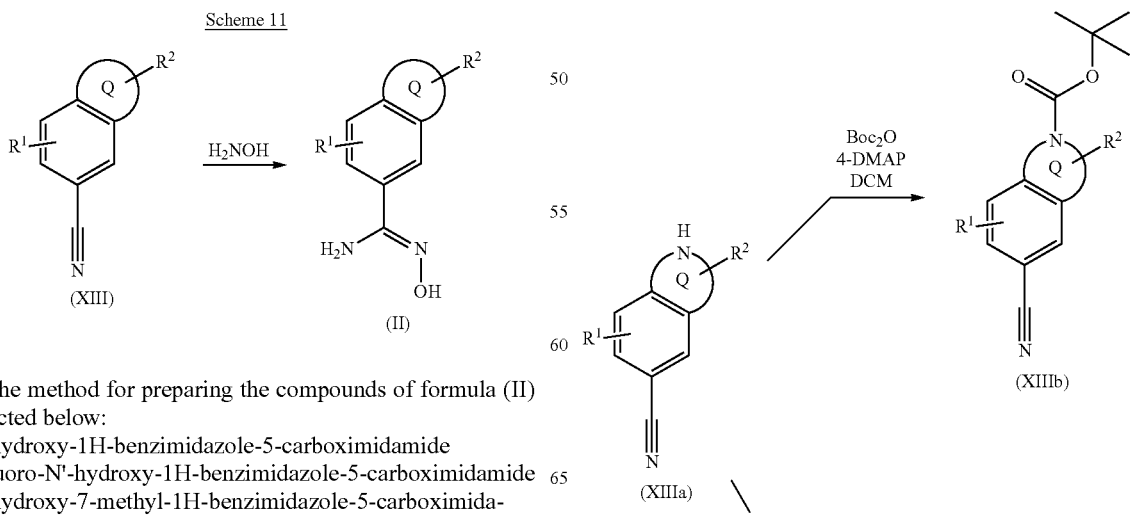

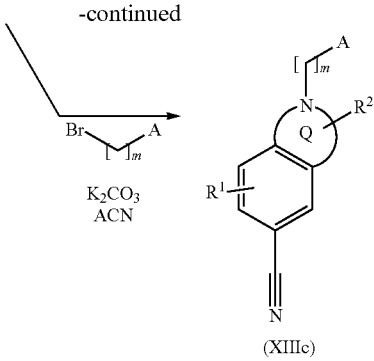

Alternatively, compounds of formula (XIIId), wherein $R^1$ and $R^2$ are defined as above may be obtained from the corresponding diamino compound (XIV) using conditions known to the person skilled in the art and as described below in Scheme 13 and in the examples. Typically, condensation of compound (XIV) with formic acid, is performed in neat formic acid at temperature ranging from RT to reflux for periods of time varying from 3 to 24 hours, preferably 16 h, yields the formation of compounds of formula (XIIId).

Scheme 13

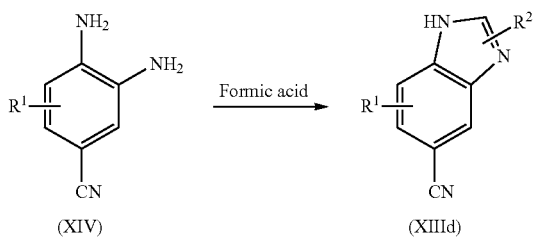

Alternatively, compounds of formula (XIII), wherein $R^1$, $R^2$ and Q are defined as above, may be obtained from the corresponding aryl (XV) wherein $R^1$, $R^2$ and Q are as above defined and $R^c$ is Br or F, by metal catalyzed cyanation, as shown on Scheme 14. Addition of $Zn(CN)_2$ in the presence of a palladium catalyst, such as but not limited to $Pd_2(dba)_3$ or $Pd(PPh_3)_4$, with the optional addition of a ligand such as dppf (according to Maligres, P. E. et al *Tetrahedron Lett.* 1999, 40, 8193-8195), and zinc derivatives such as but not limited to Zn dust and $Zn(OAc)_2$ (according to Chidambaram, R. et al *Tetrahedron Lett.* 2004, 45, 1441-1444) in a solvent such as DMF and at temperature raising from RT to 150° C., typically 100° C., yields the formation of compounds of formula (XIII). The cyanation of aryl compound of formula (XV) can be also performed in the absence of palladium, with the use of CuCN in DMF (according to Couture. C.; Paine, A. J. *Can. J. Chem.* 1985, 63, 111-120).

Scheme 14

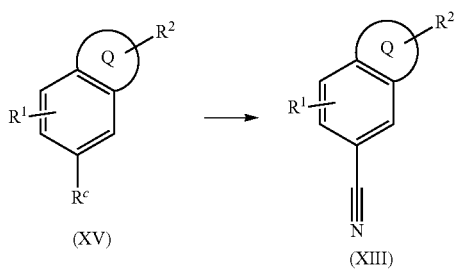

If the above set out general synthetic methods are not applicable for the obtention of compounds of formula (I) and related formulae, suitable methods of preparation known by a person skilled in the art should be used.

The pharmaceutically acceptable cationic salts of compounds of the present invention are readily prepared by reacting the acid forms with an appropriate base, usually one equivalent, in a co-solvent. Typical bases are sodium hydroxide, sodium methoxide, sodium ethoxide, sodium hydride, potassium hydroxide, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of the cation (sodium ethylhexanoate, magnesium oleate), employing a solvent in which the desired cationic salt precipitates, or can be otherwise isolated by concentration and addition of a non-solvent.

According to a further general process, compounds of formula (I) and related formulae can be converted to alternative compounds of formula (I) and related formulae, employing suitable interconversion techniques well known by a person skilled in the art.

In general, the synthesis pathways for any individual compound of formula (I) and related formulae will depend on the specific substituents of each molecule and upon the ready availability of intermediates necessary; again such factors being appreciated by those of ordinary skill in the art. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3rd Edition 1999.

Compounds of this invention can be isolated in association with solvent molecules by crystallization from evaporation of an appropriate solvent. The pharmaceutically acceptable acid addition salts of the compounds of formula (I) and related formulae, which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of formula (I), which contain an acid center, with a suitable base. Both types of salts may be formed or interconverted using ion-exchange resin techniques.

Depending on the conditions used, the reaction times are generally between a few minutes and 14 days, and the reaction temperature is between about −30° C. and 140° C., normally between −10° C. and 90° C., in particular between about 0° C. and about 70° C.

Compounds of the formula (I) and related formulae can furthermore be obtained by liberating compounds of the formula (I) from one of their functional derivatives by treatment with a solvolysing or hydrogenolysing agent.

Preferred starting materials for the solvolysis or hydrogenolysis are those which conform to the formula (I) and related formulae, but contain corresponding protected amino and/or hydroxyl groups instead of one or more free amino and/or hydroxyl groups, preferably those which carry an amino-protecting group instead of an H atom bonded to an N atom, in particular those which carry an R'—N group, in which R' denotes an amino-protecting group, instead of an HN group, and/or those which carry a hydroxyl-protecting group instead of the H atom of a hydroxyl group, for example those which conform to the formula (I), but carry a —COOR" group, in which R" denotes a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC (tert-butoxycarbonyl) and 2-iodoethoxycarbonyl; aralkoxycarbonyl, such as CBZ ("carbobenzoxy"), 4-methoxybenzyloxycarbonyl and FMOC; and arylsulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the formula (I) and related formulae are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature).

The BOC, OBut and Mtr groups can, for example, preferably be cleaved off using TFA in dichloromethane or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be saponified, for example, using acetic acid or using LiOH, NaOH or KOH in water, water/THF, water/THF/ethanol or water/dioxane, at temperatures between 0 and 100° C.

Free amino groups can furthermore be acylated in a conventional manner using an acid chloride or anhydride or alkylated using an unsubstituted or substituted alkyl halide or reacted with $CH_3$—C(=NH)—OEt, advantageously in an inert solvent, such as dichloromethane or THF and/or in the presence of a base, such as triethylamine or pyridine, at temperatures between −60° C. and +30° C.

Throughout the specification, the term leaving group preferably denotes Cl, Br, I or a reactively modified OH group, such as, for example, an activated ester, an imidazolide or alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example through addition of HOBt or N-hydroxysuccinimide.

The formula (I) and related formulae also encompasses the optically active forms (stereoisomers), the enantiomers, the racemates, the diastereomers and the hydrates and solvates of these compounds. The term "solvates of the compounds" is taken to mean adductions of inert solvent molecules onto the compounds which form owing to their mutual attractive force. Solvates are, for example, mono- or dihydrates or alcoholates.

The term "pharmaceutically usable derivatives" is taken to mean, for example, the salts of the compounds of the formula (I) and so-called prodrug compounds.

The term "prodrug derivatives" or "prodrug" is taken to mean compounds of the formula (I) which have been modified with, for example, alkyl or acyl groups, sugars or oligopeptides and which are rapidly cleaved in the organism to form the active compounds.

These also include biodegradable polymer derivatives of the compounds according to the invention, as described, for example, in Int. J. Pharm. 115, 61-67 (1995).

The formula (I) and related formulae also encompasses mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

In a preferred embodiment, the invention relates to compounds of Formula (A)

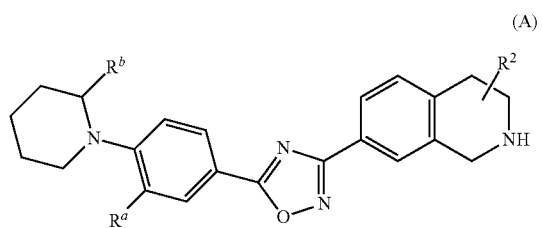

(A)

Wherein $R^a$, $R^b$ and $R^2$ are as above defined and pharmaceutically acceptable derivatives, solvates, tautomers, salts and stereoisomers thereof, including mixtures thereof in all ratios.

In another preferred embodiment, the invention relates to compounds of Formula (B)

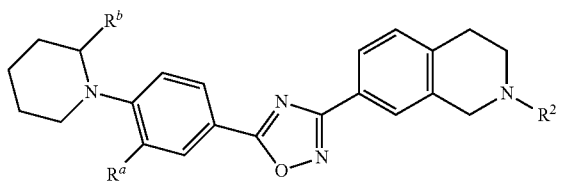

(B)

Wherein $R^a$, $R^b$ and $R^2$ are as above defined,
and pharmaceutically acceptable derivatives, solvates, tautomers, salts and stereoisomers thereof, including mixtures thereof in all ratios.

In another preferred embodiment, the invention relates to compounds of Formula (C)

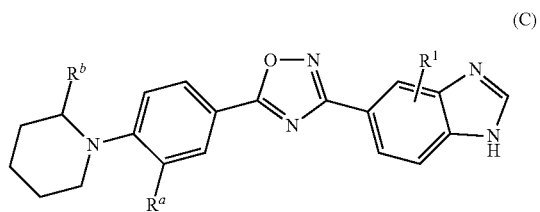

(C)

Wherein $R^1$, $R^a$ and $R^b$ are as above defined,
and pharmaceutically acceptable derivatives, solvates, tautomers, salts and stereoisomers thereof, including mixtures thereof in all ratios.

In another preferred embodiment, the invention provides compounds of Formula (D)

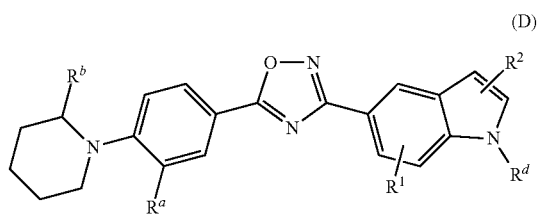

(D)

Wherein $R^a$, $R^b$, $R^1$ and $R^2$ are as above defined and wherein $R^d$ denotes H or A.
and pharmaceutically acceptable derivatives, solvates, tautomers, salts and stereoisomers thereof, including mixtures thereof in all ratios.

In another preferred embodiment, the invention provides compounds of Formula (E)

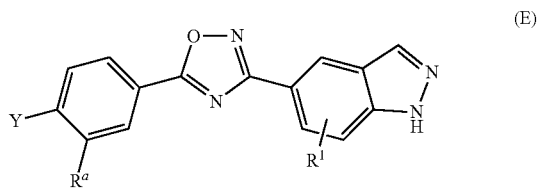

(E)

Wherein Y, $R^1$ and $R^a$ are as above defined.
and pharmaceutically acceptable derivatives, solvates, tautomers, salts and stereoisomers thereof, including mixtures thereof in all ratios.

In another preferred embodiment, the present invention provides compounds of Formula (F):

(F)

Wherein Y and $R^a$ are as above defined.
and pharmaceutically acceptable derivatives, solvates, tautomers, salts and stereoisomers thereof, including mixtures thereof in all ratios.

In another preferred embodiment the present invention provides compounds of Formula (G):

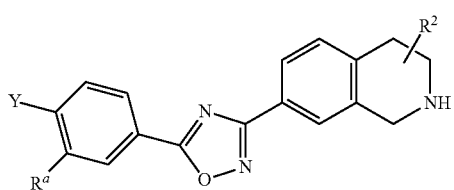

Wherein Y, R$^a$ and R$^2$ are as above defined.
and pharmaceutically acceptable derivatives, solvates, tautomers, salts and stereoisomers thereof, including mixtures thereof in all ratios.

The present invention also provides compounds of Formula (I) wherein Ar denotes a monocyclic or bicyclic, unsaturated or aromatic carbocyclic ring having 6 to 14 carbon atoms, which may be monosubstituted, disubstituted or trisubstituted by Hal, A, OR$^3$, N(R$^3$)$_2$, NO$_2$, CN, COOR$^3$, CF$_3$, OCF$_3$, CON(R$^3$)$_2$, NR$^3$COA, NR$^3$CON(R$^3$)$_2$, NR$^3$SO$_2$A, COR$^3$, SO$_2$N(R$^3$)$_2$, SOA or SO$_2$A, such that at least one atom adjacent to the atom linking the group Ar to the rest of the molecule bears one of said substituents.

Ar preferably denotes a monocyclic aromatic carbocyclic ring having 6 carbon atoms, which is monosubstituted, disubstituted or trisubstituted by Hal, A, OR$^3$, N(R$^3$)$_2$, NO$_2$, CN, COOR$^3$, CF$_3$, OCF$_3$, CON(R$^3$)$_2$, NR$^3$COA, NR$^3$CON(R$^3$)$_2$, NR$^3$SO$_2$A, COR$^3$, SO$_2$N(R$^3$)$_2$, SOA or SO$_2$A, such that at least one atom adjacent to the atom linking the group Ar to the rest of the molecule bears one of said substituents, wherein R$^3$ is as above defined.

Ar most preferably denotes one of the following group:

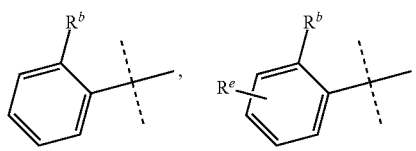

wherein R$^b$ and R$^e$ independently from one another denote A, Hal, OA, OR$^3$, CF$_3$, OCF$_3$.

Het is preferably a 6 to 14 membered ring system and denotes, notwithstanding further substitutions, for example, 2 or 3 furyl, 2 or 3 thienyl, 1,2 or 3 pyrrolyl, 1,2,4 or 5 imidazolyl, 1,3,4 or 5 pyrazolyl, 2,4 or 5 oxazolyl, 3,4 or 5 isoxazolyl, 2,4 or 5 thiazolyl, 3,4 or 5 isothiazolyl, 2,3 or 4-pyridyl, 2,4,5 or 6 pyrimidinyl, furthermore preferably 1,2,3-triazol-1,4- or 5-yl, 1,2,4-triazol-1,3- or 5 yl, 1 or 5 tetrazolyl, 1,2,3-oxadiazol-4- or 5-yl, 1,2,4-oxadi-azol-3- or 5-yl, 1,3,4-thiadiazol-2- or 5-yl, 1,2,4-thiadiazol-3- or 5-yl, 1,2,3-thiadiazol-4- or 5 yl, 3 or 4 pyridazinyl, pyrazinyl, 1,2,3,4,5,6 or 7 indolyl, indazolyl, 4 or 5 isoindolyl, 1,2,4 or 5-benzimidazolyl, 1,3,4,5,6 or 7 benzopyrazolyl, 2,4,5,6 or 7-benzoxazolyl, 3,4,5,6 or 7 benzisoxazolyl, 2,4,5,6 or 7 benzothiazolyl, 2,4,5,6 or 7 benzisothiazolyl, 4,5,6 or 7 Benz-2,1,3-oxadiazolyl, 2,3,4,5,6,7 or 8 quinolyl, 1,3,4,5,6,7 or 8 isoquinolyl, 3,4,5,6,7 or 8 cinnolinyl, 2,4,5,6,7 or 8 quinazolinyl, 5 or 6 quinoxalinyl, 2,3,5,6,7 or 8 2H-benzo-1,4-oxazinyl, furthermore preferably 1,3-benzodioxol-5-yl, 1,4-benzodioxane-6-yl, 2,1,3-benzothiadiazol-4- or 5-yl or 2,1,3-benzoxadiazol-5-yl.

The heterocyclic radicals may also be partially or fully hydrogenated.

Het can thus also denote, for example, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxaneyl, 1,3-dioxane-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or -6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

Het preferably denotes a monocyclic or bicyclic, saturated, unsaturated or aromatic heterocyclic ring having 1 or 2 N atoms, 1 or 2 O atom, or 1 or 2 S atom, and which is monosubstituted, disubstituted or trisubstituted by Hal, A, —[C(R$^3$)$_2$]$_n$—Ar, —[C(R$^3$)$_2$]$_n$-cycloalkyl, OR$^3$, CF$_3$, OCF$_3$, N(R$^3$)$_2$, NR$^3$CON(R$^3$)$_2$, NO$_2$, CN, —[C(R$^3$)$_2$]$_n$—COOR$^3$, —[C(R$^3$)$_2$]$_n$—CON(R$^3$)$_2$, NR$^3$COA, NR$^3$SO$_2$A, COR$^3$, SO$_2$N(R$^3$)$_2$, SOA, and/or SO$_2$A, such that at least one atom adjacent to the atom linking the group Het to the rest of the molecule bears one of said substituents, wherein R$^3$ is as above defined.

When it contains 1 or more nitrogen atoms, Het is preferably linked to the rest of the molecule through the N atom.

Most preferably Het denotes one of the following groups:

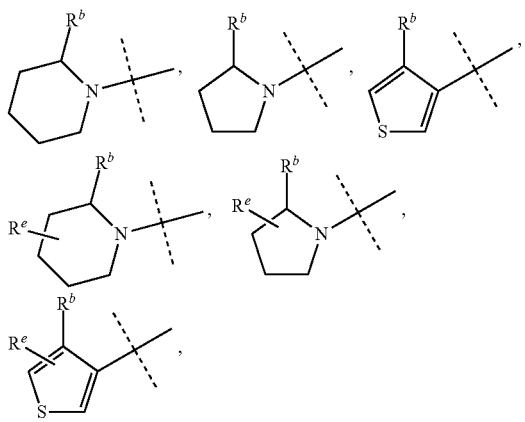

wherein R$^b$ and R$^e$ independently from one another denote A, OA, OR$^3$, CF$_3$, OCF$_3$.

R$^a$ most preferably denotes —CF$_3$, —CN, —CH$_3$, —CH$_2$OCH$_3$, —CH$_2$N(CH$_3$)$_2$, —NHSO$_2$CH$_3$, —NO$_2$, —OCH$_3$, R$^b$ most preferably denotes a C$_1$-C$_6$ alkyl or C$_1$-C$_6$ alkyl wherein one carbon atom is replaced by an oxygen. More preferably R$^b$ denotes methyl, ethyl, —CH$_2$OMe, —CH$_2$OEt.

R$^3$ preferably denotes H or an alkyl having 1 to 6 carbon atoms.

Hal preferably denotes F, Cl or Br.

Preferably, the group A denotes is a branched or linear alkyl having 1 to 6 C-atoms, wherein one or more, preferably 1 to 2 H-atoms may be replaced by $COOR^S$, or $N(R^3)_2$ and wherein one or more, preferably 1 to 2 non-adjacent $CH_2$- groups may be replaced by O, or $NR^3$.
Preferably the group
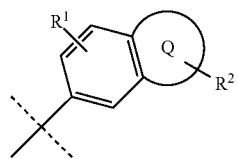
In formula (I) denotes one of the following groups:
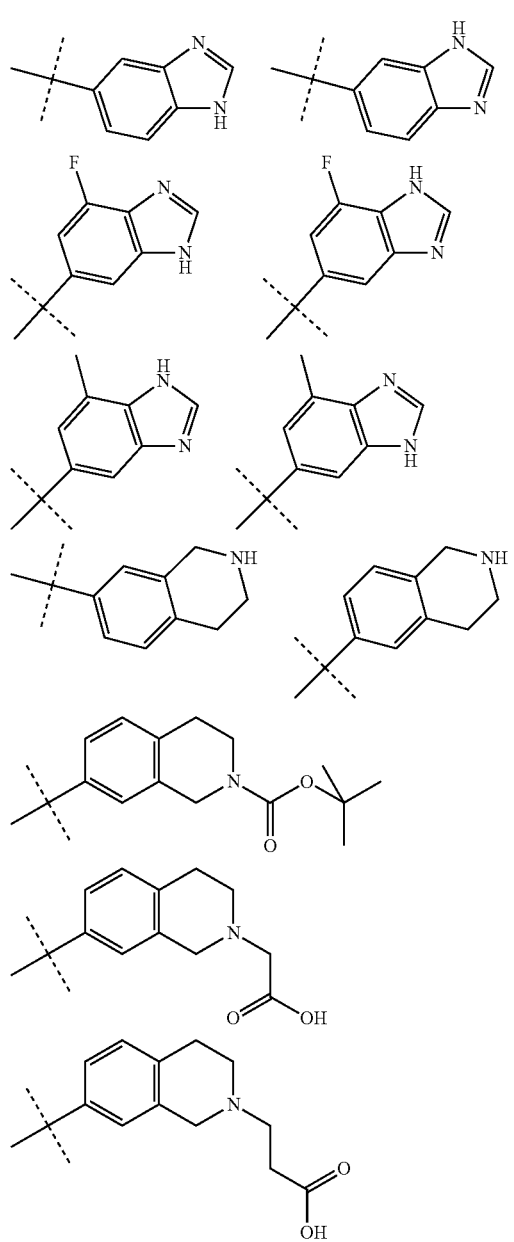
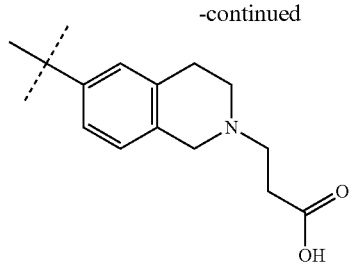
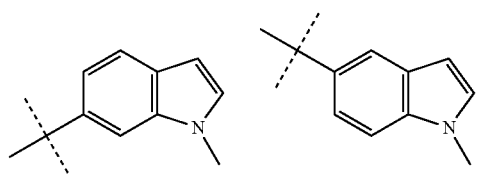
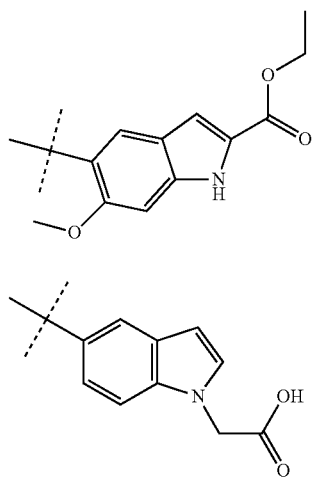
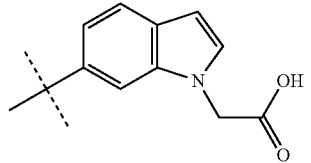
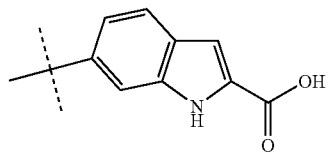
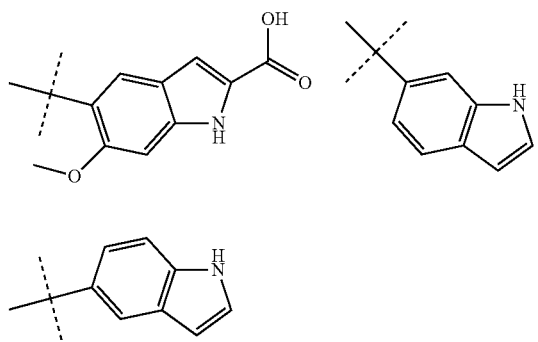

27
-continued
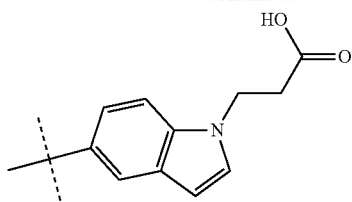
28
-continued
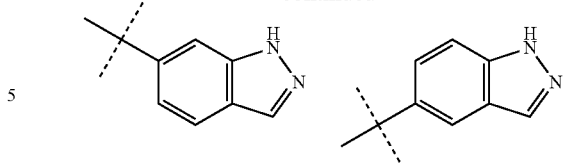
Preference is given to the compounds of formula (I) selected from the following group:
| compound Nb | Structure |
| --- | --- |
| 1 | 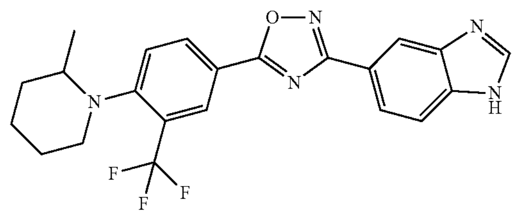 [SMILES: CC1CCCCN1c1ccc(-c2nc(-c3ccc4[nH]cnc4c3)no2)cc1C(F)(F)F] |
| 2 | 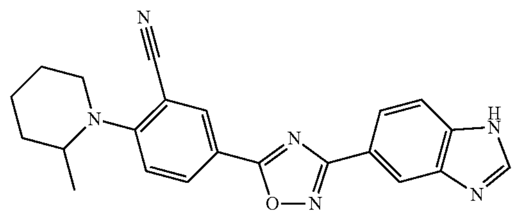 [SMILES: CC1CCCCN1c1ccc(-c2nc(-c3ccc4[nH]cnc4c3)no2)cc1C#N] |
| 3 | 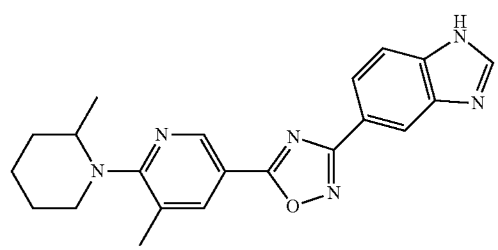 [SMILES: Cc1cc(-c2nc(-c3ccc4[nH]cnc4c3)no2)cnc1N1CCCCC1C] |
| 4 | 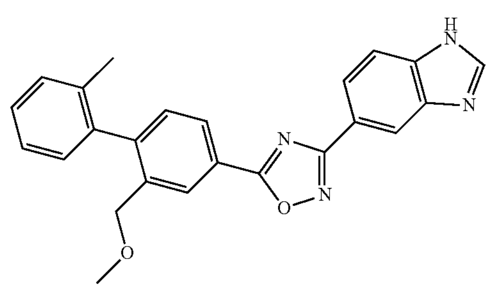 [SMILES: COCc1cc(-c2nc(-c3ccc4[nH]cnc4c3)no2)ccc1-c1ccccc1C] |
| 5 | 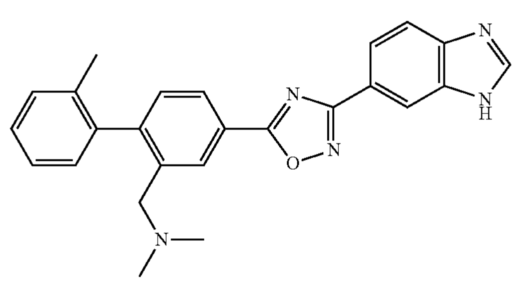 [SMILES: Cc1ccccc1-c1ccc(-c2nc(-c3ccc4nc[nH]c4c3)no2)cc1CN(C)C] |

-continued
| compound Nb | Structure |
|---|---|
| 6 | 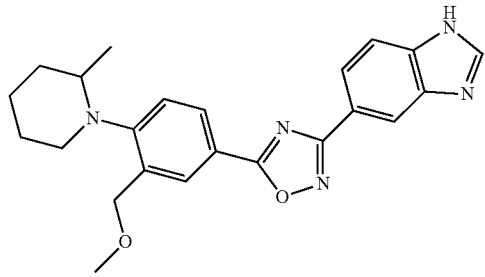 [SMILES: COCc1cc(-c2nc(-c3ccc4[nH]cnc4c3)no2)ccc1N1CCCCC1C] |
| 7 | 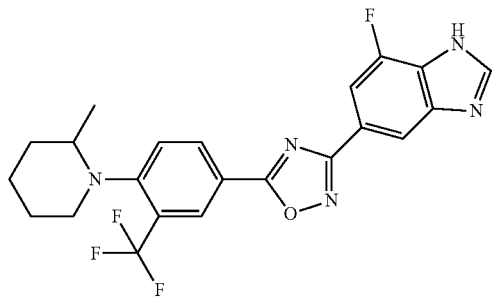 [SMILES: CC1CCCCN1c1ccc(-c2nc(-c3cc(F)c4[nH]cnc4c3)no2)cc1C(F)(F)F] |
| 8 | 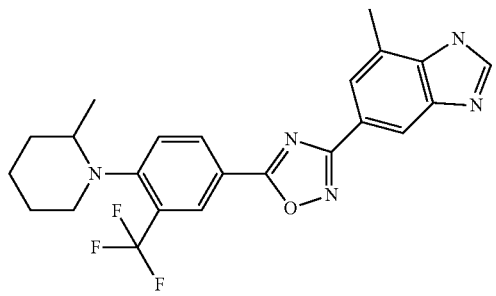 [SMILES: Cc1cc(-c2noc(-c3ccc(N4CCCCC4C)c(C(F)(F)F)c3)n2)cc2nc[nH]c12] |
| 9 | 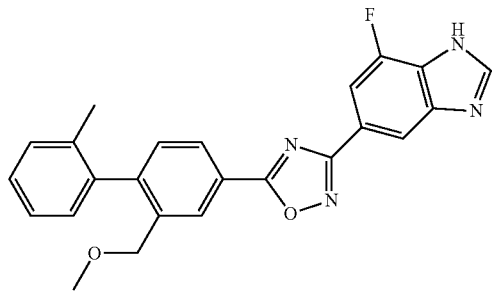 [SMILES: COCc1cc(-c2nc(-c3cc(F)c4[nH]cnc4c3)no2)ccc1-c1ccccc1C] |
| 10 | 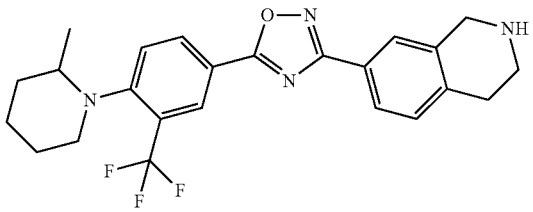 [SMILES: CC1CCCCN1c1ccc(-c2nc(-c3ccc4c(c3)CNCC4)no2)cc1C(F)(F)F] |

-continued

| compound Nb | Structure |
|---|---|
| 11 | 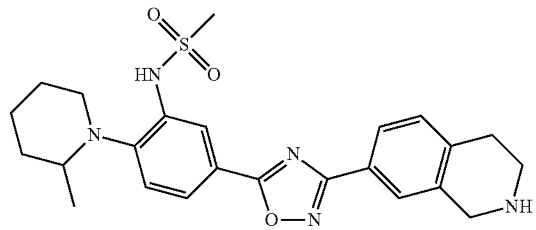 [SMILES: CC1CCCCN1c1ccc(-c2nc(-c3ccc4c(c3)CNCC4)no2)cc1NS(C)(=O)=O] |
| 12 | 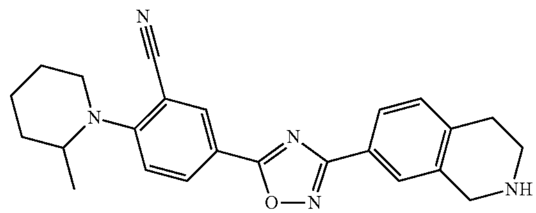 [SMILES: CC1CCCCN1c1ccc(-c2nc(-c3ccc4c(c3)CNCC4)no2)cc1C#N] |
| 13 | 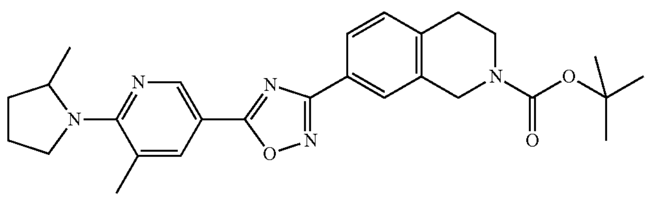 [SMILES: Cc1cc(-c2nc(-c3ccc4c(c3)CN(C(=O)OC(C)(C)C)CC4)no2)cnc1N1CCCC1C] |
| 14 | 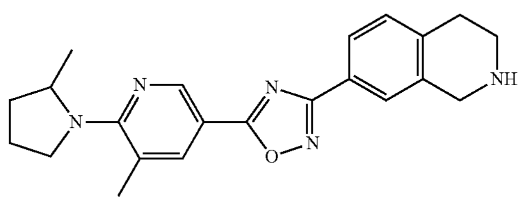 [SMILES: Cc1cc(-c2nc(-c3ccc4c(c3)CNCC4)no2)cnc1N1CCCC1C] |
| 15 | 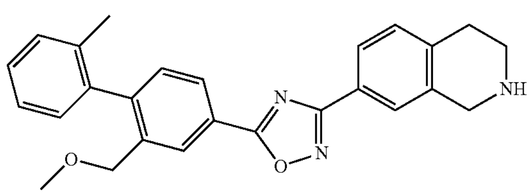 [SMILES: COCc1cc(-c2nc(-c3ccc4c(c3)CNCC4)no2)ccc1-c1ccccc1C] |
| 16 | 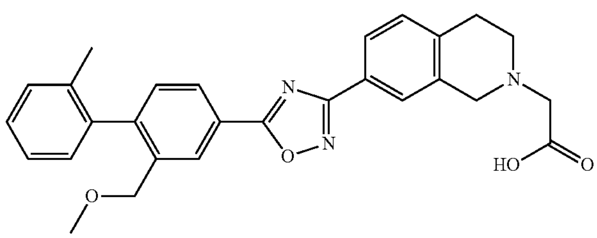 [SMILES: COCc1cc(-c2nc(-c3ccc4c(c3)CN(CC(=O)O)CC4)no2)ccc1-c1ccccc1C] |
| 17 | 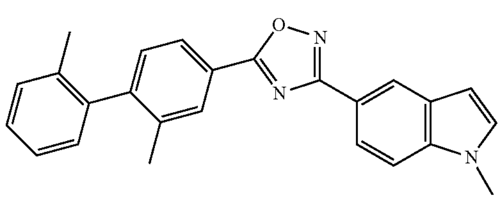 [SMILES: Cc1ccccc1-c1ccc(-c2nc(-c3ccc4c(ccn4C)c3)no2)cc1C] |

-continued

| compound Nb | Structure |
|---|---|
| 18 | 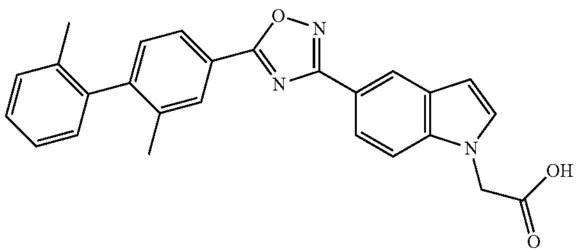 [SMILES: Cc1ccccc1-c1ccc(-c2nc(-c3ccc4c(ccn4CC(=O)O)c3)no2)cc1C] |
| 19 | 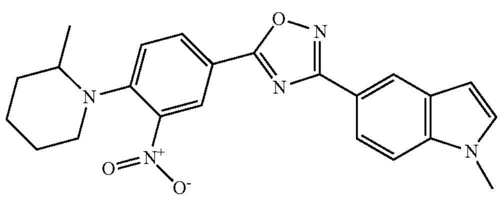 [SMILES: CC1CCCCN1c1ccc(-c2nc(-c3ccc4c(ccn4C)c3)no2)cc1[N+](=O)[O-]] |
| 20 | 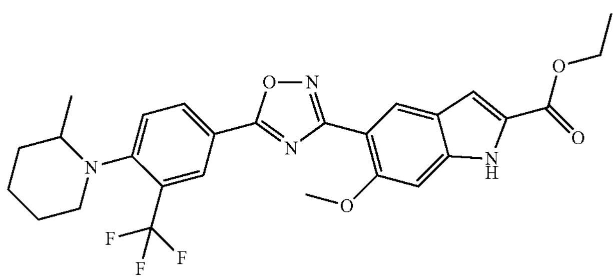 [SMILES: CCOC(=O)c1cc2cc(-c3noc(-c4ccc(N5CCCCC5C)c(C(F)(F)F)c4)n3)c(OC)cc2[nH]1] |
| 21 | 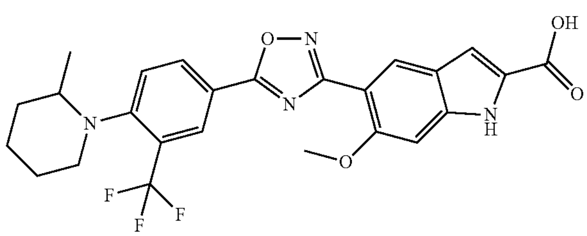 [SMILES: COc1cc2[nH]c(C(=O)O)cc2cc1-c1noc(-c2ccc(N3CCCCC3C)c(C(F)(F)F)c2)n1] |
| 22 | 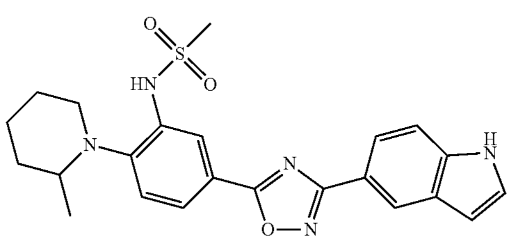 [SMILES: CC1CCCCN1c1ccc(-c2nc(-c3ccc4[nH]ccc4c3)no2)cc1NS(C)(=O)=O] |
| 23 | 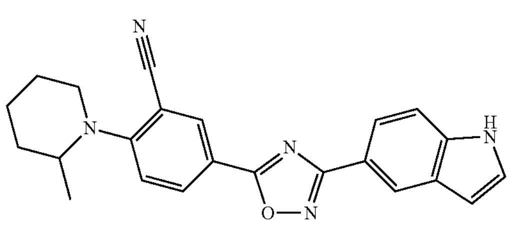 [SMILES: CC1CCCCN1c1ccc(-c2nc(-c3ccc4[nH]ccc4c3)no2)cc1C#N] |

| compound Nb | Structure |
|---|---|
| 24 | 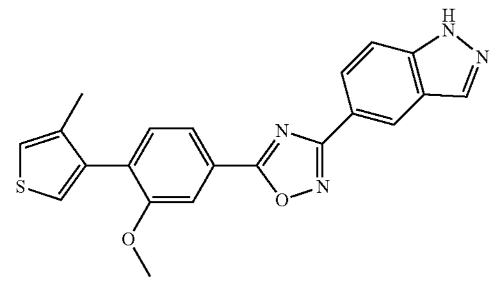 [SMILES: COc1cc(-c2nc(-c3ccc4[nH]ncc4c3)no2)ccc1-c1cscc1C] |
| 25 | 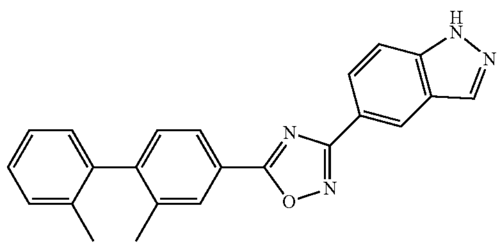 [SMILES: Cc1ccccc1-c1ccc(-c2nc(-c3ccc4[nH]ncc4c3)no2)cc1C] |
| 26 | 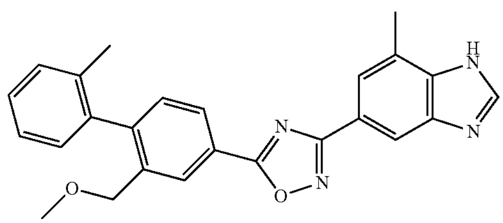 [SMILES: COCc1cc(-c2nc(-c3cc(C)c4[nH]cnc4c3)no2)ccc1-c1ccccc1C] |
| 27 | 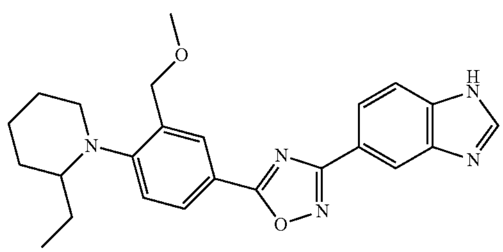 [SMILES: CCC1CCCCN1c1ccc(-c2nc(-c3ccc4[nH]cnc4c3)no2)cc1COC] |
| 28 | 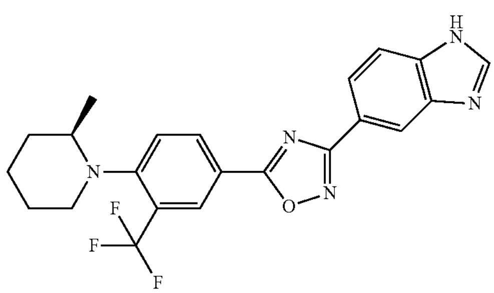 [SMILES: C[C@@H]1CCCCN1c1ccc(-c2nc(-c3ccc4[nH]cnc4c3)no2)cc1C(F)(F)F] |
| 29 | 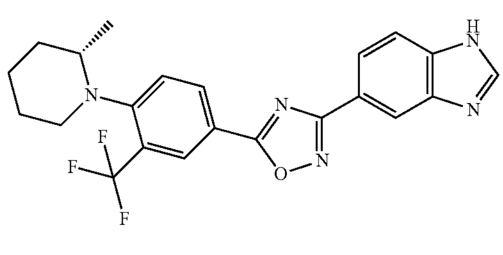 [SMILES: C[C@H]1CCCCN1c1ccc(-c2nc(-c3ccc4[nH]cnc4c3)no2)cc1C(F)(F)F] |

-continued

| compound Nb | Structure |
|---|---|
| 30 | 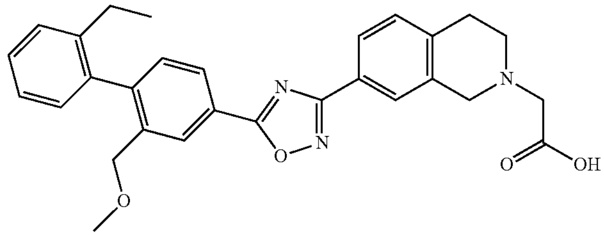 [SMILES: CCc1ccccc1-c1ccc(-c2nc(-c3ccc4c(c3)CN(CC(=O)O)CC4)no2)cc1COC] |
| 31 | 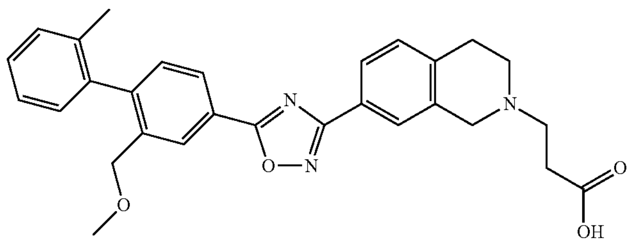 [SMILES: COCc1cc(-c2nc(-c3ccc4c(c3)CN(CCC(=O)O)CC4)no2)ccc1-c1ccccc1C] |
| 32 | 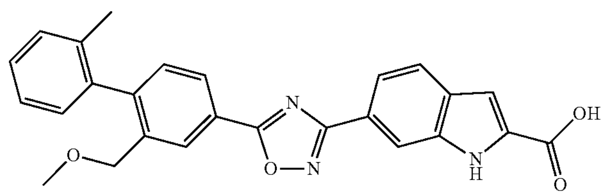 [SMILES: COCc1cc(-c2nc(-c3ccc4cc(C(=O)O)[nH]c4c3)no2)ccc1-c1ccccc1C] |
| 33 | 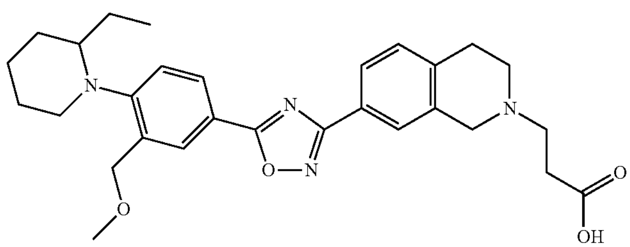 [SMILES: CCC1CCCCN1c1ccc(-c2nc(-c3ccc4c(c3)CN(CCC(=O)O)CC4)no2)cc1COC] |
| 34 | 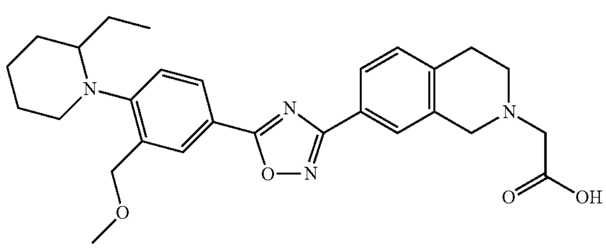 [SMILES: CCC1CCCCN1c1ccc(-c2nc(-c3ccc4c(c3)CN(CC(=O)O)CC4)no2)cc1COC] |
| 35 | 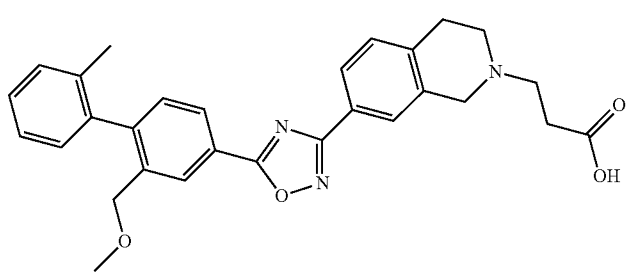 [SMILES: COCc1cc(-c2nc(-c3ccc4c(c3)CN(CCC(=O)O)CC4)no2)ccc1-c1ccccc1C] |

| compound Nb | Structure |
|---|---|
| 36 | 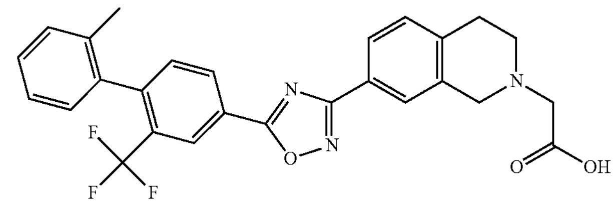 [SMILES: Cc1ccccc1-c1ccc(-c2nc(-c3ccc4c(c3)CN(CC(=O)O)CC4)no2)cc1C(F)(F)F] |
| 37 | 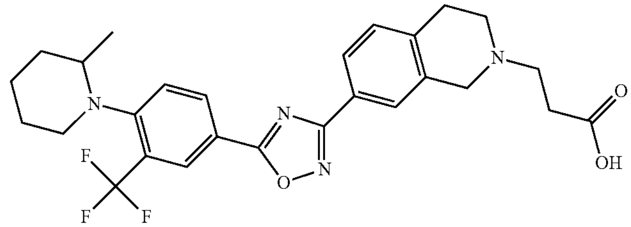 [SMILES: CC1CCCCN1c1ccc(-c2nc(-c3ccc4c(c3)CN(CCC(=O)O)CC4)no2)cc1C(F)(F)F] |
| 38 | 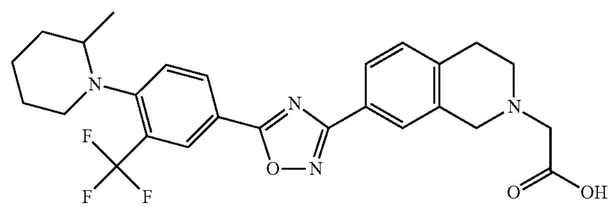 [SMILES: CC1CCCCN1c1ccc(-c2nc(-c3ccc4c(c3)CN(CC(=O)O)CC4)no2)cc1C(F)(F)F] |
| 39 | 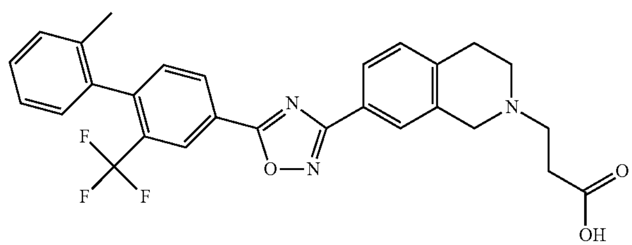 [SMILES: Cc1ccccc1-c1ccc(-c2nc(-c3ccc4c(c3)CN(CCC(=O)O)CC4)no2)cc1C(F)(F)F] |
| 40 | | and pharmaceutically usable derivatives, solvates, salts and stereoisomers thereof, including mixtures thereof in all ratios.

Above and below, all chemical groups and substituents, such as X, Q, Y, $R^1$, $R^2$, $R^3$, $R^a$, $R^b$, A, Het, Ar, Cyc, have the meaning indicated under the formula (I), unless expressly stated otherwise.

In one embodiment, the invention provides compounds of Formula (I) wherein Y, X, $R^a$, $R^1$ and $R^2$ are as above defined and wherein Q denotes a saturated or an unsaturated 5 membered heterocyclic ring containing 1 or 2 nitrogen atoms.

In another specific embodiment, the invention provides compounds of Formula (I) wherein X, Y, $R^a$, $R^1$ and $R^2$ are as above defined and wherein Q denotes a saturated or an unsaturated 5 membered heterocyclic ring containing one oxygen atom.

In another specific embodiment, the invention provides compounds of Formula (I) wherein X, Y, $R^a$, $R^1$ and $R^2$ are as above defined and wherein Q denotes a saturated or an unsaturated 5 membered heterocyclic ring containing one S atom.

In another specific embodiment, the invention provides compounds of Formula (I) wherein X, Y, $R^1$, $R^2$ and Q are as above defined and wherein $R^a$ denotes —OMe, —OEt, —CH$_2$OMe, —NHSO$_2$Me, Me, Et, —CF$_3$, CN, and —NO$_2$.

In another embodiment, the invention provides compounds of Formula (I) wherein X, $R^1$, $R^2$ and $R^a$ are as above defined and wherein Q denotes a saturated 6-membered ring containing one N atom and wherein Y denotes α-methylpyrrolidine.

In another preferred embodiment, the invention provides compounds of Formula (I) wherein X, $R^1$, $R^2$ and $R^a$ are as above defined and wherein Q denotes a saturated 6-membered ring containing one N atom and wherein Y denotes α-methylpiperidine.

In another preferred embodiment, the invention provides compounds of Formula (I) wherein Q, $R^1$ and $R^2$ are as defined under formula (I), X is —N—, Y denotes α-methylpiperidine, $R^a$ denotes methyl.

In another preferred embodiment, the invention provides compounds of Formula (I) wherein X, $R^1$, $R^2$ and $R^a$ are as above defined and wherein Q denotes an unsaturated 5-membered ring containing 1 or 2 N atom and wherein Y is α-methylphenyl.

In another preferred embodiment, the invention provides compounds of Formula (I) wherein X, $R^1$, $R^2$ and $R^a$ are as above defined and wherein Q denotes an unsaturated 5-membered ring containing 1 or 2 N atom and wherein Y is α-methylpiperidine.

In another preferred embodiment, the invention provides compounds of Formula (I) wherein $R^1$ and $R^2$ are independently selected from H, Hal, $COOR^3$, $(CH_2)COOR^3$, $C_1$-$C_6$-alkyl, $(CH_2)_2COOR^3$, wherein $R^3$ is as defined above.

In another preferred embodiment, the invention provides compounds of Formula (I) wherein $R^1$ and $R^2$ are independently selected from H, Hal, $COOR^3$, $(CH_2)COOR^3$, $C_1$-$C_6$-alkyl, $(CH_2)_2COOR^3$, and wherein $R^a$ denotes —OMe, —OEt, —$CH_2$OMe, —$NHSO_2$Me, Me, Et, —$CF_3$, CN, and —$NO_2$.

Alkyl denotes a carbon chain having 1 to 12 carbon atoms, preferably 1 to 8 carbon atoms and most preferably 1 to 6 carbon atoms. Alkyl very preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl Cycloalkyl preferably denotes methylcyclopropyl, methylcyclobutyl, methylcyclopentyl, methylcyclohexyl or methylcycloheptyl.

Cycloalkylalkylene preferably denotes cyclopropylmethylene, cyclobutylmethylene, cyclopentylmethylene, cyclohexylmethylene or cycloheptylmethylene.

Alkylene is preferably methylene, ethylene, propylene, butylene, pentylene or hexylene, furthermore branched alkylene.

Pharmaceutical Salts and Other Forms

The said compounds of the formula I can be used in their final non-salt form. On the other hand, the present invention also relates to the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains an acidic center, such as a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example sodium- or potassiumethoxide and sodium or potassiumpropoxide, alkalihydrides, such as sodium- or potassiumhydride; and various organic bases, such as piperidine, diethanolamine and N-methyl-glutamine, benzathine, choline, diethanolamine, ethylenediamine, meglumine, benethamine, diethylamine, piperazine and tromethamine. The aluminium salts of the compounds of the formula I are likewise included. In the case of certain compounds of the formula I, which contain a basic center, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoaryl-sulfonates, such as ethanesulfonate, toluenesulfonate and benzene-sulfonate, and other organic acids and corresponding salts thereof, such as acetate, trifluoro-acetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzene-sulfonate (besylate), bisulfate, bisulfite, bromide, butyrate, camphorate, camphorsulfonate, caprylate, chloride, chlorobenzoate, citrate, cyclopentane-propionate, digluconate, dihydrogen-phosphate, dinitrobenzoate, dodecyl-sulfate, ethanesulfonate, fumarate, galacterate (from mucic acid), galacturonate, glucoheptanoate, gluco-nate, glutamate, glycerophosphate, hemi-succinate, hemisulfate, heptanoate, hexanoate, hippurate, hydrochloride, hydrobromide, hydroiodide, 2-hydroxy-ethanesulfonate, iodide, isethionate, isobutyrate, lactate, lactobionate, malate, maleate, malonate, mandelate, metaphosphate, methanesulfonate, methylbenzoate, mono-hydrogen-phosphate, 2-naphthalenesulfonate, nicotinate, nitrate, oxalate, oleate, palmo-ate, pectinate, persulfate, phenylacetate, 3-phenylpropionate, phosphate, phosphonate, phthalate, but this does not represent a restriction. Both types of salts may be formed or interconverted preferably using ion-exchange resin techniques.

Furthermore, the base salts of the compounds of the formula I include aluminium, ammonium, calcium, copper, iron (III), iron(II), lithium, magne-sium, manganese(III), manganese(II), potassium, sodium and zink salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzyl-ethylen-ediamine (benzathine), dicyclohexylamine, diethanol-amine, diethylamine, 2-diethyl-amino-ethanol, 2-dimethyl-amino-ethanol, ethanolamine, ethylenediamine, N-ethylmorpholine, N-ethyl-piperidine, glucamine, glucosamine, histidine, hydrabamine, isopropyl-amine, lido-caine, lysine, meglumine (N-methyl-D-glucamine), morpholine, piperazine, piperidine, polyamine resins, procaine, purines, theobromine, triethanol-amine, triethylamine, trimethylamine, tripropylamine and tris(hydroxy-methyl)-methylamine (tromethamine), but this is not intended to represent a restriction.

Compounds of the formula (I) of the present invention which contain basic N-containing groups can be quaternised using agents such as (C1-C4)-alkyl halides, for example methyl, ethyl, isopropyl and tert-butyl chloride, bromide and iodide; di(C1-C4)alkyl sulfates, for example dimethyl, diethyl and diamyl sulfate; (C10-C18)alkyl halides, for example decyl, do-decyl, lauryl, myristyl and stearyl chloride, bromide and iodide; and aryl-(C1-C4)alkyl halides, for example benzyl chloride and phenethyl bromide. Both water- and oil-soluble compounds of the formula I can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, me-glumine, nitrate, oleate, phosphonate, pivalate, sodium phosphate, stearate, sulfate, sulfosalicylate, tartrate, thiomalate, tosylate and tro-meth-amine, but this is not intended to represent a restriction.

The acid-addition salts of basic compounds of the formula (I) are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts other-wise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanol-amine, ethylenediamine, N-methyl-D-glucamine and procaine.

The base-addition salts of acidic compounds of the formula (I) are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts other-wise correspond to the respective free acid forms thereof.

If a compound of the formula I contains more than one group which is capable of forming pharmaceutically acceptable salts of this type, the formula (I) also encompasses multiple salts. Typical multiple salt forms include, for example, bitartrate, diacetate, difumarate, dimeglumine, di-phosphate, disodium and trihydrochloride, but this is not intended to represent a restriction.

With regard to that stated above, it can be seen that the term "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Owing to their molecular structure, the compounds of the formula I can be chiral and can accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the Intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of compounds of formula (I), in combination with at least one further medicament active ingredient, preferably medicaments used in the treatment of multiple sclerosis such as cladribine or another co-agent, such as interferon, e.g. pegylated or non-pegylated interferons, preferably interferon beta and/or with compounds improving vascular function. These further medicaments, such as interferon beta, may be administered concomitantly or sequentially, e.g. by subcutaneous, intramuscular or oral routes.

These compositions can be used as medicaments in human and veterinary medicine.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medica-ment after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinyl-pyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting molds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be formulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula (I) and salts, solvates and physiologically functional derivatives thereof and the other active ingredients can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula (I) and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouth-washes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

The present invention furthermore relates to a method for treating a subject suffering from a sphingosine 1-phosphate associated disorder, comprising administering to said subject an effective amount of a compounds of formula I. The present invention preferably relates to a method, wherein the sphingosine 1-phosphate-1 associated disorder is an autoimmune disorder or condition associated with an overactive immune response.

The present invention furthermore relates to a method of treating a subject suffering from an immunerogulatory abnormality, comprising administering to said subject a compounds of formula I in an amount that is effective for treating said immunoregulatory abnormality. The present invention preferably relates to a method wherein the immunoregulatory abnormality is an autoimmune or chronic inflammatory disease selected from the group consisting of: amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma. The present invention furthermore relates to a method wherein the immunoregulatory abnormality is bone marrow or organ transplant rejection or graft-versus-host disease. The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

Preferred compounds of formula (I) exhibit a EC50 in GTPγS for the binding to the $S_1P_1$ receptor of less than about 10 μM, preferably less than about 5 μM, more preferably less than about 1 μM and even more preferred less than about 0.1 μM. Most preferably, compounds of Formula (I) exhibit a EC50 for the binding of S1P1 less than 0.01 μM.

Preferred compounds of Formula (I) exhibit a well pronounced activity against lymphopenia.

Preferred compounds of Formula (I) exhibit a selectivity on S1P1 receptor over the S1P3 receptor of a magnitude of more than about 20. More preferably, compounds of formula (I) are 50 fold selective for S1P1 compare to S1P3, more preferably, 100 fold, even more preferably 1000 fold.

In the following the present invention shall be illustrated by means of some examples, which are not construed to be viewed as limiting the scope of the invention.

EXAMPLES

The compounds according to formula (I) can be prepared from readily available starting materials by several synthetic approaches, using both solution-phase and solid-phase chemistry protocols or mixed solution and solid phase protocols. Examples of synthetic pathways are described below in the examples.

The commercially available starting materials used in the following experimental description were purchased from Aldrich or Fluka unless otherwise reported.

The HPLC, NMR and MS data provided in the examples described below are obtained as followed:
HPLC Data:

Method A: HPLC columns: Xbridge™ C8 column 50 mm×4.6 mm at a flow of 2 mL/min; 8 min gradient from 0.1% TFA in $H_2O$ to 0.07% TFA in ACN.

Method B: HPLC columns: ATLANTIS C18 75×4.6 mm 5 U at a flow of 1 mL/min; A-0.1% HCOOH B-ACN.

Method C: HPLC columns: C18 BDS, 50×4.6 mm, SC\307 at a flow of 0.8 mL/min; A-0.1% TFA, B-ACN: Flow—0.8 mL/min.

Method D: HPLC columns: Waters Xterra 5μ C18 (2), 250×4.6 mm at a flow of 1 mL/min; 30 min gradient from 95:5 ([10 mM ammonium bicarbonate in $H_2O$]: MeCN) to MeCN.

UV detection (maxplot) for all methods.
Mass Spectrum:

Method A: LC/MS Waters ZMD (ESI); GC/MS: GC Agilent 6890N & MS Agilent 5973.

Method B: HPLC/MS: Waters Acquity, column Waters Acquity HPLC BEH C18 1.7 m 2.1×50 mm, conditions:

solvent A (10 mM ammonium acetate in water+5% ACN), solvent B (ACN), gradient 5% B to 100% B over 3 min, UV detection (PDA, 230-400 nm) and MS detection (SQ detector, positive and negative ESI modes, cone voltage 30 V).

$^1$H-NMR Data:

Bruker DPX-300 MHz unless otherwise reported.

Autoprep Purifications:

Preparative HPLC purifications are performed with a mass directed autopurification Fractionlynx from Waters equipped with a Sunfire Prep C18 OBD column 19×100 mm 5 m, unless otherwise reported. All HPLC purifications were performed with a gradient of ACN/$H_2O$ or ACN/$H_2O$/HCOOH (0.1%).

The microwave chemistry was performed on a single mode microwave reactor Emrys™ Optimiser from Personal Chemistry.

Hydrogenation reactions are performed with H-Cube™ Continuous-flow Hydrogenation Reactor—Continuous hydrogenation reactions are performed in a flow system. The hydrogen gas necessary for the reaction is generated in-situ. Reactions take place on disposable proprietary CatCarts™, packed catalyst columns modeled after conventional HPLC systems. Every aspect of the operation on the H-Cube is controlled and monitored using a touch-screen panel.

Intermediate 1: N'-hydroxy-1H-benzimidazole-5-carboximidamide

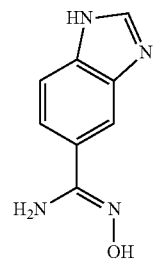

Step 1: 1H-benzimidazole-5-carbonitrile

A solution of 3,4-diaminobenzonitrile (1 g; 7.51 mmol) in formic acid (40 mL) was heated at reflux for 3 hours then concentrated in vacuo to give a brown oily residue. It was extracted with EtOAc from a saturated aqueous solution of $NaHCO_3$, dried over $MgSO_4$ and evaporated under vacuum to give the title compound as a light pink solid (1.05 g, 98%). 1H NMR (DMSO-$d_6$): δ 12.97 (br s, 1H), 8.48 (s, 1H), 8.16 (d, J=0.8 Hz, 1H), 7.76 (d, J=8.3 Hz, 1H), 7.59 (dd, J=8.3, 1.5 Hz, 1H). LC/MS (Method B): 144.1 (M+H)$^+$.

Step 2: N'-hydroxy-1H-benzimidazole-5-carboximidamide

To a suspension of 1H-benzimidazole-5-carbonitrile obtained in step 1 (1 g; 6.99 mmol) in EtOH (20 mL) was added hydroxylamine (50% in water, 2.10 mL; 34.93 mmol) and the mixture was stirred at RT for 36 hours. The solution was concentrated under vacuum to give the title compound as a light pink solid (1.15 g, 93%). $^1$H NMR (DMSO-d$_6$): δ 12.52 (br s, 1H), 9.51 (s, 1H), 8.23 (s, 1H), 7.89 (br s, 1H), 7.56 (s, 2H), 5.80 (s, 2H).

Intermediate 2: 7-fluoro-N'-hydroxy-1H-benzimidazole-5-carboximidamide

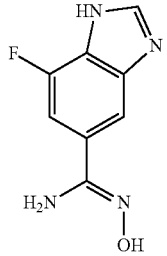 [SMILES: N/C(=N\O)c1cc(F)c2[nH]cnc2c1]

Step 1: 5-bromo-7-fluoro-1H-benzimidazole

A solution of 5-bromo-2,3-diaminofluorobenzene (Apollo, 3 g; 14.63 mmol) in formic acid (75 mL) was heated at reflux overnight after which the reaction mixture was concentrated under vacuum to give a brown oil. It was extracted with EtOAc from a saturated aqueous solution of NaHCO$_3$, dried over MgSO$_4$ and evaporated under vacuum to give the title compound as a light pink solid (2.91 g, 92%). $^1$H NMR (DMSO-d$_6$): δ 8.30 (s, 1H), 7.62 (d, J=1.5 Hz, 1H), 7.27 (dd, J=10.3, 1.5 Hz, 2H), 3.32 (bs, 2H). HPLC (Method A), Rt: 2.09 min (purity: 97.4%). LC/MS (Method B): 216.9 (M+H)$^+$.

Step 2: 7-fluoro-1H-benzimidazole-5-carbonitrile

A suspension of 5-bromo-7-fluoro-1H-benzimidazole obtained from step 1 (2.50 g; 11.63 mmol), zinc cyanide (Adrich, 819 mg; 6.98 mmol), tris(dibenzylideneacetone)dipalladium (Adrich, 319 mg; 0.35 mmol), 1,1-bis(diphenylphosphino)ferrocene (483 mg; 0.87 mmol), zinc (Adrich, 30 mg; 0.47 mmol) and zinc acetate (Adrich, 85 mg; 0.47 mmol) in dry DMF (25 mL) under inert atmosphere was heated at 120° C. for 16 hours. Reaction mixture was filtered over a pad of celite washed with EtOAc. The organics were washed with water, dried over MgSO$_4$ and evaporated under vacuum to afford a brown solid that was triturated with EtOH and filtered to give the title compound as a brown solid $^1$H NMR (DMSO-d$_6$) δ 13.40 (bs, 1H), 8.55 (s, 1H), 8.04 (s, 1H), 7.51-7.48 (d, J=10.7 Hz, 1H). LC/MS (Method B): 162.1 (M+H)$^+$.

Step 3: 7-fluoro-N'-hydroxy-1H-benzimidazole-5-carboximidamide

The title compound was prepared following the procedure described for Intermediate 1, step 2, but starting from 7-fluoro-1H-benzimidazole-5-carbonitrile obtained in step 2 (750 mg; 4.65 mmol) as a beige solid (814 mg, 90%). $^1$H NMR (DMSO-d$_6$) δ 12.88 (bs, 1H), 9.67 (s, 1H), 9.30 (s, 1H), 7.68 (s, 1H), 7.33-7.29 (m, 1H), 5.89 (s, 2H). LC/MS (Method B): 195.1 (M+H)+.

Intermediate 3: N'-hydroxy-7-methyl-1H-benzimidazole-5-carboximidamide

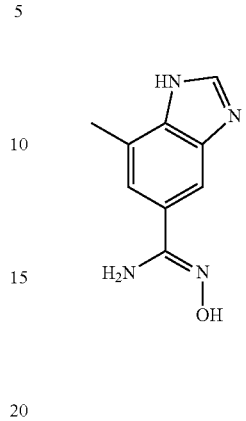

Step 1: 5-bromo-7-methyl-1H-benzimidazole

A solution of 5-bromo-3-methyl-benzene-1,2-diamine (Maybridge, 3 g; 14.92 mmol) in formic acid (75 mL) was heated at reflux for 16 hours. Reaction mixture was concentrated under vacuum to give a brown oil. It was extracted by EtOAc from a saturated aqueous solution of NaHCO$_3$, dried over MgSO$_4$ and evaporated under vacuum to give the title compound as a pale yellow solid (3.07 g, 97%). $^1$H NMR (DMSO-d$_6$) δ 12.92-12.34 (bs, 1H), 8.22 (s, 1H), 7.59 (br s, 1H), 7.17 (s, 1H), 3.33 (s, 3H). LC/MS (Method B): 211.0 (M+H)$^+$.

Step 2: 7-methyl-1H-benzimidazole-5-carbonitrile

A suspension of 5-bromo-7-methyl-1H-benzimidazole obtained in step 1 (2.80 g; 13.27 mmol), zinc cyanide (934 mg; 7.96 mmol), tris(dibenzylideneacetone)dipalladium (364 mg; 0.40 mmol), 1,1'-bis(diphenylphosphino)ferrocene (551 mg; 0.99 mmol), zinc (34 mg; 0.53 mmol) and zinc acetate (97 mg; 0.53 mmol) in dry DMF (28 mL) under inert atmosphere was heated at 120° C. for 16 hours. Reaction mixture was filtered over a pad of celite and washed with EtOAc. The organics were washed with water, dried over MgSO$_4$ and evaporated under vacuum to afford a brown solid that was triturated with EtOH, filtered to give the title compound as a beige solid. $^1$H NMR (DMSO-d$_6$) δ 13.11 (br s, 1H), 8.45 (s, 1H), 8.02-7.90 (m, 1H), 7.42 (m, 1H), 2.54 (m, 3H). LC/MS (Method B): 158.2 (M+H)$^+$.

Step 3: N'-hydroxy-7-methyl-1H-benzimidazole-5-carboximidamide

The title compound was prepared following the procedure described for Intermediate 1, step 2, but starting from 7-methyl-1H-benzimidazole-5-carbonitrile obtained in step 2 (900 mg; 5.73 mmol) as a beige solid (985 mg, 90%). $^1$H NMR (DMSO-d$_6$) δ 12.60 (br s, 1H), 9.46 (s, 1H), 8.29-7.57 (m, 3H), 5.76 (s, 2H), 2.51 (m, 3H). LC/MS (Method B): 191.1 (M+H)$^+$.

Intermediate 4: tert-butyl 7-[-amino(hydroxyimino)methyl]-3,4-dihydroisoquinoline-2(1H)-carboxylate

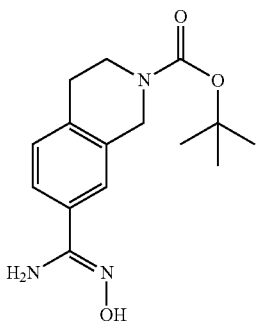 [SMILES: CC(C)(C)OC(=O)N1CCc2ccc(/C(N)=N/O)cc2C1]

Step 1: tert-butyl 7-cyano-3,4-dihydroisoquinoline-2(1H)-carboxylate

Catalytic DMAP was added to a suspension of 7-cyano-1,2,3,4-tetrahydroisoquinoline (ABCR, 1.58 g; 10 mmol) and di-tert-butyl dicarbonate (2.61 g; 12 mmol) in $CH_3CN$ (50 mL) and the resulting mixture was stirred at RT for 16 hours. The heterogeneous mixture was concentrated under vacuum and the residue was extracted with EtOAc from water, dried over $MgSO_4$ and evaporated under vacuum to give a yellow oil that was purified by silica column chromatography(c-hexane/EtOAc, 85/15 then 80/20) to give the title compound as a colorless oil. $^1$H NMR (DMSO-d6) δ 7.70 (bs, 1H), 7.61 (dd, J=8, 1.6 Hz, 1H), 7.36 (d, J=8 Hz, 1H), 4.53 (s, 2H), 3.55 (t, J=5.9 Hz, 2H), 2.85 (t, J=5.9 Hz, 2H), 1.42 (s, 9H). HPLC (Method A), Rt 4.18 min (Purity: 99.5%).

Step 2: tert-butyl 7-[amino(hydroxyimino)methyl]-3,4-dihydroisoquinoline-2(1H)-carboxylate The title compound was prepared following procedure described for Intermediate 1, step 2, but starting from tert-butyl 7-cyano-3,4-dihydroisoquinoline-2(1H)-carboxylate obtained in step 1 (1.50 g; 5.81 mmol). The solvent was evaporated in vacuo and further freeze dried to give the title compound as an off-white solid (1.35 g, 80%). $^1$H NMR (DMSO-$d_6$) δ 9.54 (s, 1H), 7.46 (m, 2H), 7.14 (d, J=8 Hz, 1H), 5.74 (bs, 2H), 4.49 (s, 2H), 3.54 (t, J=5.9 Hz, 2H), 2.76 (t, J=5.9 Hz, 2H), 1.49 (s, 9H). HPLC (Method A), Rt 2.40 min (Purity: 99.4%). LC/MS (Method B): 292.2 (M+H)$^+$.

Intermediate 5: tert-butyl [7-[amino(hydroxyimino)methyl]-3,4-dihydroisoquinolin-2(1H)-yl]acetate

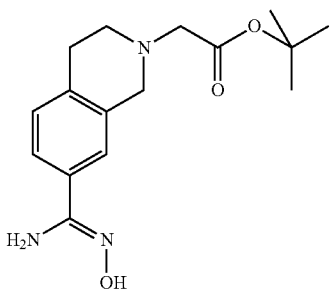 [SMILES: CC(C)(C)OC(=O)CN1CCc2ccc(/C(N)=N/O)cc2C1]

Step 1: tert-butyl (7-cyano-3,4-dihydroisoquinolin-2(1H)-yl)acetate

To a suspension of 7-cyano-1,2,3,4-tetrahydroisoquinoline (ABCR, 2 g; 12.64 mmol) and $K_2CO_3$ (3.49 g, 25.28 mmol) in $CH_3CN$ (40 mL), was added tert-butyl bromoacetate (1.96 mL; 13.27 mmol) and the reaction mixture was stirred at RT for 4 hours. Solvents were removed under vacuum and solid residue was extracted with EtOAc from a saturated aqueous solution of $NaHCO_3$, dried over $MgSO_4$ and evaporated under vacuum to give the title compound a as colorless oil (3.32 g; 96%). $^1$H NMR (DMSO-$d_6$) δ 7.55 (m, 2H), 7.30 (m, 1H), 3.72 (s, 2H), 3.31 (s, 2H), 2.86-2.79 (m, 4H), 1.49 (s, 9H). LC/MS (Method B): 217.1 (M+1-1)$^+$.

Step 2: tert-butyl [7-[amino(hydroxyimino)methyl]-3,4-dihydroisoquinolin-2(1H)-yl]acetate The title compound was prepared following procedure described for Intermediate 1, step 2, but starting from tert-butyl (7-cyano-3,4-dihydroisoquinolin-2(1H)-yl)acetate obtained in step 1 (3.32 g; 12.19 mmol) as a pale yellow powder (3.69 g; 99%). $^1$H NMR (DMSO-$d_6$) δ 9.50 (s, 1H), 7.43-7.40 (m, 1H), 7.33 (m, 1H), 7.08 (d, J=8 Hz, 1H), 5.71 (bs, 2H), 3.68 (s, 2H), 3.30 (s, 2H), 2.78 (s, 4H), 1.43 (s, 9H). HPLC (Method A), Rt 1.82 min (Purity: 91.1%). LC/MS (Method B): 306.2 (M+H)$^+$.

Intermediate 6: N-hydroxy-1-methyl-1H-indole-5-carboximidamide

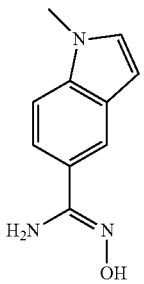

Step 1: 1-methyl-1H-indole-5-carbonitrile

A mixture of 5-bromoindole (500 mg; 2.55 mmol) and cuprous cyanide (342 mg; 3.83 mmol) in NMP (10 mL) was heated under microwave irradiations to 100° C. for 30 minutes then at 200° C. for 30 minutes. The reaction mixture was partitioned with water and DCM and the organic layer was washed with brine and concentrated in vacuo to give a pink solid. Purification by silica column chromatography (DCM) gave a white solid. It was dissolved in DMF (5 mL) and $K_2CO_3$ (704 mg; 5.10 mmol) and iodomethane (543 mg; 3.83 mmol) were successively added. The reaction mixture was stirred at RT for 3 days and then partitioned between water and EtOAc. The organic layer was washed with brine, dried over $MgSO_4$ and concentrated under vacuum to give a slightly yellow oil which crystallized upon standing to give the title compound as an off-white solid (80 mg, 70%). LC/MS (Method A): 156.9 (M+H)+.

Step 2: N-hydroxy-1-methyl-1H-indole-5-carboximidamide

The title compound was prepared following procedure described for Intermediate 1, step 2, but starting from 1-methyl-1H-indole-5-carbonitrile obtained in step 1 (285 mg; 1.82 mmol) in EtOH (3 mL) as an off-white solid (325 mg, 94%). $^1$H NMR (DMSO-$d_6$) δ 9.37 (s, 1H), 7.84 (s, 1H), 7.52-7.48 (m, 1H), 7.40-7.37 (m, 1H), 7.33-7.32 (m, 1H), 6.43 (d, J=3 Hz, 1H), 5.70 (bs, 2H), 3.78 (s, 3H).

Intermediate 7: tert-butyl {5-[(hydroxyamino)(imino)methyl]-1H-indol-1-yl}acetate

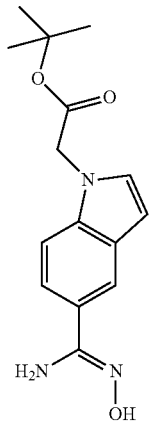 [SMILES: CC(C)(C)OC(=O)Cn1ccc2cc(/C(N)=N/O)ccc21]

Step 1: tert-butyl (5-cyano-1H-indol-1-yl)acetate tert-butyl bromoacetate (0.88 mL; 5.99 mmol) was added to a suspension of 5-cyanoindole (0.71 g; 4.99 mmol) and $K_2CO_3$ (1.38 g; 9.99 mmol) in $CH_3CN$ (20 mL) and the resulting mixture was stirred at reflux for 16 hours. Filtration and concentration in vacuo gave a light yellow oil which crystallized upon standing. The solid was triturated in a mixture of $Et_2O$ and hexane to give the title compound as an off-white solid (1.26 g, 98%). HPLC (Method A), Rt: 4.43 min (Purity: 96.8%). LC/MS (Method B): 256.9 (M+H)$^+$.

Step 2: tert-butyl {5-[(hydroxyamino)(imino)methyl]-1H-indol-1-yl}acetate

The title compound was prepared following procedure described for Intermediate 1, step 2, but starting from tert-butyl (5-cyano-1H-indol-1-yl)acetate obtained in step 1 (512 mg; 2 mmol) as a white solid (558 mg, 97%). $^1$H NMR (DMSO-d$_6$) δ 9.38 (s, 1H), 7.84 (s, 1H), 7.49-7.45 (m, 1H), 7.33-7.29 (m, 2H), 6.47 (d, J=3 Hz, 1H), 5.71 (bs, 2H), 4.99 (s, 2H), 1.40 (s, 9H). HPLC (Method A), Rt 2.54 min (Purity: 94.6%). LC/MS (Method B): 290.0 (M+H)$^+$.

Intermediate 8: ethyl 5-[amino(hydroxyimino)methyl]-6-methoxy-1H-indole-2-carboxylate

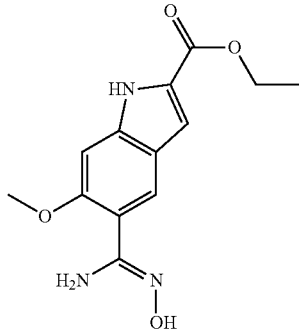 [SMILES: CCOC(=O)c1cc2cc(/C(N)=N/O)c(OC)cc2[nH]1]

Step 1: ethyl 5-bromo-6-methoxy-1H-indole-2-carboxylate

A solution of sodium ethylate in ethanol (prepared from sodium (1.92 g; 83.70 mmol) and EtOH (40 mL)) was added dropwise to a cold (−10° C.) solution of 3-bromo-p-anisaldehyde (4 g; 18.60 mmol) and ethyl azidoacetate (ABCR, 27.80 ml; 46.50 mmol) in EtOH (60 mL). After the end of the addition, the reaction mixture was warmed up to 0° C. and stirred at RT for 5 hours. The heterogenous mixture was poured onto ice and stirred for 30 minutes. The solid was collected by filtration and dried under high vacuum. The solid was taken up in xylenes (60 mL) and heated to reflux for 3 hours. The solvent was evaporated and the residue was purified by silica column chromatography (c-Hexane/ethyl acetate, 80/20) to give the title compound as a pale yellow solid. $^1$H NMR (DMSO-d$_6$) δ 11.87 (s, 1H), 7.89 (s, 1H), 7.05 (s, 1H), 6.98 (s, 1H), 4.31 (q, J=7 Hz, 2H), 3.85 (s, 3H), 1.32 (t, J=7 Hz, 3H). HPLC (Method A), Rt 4.28 min (Purity: 98.1%). LC/MS (Method B): 297.2 (M+H)+.

Step 2: ethyl 5-cyano-6-methoxy-1H-indole-2-carboxylate

A mixture of ethyl 5-bromo-6-methoxy-1H-indole-2-carboxylate obtained in step 1 (300 mg; 1.01 mmol) and cuprous cyanide (108 mg; 1.21 mmol) in NMP (10 mL) was heated under microwave irradiations at 200° C. for 30 minutes. The dark solution was filtered through a short pad of silica, which was washed with DCM. The obtained dark red solution was concentrated in vacuo and the oily residue was precipitated in water. The solid was collected by filtration, washed thoroughly with water and dried under high vacuum. Purification by silica column chromatography (DCM then DCM/MeOH, 99/1) gave the title compound as a slightly pink solid. HPLC (Method A), Rt 3.45 min (Purity: 97.4%). LC/MS (Method B): 243.2 (M+H)$^+$.

Step 3: ethyl 5-[amino(hydroxyimino)methyl]-6-methoxy-1H-indole-2-carboxylate

The title compound was prepared following procedure described for Intermediate 1, step 2, but starting from ethyl 5-cyano-6-methoxy-1H-indole-2-carboxylate obtained in step 1 (120 mg; 0.49 mmol) as a beige solid (135 mg, 99%). $^1$H NMR (DMSO-d$_5$) δ 9.25 (s, 1H), 7.60 (s, 1H), 7.11 (s, 1H), 6.90 (s, 1H), 5.53 (bs, 2H), 4.31 (q, J=7 Hz, 2H), 3.80 (s, 3H), 1.32 (t, J=7 Hz, 3H).

Intermediate 9: N'-hydroxyl-1H-indole-5-carboximidamide

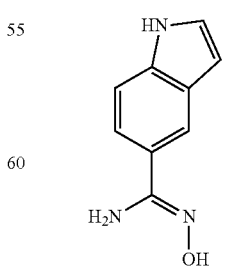

The title compound was prepared following procedure described for Intermediate 1, step 2, but starting from 5-cyanoindole (2 g; 14.07 mmol) as a brown solid (2.4 g, 97%). HPLC (Method A), Rt 0.95 min (Purity: 88.8%). LC/MS (Method B): 176.1 (M+H)+.

Intermediate 10:
N'-hydroxy-1H-indazole-5-carboximidamide

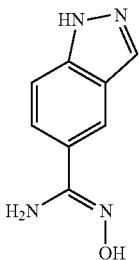

The title compound was prepared following procedure described for Intermediate 1, step 2, but starting from 1H-indazole-5-carbonitrile (JW-Pharmalab, 0.50 g; 3.49 mmol) as a beige solid (560 mg, 91%). ¹H NMR (DMSO-d₆) δ 13.12 (s, 1H), 9.54 (s, 1H), 8.10 (s, 1H), 8.04 (s, 1H), 7.71 (d, J=8.7 Hz, 1H), 7.49 (d, J=8.7 Hz, 1H), 5.82 (bs, 2H).

Intermediate 11: 4-(2-Methylpiperidin-1-yl)-3-(trifluoromethyl)benzoic acid

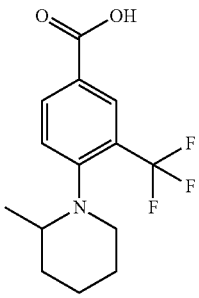 [SMILES: CC1CCCCN1c1ccc(C(=O)O)cc1C(F)(F)F]

Step 1: 4-(2-methylpiperidin-1-yl)-3-(trifluoromethyl)benzonitrile 4-fluoro-3-(trifluoromethyl)benzonitrile (Combi-blocks, 50 g; 264.40 mmol) and 2-methylpiperidine (Acros, 156.08 mL; 1 321.98 mmol) in DMSO (500 mL) were heated at 100° C. under nitrogen for 12 h. After this time, Et₂O and water were added to the reaction mixture and organic phase was washed with water, NaHCO₃ and a saturated aqueous solution of NH₄Cl successively. Organics were dried over MgSO₄, evaporated under vacuum to give the title compound as a beige powder. ¹H NMR (DMSO-d₆) δ 8.19 (d, J=2 Hz, 1H), 8.12 (dd, J=8.4, 2 Hz, 1H), 7.75 (d, J=8.2 Hz, 1H), 3.15-3.10 (m, 1H), 2.90-2.85 (m, 1H), 2.60-2.51 (m, 1H), 1.77-1.25 (m, 6H), 0.72 (d, J=6.0 Hz, 3H). LC/MS (Method B): 269.2 (M+H)+.

Step 3: 4-(2-Methylpiperidin-1-yl)-3-(trifluoromethyl)benzoic acid 4-(2-methylpiperidin-1-yl)-3-(trifluoromethyl)benzonitrile obtained in step 1 (28 g; 104.37 mmol) was dissolved in MeOH (280 mL) to which was added sodium hydroxide (336 mL; 5 M) and the reaction mixture was heated at 100° C. for 7 h. After this time, reaction mixture was cooled to 0° C. and acidified to pH ~2 with HCl (5N). Product precipitated as a white solid that was filtered, washed with water and dried under vacuum to give the title compound as a white powder (27.50 g; 91%). ¹H NMR (DMSO-d₆) δ 13.30 (bs, 1H), 8.20-8.14 (m, 2H), 7.68 (d, J=8.2 Hz, 1H), 3.08 (m, 1H), 3.10-3.06 (m, 1H), 2.90-2.86 (m, 1H), 2.59-2.54 (m, 1H), 1.77-1.25 (m, 6H), 0.72 (d, J=6.0 Hz, 3H). HPLC (Method B) Rt 5.37 min (Purity: 99.8%). LC/MS (Method B): 288.2 (M+H)+.

Intermediate 12:
3-cyano-4-(2-methylpiperidin-1-yl)benzoic acid

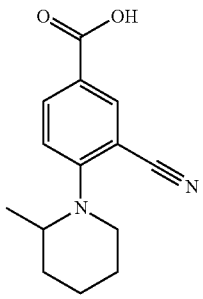 [SMILES: CC1CCCCN1c1ccc(C(=O)O)cc1C#N]

2-Methylpiperidine (2.38 mL; 20.29 mmol) was added to a solution of methyl 3-cyano-4-fluorobenzoate, prepared as described in J. Med. Chem. 2004, 47, 1339-1350 from 2-fluoro-5-formylbenzonitrile (727 mg; 4.06 mmol) in DMF (4 mL). The resulting mixture was stirred at RT for 2 days. The solution was partitioned between EtOAc and water and the phases separated. The organic layer was washed with HCl (0.1 M) and brine, dried over MgSO4. Evaporation under reduced pressure afforded a greenish oil. The latter was taken up in THF (10 mL), LiOH (340 mg; 8.12 mmol) and water (10 mL) were added and the reaction mixture was stirred at RT for 16 hours. The resulting solution was diluted with water and washed with Et2O. The aqueous layer was made acidic (pH 2) by addition of HCl (1M) and extracted with EtOAc. The organic phase was dried over MgSO4 and concentrated in vacuo to give a light yellow oil that precipitated upon trituration with a mixture of EtOAc and n-pentane to give the title compound as an off-white solid. 1H NMR (DMSO-d6) δ 13 (br s, 1H), 8.08 (d, J=2.1 Hz, 1H), 8.01 (dd, J=8.8, 2.1 Hz, 1H), 7.18 (d, J=8.9 Hz, 1H), 4.12-4.08 (m, 1H), 3.35-3.25 (m, 2H), 1.84-1.53 (m, 6H), 1.09 (d, J=6.6 Hz, 3H). LC/MS (Method B): 243.2 (M–H)–; 245.2 (M+H)+.

Intermediate 13:
5-methyl-6-(2-methylpiperidin-1-yl)nicotinic acid

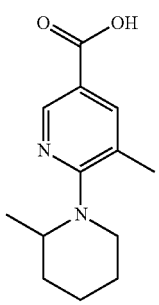

Step 1: 5-methyl-6-(2-methylpiperidin-1-yl)nicotinonitrile

A solution of 5-cyano-2-fluoro-3-methylpyridine (Molekula, 1.50 g; 11.02 mmol) and 2-methylpiperidine (5.20 mL; 44.08 mmol) was heated to 90° C. for 18 h. Reaction mixture was extracted with EtOAc, the organics dried over MgSO$_4$, evaporated under vacuum to give the title compound as a brown oil (2.2 g, 93%). $^1$H NMR (DMSO-d$_6$) δ 8.46 (d, J=2.3 Hz, 1H), 7.82 (d, J=2.3 Hz, 1H), 4.01-3.96 (m, 1H), 3.37-3.25 (m, 2H), 3.17-3.09 (m, 1H), 2.22 (s, 3H), 1.72-1.46 (m, 6H), 1.11 (d, J=6.6 Hz, 3H). HPLC (Method B) Rt 3.60 min (Purity: 84.5%). LC/MS (Method A): 216.2 (M+H)$^+$.

Step 2: 5-methyl-6-(2-methylpiperidin-1-yl)nicotinic acid

A solution of 5-methyl-6-(2-methylpiperidin-1-yl)nicotinonitrile obtained in step 1 (1.0 g; 4.64 mmol) and KOH (1.3 g; 23.22 mmol) in water (60 mL) was heated at reflux for 16 hours. After this time, reaction mixture was acidified to pH 3 and extracted with EtOAc to give the title compound as a yellow solid (1.1 g, quantitative). $^1$H NMR (DMSO-d$_6$) δ 12.82 (bs, 1H), 8.58 (d, J=2.3 Hz, 1H), 7.88 (d, J=2.3 Hz, 1H), 3.85-3.82 (m, 1H), 3.19-3.10 (m, 2H), 2.24 (s, 3H), 1.75-1.44 (m, 6H), 1.04 (d, J=6.2 Hz, 3H). HPLC (Method B) Rt 1.96 min (Purity: 92.2%). LC/MS (Method A): 235.2 (M+H)$^+$.

Intermediate 14: 2-(methoxymethyl)-2'-methyl biphenyl-4-carboxylic acid

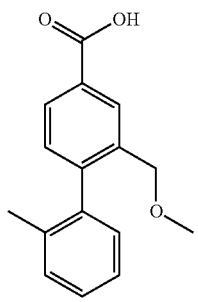

Step 1: Methyl 4-bromo-3-(bromomethyl)benzoate

Under N$_2$, to a solution of methyl 4-bromo-3-methylbenzoate (50 g; 218.27 mmol) in CHCl3 (1 000 mL) were added NBS (Merck, 46.62 g; 261.93 mmol) in one portion and α,α'-azoisobutyronitrile (0.72 g; 4.37 mmol). The mixture was stirred at 70° C. for 2 days. The reaction mixture was cooled to RT and water (500 mL) was added. The organic layer was washed with of a saturated aqueous solution of NaHCO$_3$, water (340 mL), then brine (500 mL), dried over MgSO$_4$ and concentrated affording the title compound as a yellow solid. It was washed with pentane (2×500 mL) affording the title compound as a yellow solid. $^1$H NMR (DMSO-d$_6$) δ 8.24 (d, J=1.91 Hz, 1H), 7.88-7.82 (m, 2H), 4.87 (s, 2H), 3.91 (s, 3H). HPLC (Method A) Rt 4.44 min (Purity: 97.9%).

Step 2: Methyl 4-bromo-3-(methoxymethyl)benzoate

A solution of methyl 4-bromo-3-(bromomethyl)benzoate obtained in step 1 (37.50 g; 121.77 mmol) in MeOH (1 125 mL) was refluxed for 4 days. After concentration, the mixture was partitioned between EtOAc (500 mL) and water (200 mL). The organic layer was washed with a 5% NaHCO$_3$ aqueous solution (200 mL), brine (200 mL), dried over MgSO$_4$ and concentrated affording the title compound as a beige solid (29.8 g, 94%). $^1$H NMR (DMSO-d$_6$) δ 8.06-8.05 (m, 1H), 7.83 (d, J=1.23 Hz, 2H), 4.54 (m, 2H), 3.90 (s, 3H), 3.45 (s, 3H). LC/MS (Method B): 227.2 (M−H)$^-$. HPLC (Method A) Rt 4.42 min (Purity: 93.0%).

Step 3: Methyl 2-(methoxymethyl)-2'-methylbiphenyl-4-carboxylate

Methyl 4-bromo-3-(methoxymethyl)benzoate obtained in step 2 (40 g; 154.38 mmol; 1 eq.), o-tolylboronic acid (23.09 g; 169.82 mmol; 1.10 eq.), K2CO3 (106.68 g; 771.90 mmol; 5 eq.), tetrakis(triphenylphosphine)palladium (0) (1.78 g; 1.54 mmol; 0.01 eq.) were taken up in toluene (200 mL) and water (200 mL) under nitrogen atmosphere. The reaction mixture was purged with vacuum, then degassed with nitrogen and then refluxed for 1 hour. The reaction mixture was cooled to room temperature, filtered over a pad of celite and washed with EtOAc (1000 mL). The filtrate was concentrated to afford a yellow oil which was taken in EtOAc (800 mL). The organic layer was washed with a saturated aqueous solution of NaHCO$_3$ solution (250 mL), water (250 mL) and brine (250 mL), dried over MgSO$_4$ and concentrated affording the title compound as a yellow oil used without further purification (41.9 g, quantitative). HPLC (Method A) Rt 5.34 min (Purity: 89.4%).

Step 4: 2-(methoxymethyl)-2'-methylbiphenyl-4-carboxylic acid

To a solution of methyl 2-(methoxymethyl)-2'-methylbiphenyl-4-carboxylate obtained in step 3 (40 g; 147.97 mmol) in EtOH (1200 mL) was added NaOH (88.78 mL; 5 M; 443.90 mmol) after which the mixture was heated at 60° C. for one hour. Reaction mixture was cooled to room temperature and concentrated under vacuum to give a yellow solid. Water was added and the aqueous phase was washed with EtOAc. The aqueous phase was then acidified with HCl (1 M) and extracted with EtOAc to give the title compound as a yellow solid (35.1 g, 92%). $^1$H NMR (DMSO-d$_6$) δ 12.99 (br s, 1H), 8.09 (s, 1H), 7.92-7.89 (m, 1H), 7.33-7.22 (m, 4H), 7.10-7.08 (m, 1H), 4.11 (m, 2H), 3.18 (s, 3H), 1.99 (s, 3H). HPLC (Method A) Rt 4.52 min (Purity: 96.4%). LC/MS (Method B): 255.2 (M−H)$^-$.

Intermediate 15: 2-[(dimethylamino)methyl]-2'-methylbiphenyl-4-carboxylic acid

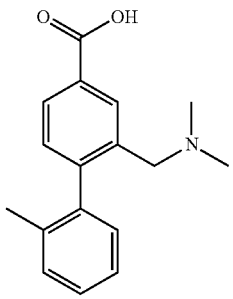

Step 1: Methyl 4-bromo-3-(bromomethyl)benzoate

To a solution of methyl 4-bromo-3-methylbenzoate (50 g; 218 mmol) in CHCl$_3$ (1 L) were added NBS (46.6 g; 262 mmol) in one portion and α,α'-azoisobutyronitrile (0.72 g; 4.37 mmol). The reaction mixture was stirred at 70° C. for 2 days. It was cooled down to RT and water was added. The organic layer was washed with aq. NaHCO$_3$, then brine, dried over MgSO$_4$ and concentrated in vacuo. The residue was washed with n-pentane to afford the title compound as a yellow solid. $^1$H NMR (DMSO-d$_6$) δ 8.24 (d, J=1.9 Hz, 1H), 7.88-7.82 (m, 2H), 4.87 (s, 2H), 3.91 (s, 3H). HPLC (Method A): Rt 4.44 min (purity 97.9%).

Step 2: Methyl 3-[(acetyloxy)methyl]-4-bromobenzoate

To a solution of methyl 4-bromo-3-(bromomethyl)benzoate obtained in step 1 (6.5 g; 21 mmol) in AcOH (32.5 mL) was added sodium acetate (3.46 g; 42 mmol) and the reaction mixture was stirred at 100° C. for 12 hours. After concentration in vacuo, the residue was partitioned between EtOAc and water. The organic layer was washed with 5% aq. NaHCO$_3$ then brine, dried over MgSO$_4$ and concentrated in vacuo. Purification by silica column chromatography (c-hexane/EtOAc, 5/1) afforded the title compound as a white solid (4.78 g, 79%). $^1$H NMR (DMSO-d$_6$) δ 8.03 (m, 1H), 7.85-7.84 (d, J=1.3 Hz, 1H), 5.18 (s, 2H), 3.87 (s, 3H), 2.11 (s, 3H). HPLC (Method A) Rt 4.37 min (purity 98.1%).

Step 3: Methyl 2-[(acetyloxy)methyl]-2'-methylbiphenyl-4-carboxylate

A mixture of methyl 3-[(acetyloxy)methyl]-4-bromobenzoate obtained in step 2 (4.7 g; 16.4 mmol), o-tolylboronic acid (2.45 g; 18 mmol), potassium carbonate (11.3 g; 82 mmol) and Pd(PPh$_3$)$_4$ (1.89 g; 1.64 mmol) in toluene (23.5 mL) and water (23.5 mL) was refluxed for 2 hours. After cooling to RT, the reaction mixture was filtered through a pad of Celite® which was further washed with toluene (50 mL). The filtrate was concentrated in vacuo, the residue taken up in EtOAc (250 mL) and washed with sat. aq. NaHCO$_3$, water and brine, dried over magnesium sulphate and concentrated in vacuo to afford the title compound (4.9 g, quantitative) as a brown oil. HPLC (Method A) Rt 5.23 min (Purity 62.3%).

Step 4: methyl 2-[(dimethylamino)methyl]-2'-methylbiphenyl-4-carboxylate

To a solution of methyl 2-(hydroxymethyl)-2'-methylbiphenyl-4-carboxylate obtained in step 3 (2.12 g; 8.27 mmol) in DCM (63.6 mL) was added at 0° C. DIEA (7.03 mL; 41.36 mmol) and methanesulfonyl chloride (768 μL; 9.93 mmol) at 0° C. and stirred at 25 min. After this time, dimethylamine (12.41 mL; 2 M; 24.81 mmol) was added to the reaction mixture and stirred at RT for 16 hours. Reaction mixture was partitioned between DCM and an aqueous solution of NaOH (5 M). Purification by silica column chromatography (DCM/[DCM/MeOH 2:1] gradient) gave the title compound as a light yellow solid (2.03 g, 86%). $^1$H NMR (DMSO-d6) δ 8.27 (d, J=1.4 Hz, 1H), 7.95 (dd, J=7.8, 1.9 Hz, 1H), 7.32-7.18 (m, 4H), 7.06 (d, J=7.3 Hz, 1H), 3.94 (s, 3H), 3.24-3.10 (m, 2H), 2.11 (s, 6H), 2.01 (s, 3H). HPLC (Method A) Rt 2.90 min (Purity 100.0%). LC/MS (Method B): 284.1 (M−H)$^-$.

Step 5: 2-[(dimethylamino)methyl]-2'-methylbiphenyl-4-carboxylic acid

To a solution of methyl 2-[(dimethylamino)methyl]-2'-methylbiphenyl-4-carboxylate obtained in step 4 (687 mg; 2.42 mmol) in water (20 mL) at RT was treated with HCl (12 mL; 5 M; 60 mmol). The reaction mixture was refluxed at 105° C. for 4 hours, evaporated under vacuum, taken up in ACN and evaporated under vacuum to give the title compound as a light yellow powder (719 mg; 96%). $^1$H NMR (DMSO-d6) δ 13.23 (br s, 1H), 10.31 (br s, 1H), 8.47 (s, 1H), 8.03 (d, J=7.2 Hz, 1H), 7.38-7.31 (m, 4H), 7.20 (d, J=7.2 Hz, 1H), 4.32 (d, J=13.2 Hz, 1H), 3.87 (d, J=13.2 Hz, 1H), 2.61 (s, 3H), 2.50 (s, 3H), 1.98 (s, 3H). HPLC (Method A) Rt 2.52 min (Purity 100.0%).

Intermediate 16: 3-(methoxymethyl)-4-(2-methylpiperidin-1-yl)benzoic acid

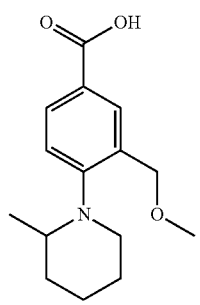

Step 1: 5-bromo-2-(2-methylpiperidin-1-yl)benzaldehyde

To a solution of 5-bromo-2-fluorobenzaldehyde (13.20 g; 65.02 mmol) in DMSO (160 mL) and water (40 mL) were added 2-methylpiperidine (15.35 mL; 130.04 mmol) and anhydrous sodium carbonate (13.78 g; 130.04 mmol). The resulting mixture was heated at 120° C. for 16 h after which it was allowed to cool to RT. Reaction mixture was partitioned between H$_2$O and Et$_2$O and the combined organic layers were washed with brine (pH 5-6 adjusted with HCl), dried over MgSO$_4$, filtered and dried under vacuum to give the title compound as a brown yellow oil (16.3 g, 89%). $^1$H NMR (CDCl$_3$, 300 MHz) δ 10.40 (s, 1H), 7.93 (d, J=2.5 Hz, 1H), 7.62 (dd, J=8.6, 2.5 Hz, 1H), 7.12 (d, J=8.6 Hz, 1H), 3.17 (m, 1H), 3.06 (m, 1H), 2.81 (ddd, J=11.7, 7.6, 3.9 Hz, 1H), 1.89 (m, 1H), 1.83-1.65 (m, 3H), 1.58-1.42 (m, 2H), 0.91 (d, J=6.3 Hz, 3H). HPLC (Method A): Rt 2.20 min (Purity: 93.7%). LC/MS (Method B): 282.1 (M+H)$^+$.

Step 2: [5-bromo-2-(2-methylpiperidin-1-yl)phenyl]methanol

To a solution of 5-bromo-2-(2-methylpiperidin-1-yl)benzaldehyde obtain in step 1 (16.30 g; 57.76 mmol) in MeOH (300 mL) was added sodium borohydride (2.19 g; 57.76 mmol) at 5° C. in a portion-wise fashion and stirred for 30 min. After this time, reaction mixture was diluted with a saturated aqueous solution of NH$_4$Cl, extracted with EtOAc. The organic layers were washed with aqueous solution of NH$_4$Cl, brine, dried over MgSO$_4$ and evaporated under vacuum to give the title compound as a yellow oil (15.9 g, 97%). $^1$H NMR (CDCl$_3$, 300 MHz) δ 7.38 (dd, J=8.5, 2.4 Hz, 1H), 7.26 (d, J=2.4 Hz, 1H), 7.13 (d, J=8.5 Hz, 1H), 6.40 (brs, 1H), 4.86 (d, J=13.9 Hz, 1H), 4.67 (d, J=13.9 Hz, 1H), 3.06-2.88 (m, 2H), 2.61 (td, J=11.4, 3.2 Hz, 1H), 1.88-1.58 (m, 4H), 1.53-1.32 (m, 2H), 0.90 (d, J=6.2 Hz, 3H). LC/MS (Method A): 285.6 (M+H)⁺. HPLC (Method A): Rt 2.13 min (Purity: 94.9%).

Step 3: 1-[4-bromo-2-(methoxymethyl)phenyl]-2-methylpiperidine

To a solution of solution of [5-bromo-2-(2-methylpiperidin-1-yl)phenyl]methanol obtain in step 2 (7.9 g; 27.8 mmol) and n-ethyldiisopropylamine (10.40 mL; 61.15 mmol) in anhydrous DCM (150 mL) cooled to 0° C., was added methanesulfonyl chloride (2.36 mL; 30.57 mmol). The reaction mixture was diluted with MeOH (150 mL) and heated at 50° C. for 3 h after which time solvents were removed under vacuum to give a brown oil. Residue was taken up with Et₂O, washed with water (pH 8 adjusted with aqueous NaOH), saturated aqueous solution of NH₄Cl and brine. The combined organic layers were dried over MgSO₄, filtered and the solvent was removed under reduced pressure to give the title compound as a brown yellow oil (12.97 g, 92%). ¹H NMR (CDCl₃, 300 MHz) δ 7.59 (d, J=2.5 Hz, 1H), 7.36 (dd, J=8.5, 2.5 Hz, 1H), 7.03 (d, J=8.5 Hz, 1H), 4.60 (d, J=12.8 Hz, 1H), 4.52 (d, J=12.8 Hz, 1H), 3.44 (s, 3H), 2.96-2.81 (m, 2H), 2.51 (m, 1H), 1.77 (m, 2H), 1.64 (m, 2H), 1.50-1.30 (m, 2H), 0.79 (d, J=6.1 Hz, 3H). LC/MS (Method B): 298.1 (M+H)⁺.

Step 4: 3-(methoxymethyl)-4-(2-methylpiperidin-1-yl)benzoic acid

To anhydrous Et₂O (130 mL) at −78° C. was added tert-butyllithium (63.79 mL; 1.50 M; 95.68 mmol) (solution in pentane) which was followed by the slow addition of a solution of 1-[4-bromo-2-(methoxymethyl)phenyl]-2-methylpiperidine obtained in step 3 (12.97 g; 43.49 mmol) in anhydrous Et₂O (20 mL). After 40 min, the reaction mixture was poured on an excess of freshly crushed dry ice and stirred for 30 min after which time it was diluted with Et₂O/EtOAc (1:1), water (pH 4-5). The organic layers were combined, dried over MgSO₄ and the solvents were removed under reduced pressure to give a yellow oil that was triturated in iPr₂O and pentane, filtered off and washed with pentane to give the title compound as a beige powder. ¹H NMR (CDCl₃, 300 MHz) δ 8.22 (d, J=2.1 Hz, 1H), 8.00 (dd, J=8.3, 2.1 Hz, 1H), 7.17 (d, J=8.3 Hz, 1H), 4.60 (d, J=12.3 Hz, 1H), 4.55 (d, J=12.3 Hz, 1H), 3.46 (s, 3H), 3.17 (m, 1H), 3.02 (m, 1H), 2.63 (m, 1H), 1.88-1.65 (m, 4H), 1.55-1.40 (m, 2H), 0.88 (d, J=6.2 Hz, 3H). LC/MS (Method B): 264.1 (M+H)⁺.

Intermediate 17: 4-(2-methylpiperidin-1-yl)-3-[(methylsulfonyl)amino]benzoic acid

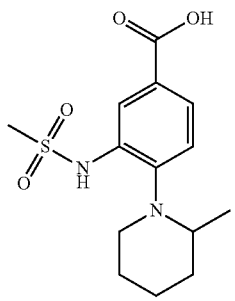

Step 1: 4-(2-methylpiperidin-1-yl)-3-nitrobenzoic acid

A mixture of ethyl 4-fluoro-3-nitrobenzoate (Chontec, 25 g; 117.28 mmol) and 2-methylpiperidine (41.54 mL; 351.84 mmol) in DMF (100 mL) was heated at 50° C. for 2 hours The reaction was cooled to RT and diluted with water (100 mL), extracted with EtOAc, dried over MgSO₄ and concentrated giving a yellow oil. The residue was taken up in THF (250 mL) and lithium hydroxide (14.04 g; 586.41 mmol) was added followed by water (250 mL). The reaction mixture was stirred at RT for 2 days. After evaporation of THF, the solution was diluted with water and washed with Et₂O. The aqueous layer was acidified to pH 5 with AcOH, extracted with Et₂O, dried over MgSO₄ and concentrated affording the title compound as a yellow solid (24.81 g, 80%). ¹H NMR (DMSO-d₆) δ 13.09 (br s, 1H), 8.23-8.22 (d, J=2.14 Hz, 1H), 8.04-8.01 (dd, J=8.72 Hz, 2.19 Hz, 1H), 7.44-7.41 (d, J=8.94 Hz, 1H), 3.63-3.61 (m, 1H), 3.22-3.18 (m, 1H), 2.89-2.85 (m, 1H), 1.78-1.44 (m, 6H), 1.06-1.04 (d, J=6.65 Hz, 3H). HPLC (Method A) Rt 3.96 min (Purity: 97.9%). LC/MS (Method B): 265.2 (M+H)⁺; 263.2 (M+H)⁻.

Step 2: Ethyl 3-amino-4-(2-methylpiperidin-1-yl)benzoate

Ethyl 4-(2-methylpiperidin-1-yl)-3-nitrobenzoate (5 g; 17.10 mmol) in a solution of MeOH/EtOAc 1:1 (340 mL, 0.05 M) was injected on a flow hydrogenation reactor (H-Cube), adapted with a Pd/C cartridge (44 mm), a flow of 1 mL/min, no heating and the full H₂ option enabled, affording after evaporation of the solvents the title compound as a white solid (4.34 g, 96%). ¹H NMR (DMSO-d₆, 300 MHz) δ 7.34-7.33 (d, 1H), 7.21-7.18 (dd, J=8.2 Hz, 1.8 Hz, 1H), 7.06-7.03 (d, J=8.1 Hz 1H), 5.09 (br s, 2H), 4.28-4.26 (q, J=7.4 Hz, 2H), 3.11-3.07 (m, 1H), 2.97-2.88 (m, 1H), 2.47-2.3 (m, 1H), 1.83-1.65 (m, 6H), 1.32 (t, J=7.4 Hz, 3H). HPLC (Method A) Rt 2.60 min (Purity: 97.8%). LC/MS (Method B): 263.2 (M+H)⁺.

Step 3: 4-(2-methylpiperidin-1-yl)-3-[(methylsulfonyl)amino]benzoic acid

Methanesulfonyl chloride (1.68 mL; 21.72 mmol) was added dropwise (addition took 5 min) to a cold (0° C.) solution of Py (10 mL) and ethyl 3-amino-4-(2-methylpiperidin-1-yl)benzoate (5.18 g; 19.74 mmol) in DCM (40 mL) and the reaction mixture was allowed to return to RT over one hour. The reaction mixture was stirred at RT for 3 hours. After this time, it was concentrated and the residue was taken up in water. The aqueous phase was extracted with EtOAc. The combined organic phases were washed with HCl (1 M) then brine, dried over MgSO₄ and concentrated giving a yellow oil. This oil was taken up in THF (30 mL) and lithium hydroxide (2.36 g; 98.72 mmol) was added, followed by water (30 mL). The resulting mixture was stirred at RT for 2 days. THF was removed under vacuum and the solution diluted with water. This solution was washed with Et₂O and acidified to pH 2 with conc HCl. The aqueous phase was extracted with EtOAc, washed with brine, dried over MgSO₄ and concentrated affording the title compound as a beige solid (5.48 g, 88%). ¹H NMR (DMSO-d₆) δ 12.98 (br s, 1H), 8.53 (br s, 1H), 8.07-8.06 (d, J=1.91 Hz, 1H), 7.77-7.73 (dd, J=8.34 Hz, 1.97 Hz, 1H), 7.47-7.45 (d, J=8.34 Hz, 1H), 3.43-2.58 (m, 6H), 1.84-1.46 (m, 6H), 0.83-0.81 (d, J=6.09 Hz, 3H). HPLC (Method A) Rt 2.29 min (Purity: 99.0%).

Intermediate 18:
5-methyl-6-(2-methylpyrrolidin-1-yl)nicotinic acid

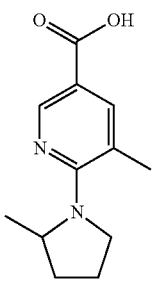

Step 1: 5-methyl-6-(2-methylpyrrolidin-1-yl)nicotinonitrile

A solution of 5-cyano-2-fluoro-3-methylpyridine (Molekula, 400 mg; 2.94 mmol) in 1-butanol (1 mL), 2-methylpyrrolidine (Acros, 300 mg; 3.53 mmol) and DIEA (1.52 mL; 8.82 mmol) was heated at 90° C. for 18 hours. Reaction mixture was partitioned between EtOAc and water and washed with water to give the title compound as a yellow oil (600 mg, quantitative). HPLC (Method A) Rt 1.99 min (Purity: 96.1%). LC/MS (Method B): 202.1 (M+H)+.

Step 2:
5-methyl-6-(2-methylpyrrolidin-1-yl)nicotinic acid

A solution of 5-methyl-6-(2-methylpyrrolidin-1-yl)nicotinonitrile obtained in step 1 (591 mg; 2.94 mmol) in water (15 mL) and KOH (823 mg; 14.68 mmol) was heated at reflux for 16 hours. Reaction mixture was basified to pH 6 and extracted with EtOAc to give the title compound as a white solid. $^1$H NMR (DMSO-d$_6$) δ 12.43 (s, 1H), 8.48 (d, J=2.2 Hz, 1H), 7.74-7.73 (m, 1H), 4.41-4.32 (m, 1H), 3.81-3.73 (m, 1H), 3.49-3.42 (m, 1H), 2.29 (s, 3H), 2.10-2.04 (m, 1H), 1.94-1.88 (m, 1H), 1.74-1.68 (m, 1H), 1.59-1.52 (m, 1H), 1.25 (d, J=6 Hz, 3H). HPLC (Method A) Rt 1.45 min (Purity: 99.8%). LC/MS (Method B): 221.2 (M+H)+.

Intermediate 19: 2,2'-dimethyl-1,1'-biphenyl-4-carboxylic acid

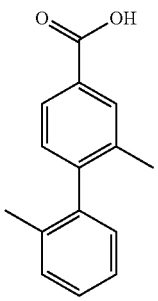

Step 1: methyl 2,2'-dimethyl-1,1'-biphenyl-4-carboxylate

To a solution of methyl 4-bromo-3-methylbenzoate (ABCR, 15 g, 65 mmol) in toluene (200 mL) and water (200 mL), was added o-tolylboronic acid (10.68 g, 78 mmol) followed by potassium carbonate (45.25 g, 32.7 mmol) and tetrakis(triphenylphosphine)palladium(0) (3.78 g, 3.3 mmol). The mixture was degassed with N$_2$ and refluxed at 120° C. for 6 hours. After the completion of reaction, the reaction mixture was cooled to RT. The organic phase was separated and evaporated under reduced pressure. The crude compound was passed through a silica column using hexane as eluent to get the title compound as a white solid (15 g, 95%). $^1$H NMR (DMSO-d$_6$, 400 MHz) δ 7.91 (s, 1H), 7.83-7.81 (m, 1H), 7.33-7.30 (m, 2H), 7.28-7.26 (m, 1H), 7.25-7.22 (m, 1H), 7.07-7.05 (m, 1H), 3.86-3.81 (s, 3H), 2.09-2 (s, 3H), 1.97-1.92 (s, 3H). HPLC (Method B), Rt: 3.01 min (purity: 98.71%).

Step 2: 2,2'-dimethyl-1,1'-biphenyl-4-carboxylic acid

To a solution of methyl 2,2'-dimethyl-1,1'-biphenyl-4-carboxylate, prepared in Step 1 (15 g, 62.2 mmol) in THF (100 mL) was added 10% sodium hydroxide (100 mL) and the mixture was heated at 100° C. overnight. THF was removed under reduced pressure and the aqueous residue was washed with EtOAc. The aqueous layer was then acidified with HCl (3 N to pH 2-3) and extracted with DCM. The organic phase was washed with water and dried over sodium sulfate and concentrated under reduced pressure to obtain get the title compound as a white solid (13.5 g, 95%). $^1$H NMR: (DMSO-d$_6$, 400 MHz) δ 12.89 (bs, 1H), 7.89 (s, 1H), 7.82-7.80 (m, 1H), 7.32-7.23 (m, 3H), 7.19-7.11 (m, 1H), 7.07-7.05 (m, 1H), 2.04 (s, 3H), 1.98 (s, 3H). LC/MS (Method A): 227.0 (M+H)$^+$. HPLC (Method B), Rt: 4.1 min (purity: 99.6%).

Intermediate 20:
4-(2-methylpiperidin-1-yl)-3-nitrobenzoic acid

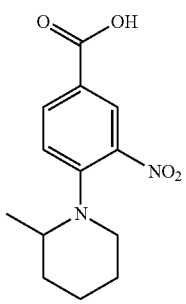 [SMILES: CC1CCCCN1c1ccc(C(=O)O)cc1[N+](=O)[O-]]

A mixture of ethyl 4-fluoro-3-nitrobenzoate (Chontech, 1 g; 4.69 mmol) and 2-methylpiperidine (1.39 g; 14.07 mmol) in DMF (4 mL) was heated to 50° C. for 3 hours. The reaction was then allowed to return to RT and diluted with water. It was extracted with EtOAc and the organic phase was dried over sodium sulfate and concentrated in vacuo, affording ethyl 4-(2-methylpiperidin-1-yl)-3-nitrobenzoate as a yellow oil. The residue was taken up in THF (10 mL) and lithium hydroxide (561.73 mg; 23.46 mmol) was added followed by water (10 mL). The reaction mixture was stirred at RT for 16 hours. It was concentrated and the residue was diluted with water and washed with Et$_2$O. The aqueous layer was acidified to pH 5 with acetic acid. It was extracted with Et$_2$O and the organic phase was dried over magnesium sulfate and concentrated, affording the title compound as a yellow solid (1.17 g, 94%). $^1$H NMR (DMSO-d$_6$) δ 13.07 (s, 1H), 8.23-8.22 (d, J=2.13 Hz, 1H), 8.04-8 (dd, J=8.96, 2.28 Hz, 1H), 7.44-7.41 (d, J=8.88 Hz, 1H), 3.64-3.60 (m, 1H), 3.25-3.17 (m, 1H), 2.90-2.84 (m, 1H), 1.82-1.43 (m, 6H), 1.06-1.04 (d, J=6.43 Hz, 3H). LC/MS (Method A): 265.0 (M+H)$^+$; 263.0 (M−H)$^−$.

Intermediate 21:
3-methoxy-4-(4-methyl-3-thienyl)benzoic acid

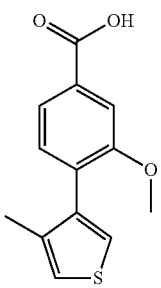

Step 1: methyl 3-methoxy-4-(4-methyl-3-thienyl)benzoate

Methyl 4-bromo-3-methoxybenzoate (Combi-Blocks, 2.50 g; 10.20 mmol) and 4-methyl-3-thiopheneboronic acid (1.59 g; 11.22 mmol), potassium carbonate (7.04 g; 51 mmol), tetrakis(triphenylphosphine)palladium(0) (1.17 g; 1.02 mmol) were mixed in toluene (10 mL) and water (10 mL) under N$_2$ atmosphere. The reaction mixture was degassed with N$_2$ for 10 min and was heated under reflux for 3 hours. The reaction mixture was cooled to RT, filtered over a pad of celite and washed with toluene. The filtrate was concentrated under vacuum to afford brown oil. It was taken in EtOAc and the organic layer was washed with a saturated aqueous solution of NaHCO$_3$, water and brine. It was dried over MgSO$_4$, filtered off and concentrated under vacuum giving a brown oil. LC/MS (Method A): 262.8 (M+1-1)$^+$. HPLC (Method A) Rt 4.79 min (Purity: 63.0%).

Step 2: 3-methoxy-4-(4-methyl-3-thienyl)benzoic acid

To a solution of methyl 3-methoxy-4-(4-methyl-3-thienyl) benzoate obtained in step 1 (2.30 g; 8.77 mmol) in EtOH (70 mL), was added at RT an aqueous solution of sodium hydroxide (5 M; 5.26 mL; 26.31 mmol). The reaction mixture was stirred at 60° C. for one hour. The reaction mixture was concentrated under vacuum to give a brown solid. It was taken up in water and the aqueous phase was washed twice with EtOAc. Aqueous phase was acidified with concentrated HCl (2 mL) to pH 2. Then it was concentrated under vacuum until a precipitate was formed (⅓ of volume). The suspension was filtered off and dried under vacuum, affording the title compound as a brown solid (1.81 g, 83% for 2 steps). $^1$H NMR: (DMSO-d$_5$) δ 13.05 (s, 1H), 7.62-7.59 (m, 2H), 7.40-7.39 (d, J=3.23 Hz, 1H), 7.32-7.29 (d, J=7.48 Hz, 1H), 7.25-7.23 (m, 1H), 3.82 (s, 3H), 2.99 (s, 3H). LC/MS (Method A): 248.8 (M+H)$^+$; 246.9 (M−H)$^−$. HPLC (Method A) Rt 3.99 min (Purity: 97.4%).

Intermediate 22:
4-(2-ethylpiperidin-1-yl)-3-(methoxymethyl)benzoic acid, hydrochloride salt

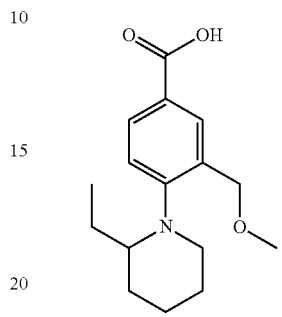

Step 1:
5-bromo-2-(2-ethylpiperidin-1-yl)benzaldehyde

To a solution of 5-bromo-2-fluorobenzaldehyde (20 g, 0.099 mol) in dimethyl sulfoxide (230 mL) and water (70 mL), were added 2-ethylpiperidine (14.4 mL, 0.1083 mol) and sodium carbonate (20.88 g, 0.197 mol). The resulting mixture was heated at 110° C. for a period of 30 h. The reaction mixture was cooled to room temperature, diluted with water (1000 mL), extracted by methyl tert-butyl ether (2×500 mL), dried using sodium sulphate and concentrated under reduced pressure. The resulting crude was purified by column chromatography on silica gel (60-120 mesh) using pet ether as eluent to afford the titled compound as a yellow liquid. $^1$H NMR (DMSO-d$_6$, 400 MHz) δ 10.15 (1H, s), 7.70-7.73 (2H, d), 7.22-7.25 (1H, m), 3.08-3.13 (2H, m), 2.84-2.86 (1H, m), 1.83-1.84 (1H, m), 1.34-1.67 (7H, m), 0.62-0.66 (3H, t).

Step 2:
[5-bromo-2-(2-ethylpiperidin-1-yl)phenyl]methanol

To a solution of 5-bromo-2-(2-ethylpiperidin-1-yl)benzaldehyde (obtained in step 1, 10 g, 0.0484 mol) in methanol (100 mL) under nitrogen, was added sodium borohydride (1.28 g, 0.0484 mol) at 0° C. in portions. After being stirred at room temperature for a period of 1 h, the reaction mixture was evaporated to remove methanol. The resulting crude product was taken in water (100 mL) and extracted in ethyl acetate. The separated organic layer was washed with water, dried over sodium sulphate and concentrated under reduced pressure to afford the titled compound as yellow liquid (8.8 g, 88%). $^1$H NMR (DMSO-d$_6$, 400 MHz) δ 7.54-7.55 (1H, s), 7.34-7.54 (1H, m), 7.07-7.09 (1H, d), 5.17-5.20 (1H, t), 4.59-4.64 (1H, d), 4.43-4.48 (1H, d), 2.77-2.84 (2H, m), 2.442-2.449 (1H, m), 1.74 (2H, t), 1.53-1.56 (2H, t), 1.32-1.34 (2H, m), 1.15-1.19 (2H, m), 0.60-0.64 (3H, t).

Step 3: 1-[4-bromo-2-(methoxymethyl)phenyl]-2-ethylpiperidine

To a solution of sodium hydride (2.3 g, 0.093 mmol) in dry DMF (130 mL) was added a solution of [5-bromo-2-(2-ethylcyclohexyl)phenyl]methanol (15 g, 0.0483 mol) in DMF (20 mL) dropwise at 0° C. After stirring the reaction mixture for 30 min, methyl iodide was added dropwise at 0° C. The reaction mixture was quenched with saturated solution of ammonium chloride in water (30 mL). It was then diluted with water (100 mL) and extracted in ethyl acetate, dried using sodium sulphate and concentrated under reduced pressure to afford the titled compound as a yellow liquid (15.2 g, 97%). $^1$H NMR (CDCl$_3$, 400 MHz) δ 7.59 (1H, s), 7.34-7.36 (1H, d), 7.01-7.03 (1H, d), 4.49-4.59 (2H, m), 3.43 (3H, s), 2.87-2.89 (1H, d), 2.75 (1H, bs), 2.51 (1H, bs), 1.79-1.86 (2H, m), 1.61-1.63 (3H, d), 1.40 (2H, m), 0.87-0.88 (2H, m), 0.60-0.80 (3H, t).

Step 4:
4-(2-ethylpiperidin-1-yl)-3-(methoxymethyl)benzoic acid, hydrochloride salt To a solution of 4-bromo-1-(2-ethylcyclohexyl)-2-(methoxymethyl)benzene (1.42 g, 4.55 mmol) in dry THF was added n-butyl lithium (2.4 mL, 6.82 mmol) dropwise at −80° C. and the mixture was stirred for 1 h. Then the reaction mixture was carefully poured onto crushed dry-ice (100 g). Once the excess carbon dioxide was liberated, the reaction mixture was acidified with 2N HCl aqueous solution. The resulting precipitate was filtered and dried, affording the title compound as an off-white solid (1000 mg; 79%). $^1$H NMR (CD3OD, 400 MHz) δ 8.19-8.21 (1H, d), 8.07 (1H, s), 7.91-7.93 (1H, d), 5.03-5.06 (2H, m), 3.89 (1H, bs), 3.65-3.72 (5H, m), 2.37-2.04 (1H, d), 2.02-2.14 (2H, m), 1.72-1.95 (3H, m), 1.43-1.49 (2H, m), 0.86-0.90 (3H, t). LC/MS (Method A): 278.0 (M−H)+. HPLC (Method A) Rt 1.97 min (Purity: 97.94%).

Intermediate 23: 2'-ethyl-2-(methoxymethyl)-1,1'-biphenyl-4-carboxylic acid

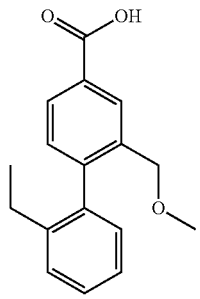 [SMILES: CCc1ccccc1-c1ccc(C(=O)O)cc1COC]

Step 1: methyl 2'-ethyl-2-(methoxymethyl)-1,1'-biphenyl-4-carboxylate

To a solution of methyl 4-bromo-3-(methoxymethyl)benzoate, (Intermediate 28, step 2) (12 g, 0.0463 mol) in toluene (150 mL) and water (35 mL) under N$_2$, was added 2-ethyl benzene boronic acid (9.02 g, 0.0601 mol) followed by potassium carbonate (19 g, 0.1389 mol) and Pd(PPh$_3$)$_4$ (2.67 g, 0.0023 mol). The reaction mixture was degassed with N$_2$ for 10 min before heating. After 12 hours at 100° C., the reaction mixture was diluted with EtOAc. The organic layer was washed with sodium bicarbonate sat. solution (1×100 mL), water (2×100 mL) and finally with brine (1×100 mL). It was then dried over sodium sulphate and concentrated under reduced pressure. The residue was purified by chromatography (silica gel, 60-120 mesh, eluting with pet ether/EtOAc) to afford the title compound as a pale yellow liquid (12 g, 83%). $^1$H NMR (CDCl$_3$, 400 MHz) δ 8.24-8.26 (1H, s), 7.99-8.01 (1H, d), 7.32-7.38 (2H, m), 7.22-7.27 (2H, m), 7.07-7.09 (1H, d), 4.12-4.21 (2H, d), 3.93-3.95 (3H, s), 3.28-3.30 (3H, s), 2.28-2.43 (2H, m), 1.01-1.05 (3H, t).

Step 2: 2'-ethyl-2-(methoxymethyl)-1,1'-biphenyl-4-carboxylic acid

To a solution of methyl 2-ethyl-2-(methoxymethyl)-1,1'-biphenyl-4-carboxylate (12 g, 0.0422 mol) in THF (150 mL) and water (30 mL), was added lithium hydroxide monohydrate (5.31 g, 0.127 mol) in portions. After 12 h at RT, the reaction mixture was concentrated and the aqueous phase was acidified using conc. HCl and extracted with EtOAc. Then the organic layers were washed with water and brine solution. The solvents were dried over sodium sulphate and concentrated under reduced pressure to afford the title compound as a white solid (9 g, 80%). $^1$H NMR (DMSO-d$_6$, 300 MHz) δ 12.9 (1H, bs), 8.08 (1H, s), 7.88-7.90 (1H, m), 7.34-7.35 (2H, m), 7.21-7.25 (2H, m), 7.03-7.05 (1H, m), 4.04-4.13 (2H, m), 3.16-3.18 (3H, s), 2.29-2.38 (1H, m), 2.19-2.24 (1H, m), 0.92-0.95 (3H, m). LC/MS (Method A): 269.0 (M−H)−. HPLC (Method B) Rt 5.06 min (Purity: 97.4%).

Intermediate 24: 2'-methyl-2-(trifluoromethyl)biphenyl-4-carboxylic acid

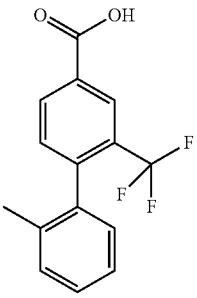 [SMILES: Cc1ccccc1-c1ccc(C(=O)O)cc1C(F)(F)F]

Step 1: methyl 4-bromo-3-(trifluoromethyl)benzoate

To a suspension of 4-bromo-3-(trifluoromethyl)benzoic acid (Acceledev 000625, 15 g; 55.76 mmol) in MeOH (300 mL) at RT was added dropwise thionyl chloride (16.18 mL; 223.04 mmol) over 15 min. The reaction mixture was stirred at RT for 12 hours. The solvent was concentrated and the crude residue was diluted with EtOAc (500 mL). The organic layer was washed with a saturated aqueous solution of NaHCO$_3$ (200 mL), water (200 mL), brine (200 mL), dried over MgSO$_4$ and concentrated affording the title compound as an orange solid (14.80 g, 94%). $^1$H NMR (DMSO-d$_6$, 300 MHz) δ 8.26 (m, 1H), 8.14-8.13 (m, 2H), 3.93 (s, 3H). HPLC (Method A) Rt 4.71 min (Purity: 99.0%).

Step 2: methyl 2'-methyl-2-(trifluoromethyl)biphenyl-4-carboxylate

Methyl 4-bromo-3-(trifluoromethyl)benzoate (6 g; 21.20 mmol; 1 eq.), o-tolylboronic acid (3.17 g; 23.32 mmol; 1.10 eq.), potassium carbonate (14.65 g; 105.99 mmol; 5 eq.), tetrakis(triphenylphosphine)palladium(0) (2.45 g; 2.12 mmol; 0.10 eq.) were taken up in toluene (30 mL) and water (30 mL) under N₂ atmosphere. The reaction mixture was purged with vacuum for 5 minutes, then degassed with N₂ and then refluxed for 3 hours. The reaction mixture was cooled to RT, filtered over a pad of celite and washed with toluene (200 mL). The filtrate was concentrated to afford brown oil which was taken in EtOAc (200 mL). The organic layer was washed with a saturated aqueous solution of NaHCO₃ solution (50 mL), water (50 mL) and brine (50 mL), dried over MgSO₄ and concentrated affording the title compound as a brown oil (6.4 g, quantitative). HPLC (Method A) Rt 5.33 min.

Step 3: 2'-methyl-2-(trifluoromethyl)biphenyl-4-carboxylic acid

A solution of methyl 2'-methyl-2-(trifluoromethyl)biphenyl-4-carboxylate (5 g; 16.99 mmol; 1 eq.) in EtOH (150 mL) at RT was treated with sodium hydroxide (10.2 mL; 5 M; 51 mmol; 3 eq.). The reaction mixture was stirred at 60° C. for 2 hours. The reaction mixture was concentrated to give a brown solid which was taken up in water (300 mL) and the aqueous phase was washed twice with EtOAc. The aqueous phase was acidified with HCl cc to pH 2, then it was concentrated until precipitation (half of the volume). The suspension was filtered affording the title compound as a beige solid. ¹H NMR (DMSO-d₆, 300 MHz) δ 13.55 (br s, 1H), 8.31 (s, 1H), 8.26-8.23 (d, J=7.90 Hz, 1H), 7.51-7.48 (d, J=7.90 Hz 1H), 7.37-7.12 (m, 4H), 1.99 (s, 3H). LC/MS (Method A): 278.9 (M−H)−. HPLC (Method A) Rt 4.57 min (Purity: 98.7%).

Intermediate 25: tert-butyl 3-[7-[amino(hydroxyimino)methyl]-3,4-dihydroisoquinolin-2(1H)-yl]propanoate

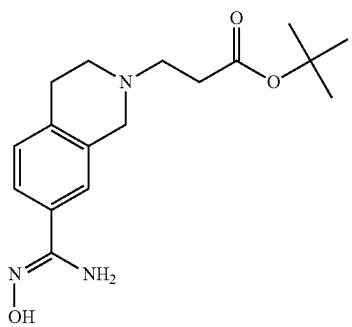 [SMILES: CC(C)(C)OC(=O)CCN1CCc2ccc(/C(N)=N/O)cc2C1]

Step 1: tert-butyl 3-(7-cyano-3,4-dihydroisoquinolin-2(1H)-yl)propanoate 7-cyano-1,2,3,4-tetrahydroisoquinoline (7 g; 44.3 mmol; 1 eq.) and potassium carbonate (10.4 g; 75.2 mmol; 1.7 eq.) were suspended in ACN (280 mL) to which was added t-butyl 3-bromopropionate (11.5 mL; 68.6 mmol; 1.05 eq.). The reaction mixture was heated to 70° C. for 24 h. Solvents were removed under vacuum and solid residue partitioned between a saturated aqueous solution of NaHCO₃ and EtOAc. Organic layers was washed with brine, dried over magnesium sulfate, filtered and concentrated to afford the title compound (11.86 g; 94%) as a yellow oil. ¹H NMR (DMSO-d₆) δ 7.57-7.54 (m, 2H), 7.32-7.29 (m, 1H), 3.59 (s, 2H), 2.87-2.83 (t, J=5.94 Hz, 2H), 2.74-2.66 (m, 4H), 2.46-2.42 (t, J=7.01 Hz, 2H), 1.39 (s, 9H). LC/MS (Method B): 287.1 (M+H)⁺. HPLC (Method A) Rt 2.37 min (Purity: 96.4%).

Step 2: tert-butyl 3-[7-[(Z)-amino(hydroxyimino)methyl]-3,4-dihydroisoquinolin-2(1H)-yl]propanoate tert-butyl 3-(7-cyano-3,4-dihydroisoquinolin-2(1H)-yl) propanoate (11.85 g; 41.38 mmol; 1 eq.), obtained in step 1 was suspended in EtOH (237 mL). Hydroxylamine (6.1 mL; 206.9 mmol; 5 eq.) was added in one portion. The reaction mixture was stirred at room temperature for 48 h. The reaction mixture was concentrated under vacuum, triturated with diisopropyl ether and concentrated under vacuum affording title compound as a yellowish solid.

1H NMR (DMSO-d6) δ 9.51 (br s, 1H), 7.43-7.34 (m, 2H), 7.09-7.06 (d, J=8.17 Hz, 1H), 5.71 (br s, 2H), 3.56 (s, 2H), 2.79-2.64 (m, 6H), 2.47-2.42 (t, J=6.93 Hz, 2H), 1.39 (s, 9H). LC/MS (Method B): 320.1 (M+H)+. HPLC (Method A) Rt 1.57 min.

Intermediate 26: 4-[(2R)-2-methylpiperidin-1-yl]-3-(trifluoromethyl)benzoic acid

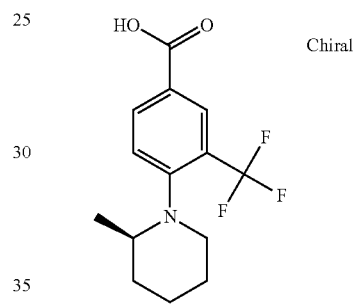

4-fluoro-3-(trifluoromethyl)benzonitrile (1 g; 5.29 mmol; 1 eq.) and (R)-(−)-2-methylpiperidine (3.1 mL; 26.4 mmol; 5 eq.) in DMSO (10 mL) were heated at 100° C. under nitrogen for 12 h. The reaction mixture was then diluted in EtOAc, washed with water, NaHCO₃ sat and NH₄Cl sat. The organic phase was dried over MgSO₄, filtered and evaporated under vacuum to give a yellow oil, that was submitted to the next step without further purification. HPLC (Method A) Rt 5.65 min. LC/MS (Method B): 269.1 (M+H)⁺.

4-[(2R)-2-methylpiperidin-1-yl]-3-(trifluoromethyl)benzonitrile (1.40 g; 5.22 mmol; 1 eq.) was dissolved in MeOH (7 mL) to which was added NaOH (5 N solution in water, 7 mL). The reaction mixture was heated to 100° C. for 7 hours. The reaction mixture was acidified to pH 2 with 5N HCl solution in water. The resulting precipitate was filtered and washed with water to give a light brown solid. It was recrystallized from Et2O/cHex to give a beige solid.

1H NMR (DMSO-d6) δ 13.29 (s, 1H), 8.23-8.12 (m, 2H), 7.68 (d, J=8.4 Hz, 1H), 3.07 (m, 1H), 2.94-2.81 (m, 1H), 2.61-2.45 (m, 2H), 1.75 (m, 1H), 1.67-1.18 (m, 4H), 0.71 (d.

J=6.1 Hz, 3H). HPLC (Method A), Rt 4.80 min (Purity: 99.9%). LC/MS (Method B): 286.2 (M+H)−; 288.0 (M+H)+.

Intermediate 27: 4-[(2S)-2-methylpiperidin-1-yl]-3-(trifluoromethyl)benzoic acid

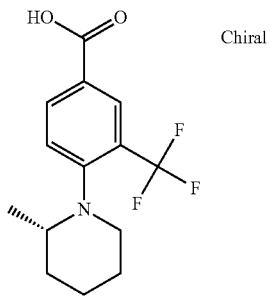 [SMILES: C[C@H]1CCCCN1c1ccc(C(=O)O)cc1C(F)(F)F]

4-fluoro-3-(trifluoromethyl)benzonitrile (1 g; 5.29 mmol; 1 eq.) and (S)-(+)-2-methylpiperidine (3.1 mL; 26.4 mmol; 5 eq.) in DMSO (10 mL) were heated at 100° C. under nitrogen for 12 h. The reaction mixture was then diluted in EtOAc, washed with water, NaHCO₃ sat and NH₄Cl sat. The organic phase was dried over MgSO₄, filtered and evaporated under vacuum to give a yellow oil, that was submitted to the next step without further purification. LC/MS (Method B): 269.0 (M+H)⁺.

4-[(2S)-2-methylpiperidin-1-yl]-3-(trifluoromethyl)benzonitrile (1.40 g; 5.22 mmol; 1 eq.) was dissolved in MeOH (7 mL) to which was added NaOH (5 N solution in water, 7 mL). The reaction mixture was heated to 100° C. for 7 hours. The reaction mixture was acidified to pH 2 with 5N HCl solution in water. The resulting precipitate was filtered and washed with water to give a light brown solid. It was recrystallized from Et₂O/cHex to give a beige solid (851 mg; 57% over 2 steps). ¹H NMR (DMSO-d₆) δ 13.29 (s, 1H), 8.23-8.12 (m, 2H), 7.68 (d, J=8.4 Hz, 1H), 3.07 (m, 1H), 2.94-2.81 (m, 1H), 2.61-2.45 (m, 2H), 1.75 (m, 1H), 1.67-1.18 (m, 4H), 0.71 (d, J=6.1 Hz, 3H). HPLC (Method A), Rt 4.79 min (Purity: 99.9%). LC/MS (Method B): 286.2 (M+H)⁻; 288.0 (M+H)⁺.

Intermediate 28: 6-[amino(hydroxyimino)methyl]-1H-indole-2-carboxylic acid

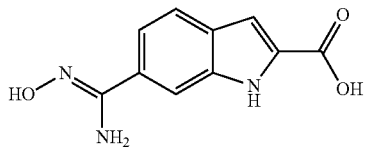 [SMILES: N/C(=N\O)c1ccc2cc(C(=O)O)[nH]c2c1]

A solution of 6-cyano-1H-indole-2-carboxylic acid (prepared according to *J. Org. Chem.* 1953, 18, 345-357, 1 g; 5.37 mmol; 1 eq.), hydroxylamine (50% in water; 1.77 mL; 26.86 mmol; 5 eq.) in EtOH (10 mL) was stirred at RT for 14 hours after which it was further heated at 60° C. for 28 hours. Solvents were removed under vacuum to give the title compound as a white powder (1.227 g; quantitative yield). ¹H NMR (DMSO-d₆) δ 11.75 (s, 1H), 7.72 (s, 1H), 7.58 (d, J=8.5 Hz, 1H), 7.37 (dd, J=1.2, 8.5 Hz, 1H), 7.00 (d, J=1.2 Hz, 1H), 5.76 (bs, 2H), 3.44 (q, J=7.1 Hz, 2H), 1.05 (t, J=7.1 Hz, 3H).

General Procedure 1:

To a suspension of intermediate Acid (1 eq.) in DCM (2 mL) and n-ethyldiisopropylamine (4 eq.) were added oxalyl chloride (3 eq.) and DMF (catalytic) and the suspension was further stirred at RT for 1 to 6 hours. The solution was then evaporated to dryness and the residue taken up in THF. This solution was then added to a solution of intermediate Amidoxime (1 eq.) and DIEA (3 eq.) in THF or ACN. The reaction mixture was heated to 150° C. for 30 minutes under microwave irradiation.

General Procedure 2:

To a solution of intermediate Acid (1.05 eq.) and n-ethyldiisopropylamine (2 eq.) in anhydrous DMF (20 V) at 0° C., was added hatu (1.05 eq.) at once. After 30 min, intermediate Amidoxime (1 eq.) was added at once and the reaction mixture stirred for 30 min to 2 hours. After this time, reaction mixture was partitioned between Et₂O and water and the organic layer was washed with brine, dried over MgSO₄, evaporated under vacuum. Residue was taken up with toluene (20 V) and pyridine (10 V) and heated at 95° C. for 18 h.

General Procedure 3:

To a solution of intermediate Acid (1.05 eq.) and n-ethyldiisopropylamine (2 eq.) in anhydrous DMF (20 V) at 0° C., was added hatu (1.05 eq.) at once. After 30 min, intermediate Amidoxime (1 eq.) was added at once and the reaction mixture stirred for 30 min to 2 hours. After this time, reaction mixture was partitioned between Et₂O and water and the organic layer was washed with brine, dried over MgSO₄, evaporated under vacuum. Residue was taken up with ACN (20 V) and DIEA (2 eq.) and heated at 150° C. for 30 min under MW irradiation.

Example 1

5-{5-[4-(2-methylpiperidin-1-yl)-3-(trifluoromethyl)phenyl]-1,2,4-oxadiazol-3-yl}-1H-benzimidazole

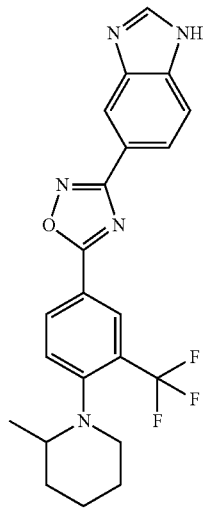 [SMILES: CC1CCCCN1c1ccc(-c2nc(-c3ccc4[nH]cnc4c3)no2)cc1C(F)(F)F]

Title compound was prepared following general procedure 1 starting from Intermediate 11 (143 mg; 0.50 mmol) Intermediate 1 (88 mg; 0.50 mmol). Reaction mixture was filtered over a SPE-NH2 column, washed with THF followed by evaporation of the solvent under reduced pressure. Evaporation of the solvent gave a yellow oil which was recrystallized in a DCM/n-pentane mixture to give the title compound as an off-white solid. ¹H NMR (DMSO, d₆) δ 12.77 (s, 1H), 8.46 (dd, J=8.4, 2.1 Hz, 1H), 8.40 (m, 2H), 8.34 (s, 1H), 7.97 (dd, J=8.5, 1.6 Hz, 1H), 7.87 (d, J=8.5 Hz, 1H), 7.78 (d, J=8.5 Hz, 1H), 3.20-3.14 (m, 1H), 2.99-2.94 (m, 1H), 2.67-2.57 (m, 1H), 1.79 (m, 2H), 1.68-1.27 (m, 4H), 0.76 (d, 6 Hz, 3H). HPLC (Method A) Rt 4.51 min (Purity: 99.4%). LC/MS (method B): 428.3 (M+H)⁺.

Example 2

5-[3-(1H-benzimidazol-5-yl)-1,2,4-oxadiazol-5-yl]-2-(2-methylpiperidin-1-yl)benzonitrile

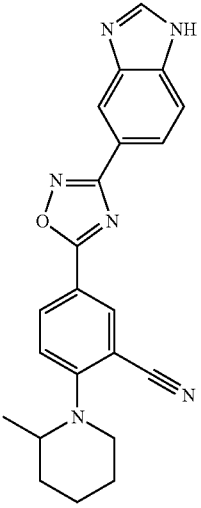 [SMILES: CC1CCCCN1c1ccc(-c2nc(-c3ccc4[nH]cnc4c3)no2)cc1C#N]

Title compound was prepared following general procedure 1 starting from Intermediate 12 (122 mg; 0.50 mmol) and Intermediate 1 (88 mg; 0.50 mmol). Reaction mixture was filtered over a SPE-NH2 column, washed with THF followed by evaporation of the solvent under reduced pressure. Reaction mixture was extracted with ethyl acetate and combined organic phase was washed with brine, dried over magnesium sulfate and concentrated in vacuo to give a yellow oily residue. Purification by silica column chromatography (DCM/MeOH, 98/2 then 95/5) afforded the title compound as an off-white solid. $^1$H NMR (DMSO, d6): δ 12.78 (s, 1H), 8.39-8.37 (m, 2H), 8.31 (s, 1H), 8.24 (dd, J=8.8, 2.2 Hz, 1H), 7.95-7.92 (m, 1H), 7.78-7.75 (m, 1H), 7.32 (d, J=8.8 Hz, 1H), 4.23-4.22 (m, 1H), 3.38-3.35 (m, 2H), 1.82-1.57 (m, 6H), 1.17 (d, 6.6 Hz, 3H). HPLC (Method A) Rt 3.65 min (Purity: 95.1%). LC/MS (method B): 358.3 (M+H)+.

Example 3

5-{5-[5-methyl-6-(2-methylpiperidin-1-yl)pyridin-3-yl]-1,2,4-oxadiazol-3-yl}-1H-benzimidazole

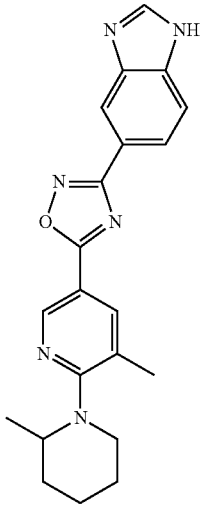 [SMILES: Cc1cc(-c2nc(-c3ccc4[nH]cnc4c3)no2)cnc1N1CCCCC1C]

Title compound was prepared following general procedure 1 starting from Intermediate 13 (120 mg; 0.51 mmol) and Intermediate 1 (90 mg; 0.51 mmol). Reaction mixture was filtered over a SPE-NH2 column, washed with THF followed by evaporation of the solvent under reduced pressure. Purification by silica column chromatography (EtOAc/c-Hex, 30/70 to 100/0) afforded the title compound as a brown powder. $^1$H NMR (DMSO, d6): δ 12.78 (s, 1H), 8.39-8.37 (m, 2H), 8.31 (s, 1H), 8.24 (dd, J=8.8, 2.2 Hz, 1H), 7.95-7.92 (m, 1H), 7.78-7.75 (m, 1H), 7.32 (d, J=8.8 Hz, 1H), 4.23-4.22 (m, 1H), 3.38-3.35 (m, 2H), 1.82-1.57 (m, 6H), 1.17 (d, 6.6 Hz, 3H). HPLC (Method A) Rt 2.71 min (Purity: 86.6%). LC/MS (method B): 358.3 (M+H)+.

Example 4

5-{5-[2-(methoxymethyl)-2'-methylbiphenyl-4-yl]-1,2,4-oxadiazol-3-yl}-1H-benzimidazole

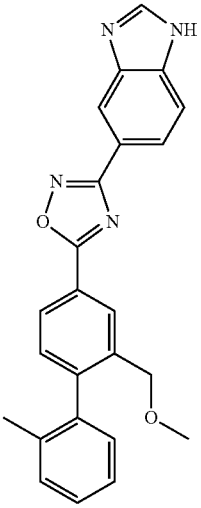

Title compound was prepared following general procedure 2 starting from intermediate 14 (807 mg; 3.15 mmol) and Intermediate 1 (528 mg; 3 mmol) The reaction mixture was diluted with Et$_2$O, washed with water and brine and evaporated under vacuum to give a beige solid. The solid was dissolved in a mixture of DCM/MeOH and filtered trough a SPE NH2 column and recrystallized from a DCM/MeOH mixture to give the title compound as a beige powder. $^1$H NMR (DMSO-d$_6$) δ 12.78 (bs, 1H), 8.40 (s, 1H), 8.34 (d, J=7 Hz, 2H), 8.19 (dd, J=7.9, 1.7 Hz, 1H), 7.99 (dd, J=8.4, 1.4 Hz, 1H), 7.78 (d, J=8.2 Hz, 1H), 7.41 (d, J=8 Hz, 1H), 7.37-7.27 (m, 3H), 7.14 (d, J=7.2 Hz, 1H), 4.24 (d, J=12.8 Hz, 1H), 4.17 (d, J=12.8 Hz, 1H), 3.26 (s, 3H), 2.04 (s, 3H). HPLC (Method A) Rt 4 min (Purity: 98.2%). LC/MS (method B): 397.2 (M+H)+.

Example 5

1-{4-[3-(1H-benzimidazol-6-yl)-1,2,4-oxadiazol-5-yl]-2'-methylbiphenyl-2-yl}-N,N-dimethylmethanamine

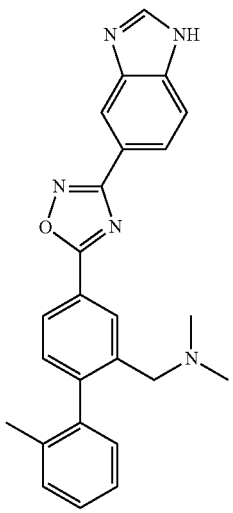

Title compound was prepared following general procedure 2 starting from intermediate 15 (160.55 mg; 0.52 mmol) and Intermediate 1 (88.09 mg; 0.50 mmol). Purification with MD-Autoprep gave the title compound as a pale yellow foam. $^1$H NMR (DMSO-d$_6$) δ 12.78 (bs, 1H), 8.40 (s, 1H), 8.34 (d, J=7 Hz, 2H), 8.19 (dd, J=7.9, 1.7 Hz, 1H), 7.99 (dd, J=8.4, 1.4 Hz, 1H), 7.78 (d, J=8.2 Hz, 1H), 7.41 (d, J=8 Hz, 1H), 7.37-7.27 (m, 3H), 7.14 (d, J=7.2 Hz, 1H), 4.24 (d, J=12.8 Hz, 1H), 4.17 (d, J=12.8 Hz, 1H), 3.26 (s, 3H), 2.04 (s, 3H). HPLC (Method A) Rt 1.84 min (Purity: 92.8%). LC/MS (method B): 410.2 (M+H)+.

Example 6

5-{5-[3-(methoxymethyl)-4-(2-methylpiperidin-1-yl)phenyl]-1,2,4-oxadiazol-3-yl}-1H-benzimidazole

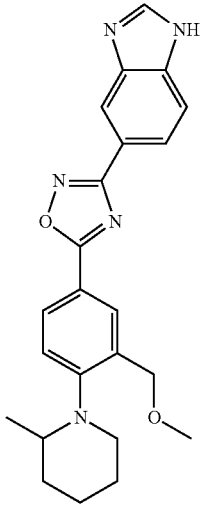

Title compound was prepared following general procedure 2 starting from intermediate 16 (316 mg; 1.20 mmol) and Intermediate 1 (211 mg; 1.20 mmol) as a beige powder. $^1$H NMR (CDCl3) δ 8.51 (s, 1H), 8.33 (d, J=2 Hz, 1H), 8.20 (s, 1H), 8.15 (dd, J=8.5, 1.6 Hz, 1H), 8.09 (dd, J=8.5, 2 Hz, 1H), 7.79 (d, J=8.5 Hz, 1H), 7.26-7.24 (m, 1H), 4.66 (d, J=12.3 Hz, 1H), 4.58 (d, J=12.3 Hz, 1H), 3.48 (s, 3H), 3.16-3.12 (m, 1H), 3.04-2.99 (m, 1H), 2.67-2.60 (m, 1H), 1.87-1.67 (m, 4H), 0.88 (d, J=6 Hz, 3H). HPLC (Method A) Rt 2.37 min (Purity: 98.4%). LC/MS (method B): 404.3 (M+H)+.

Example 7

7-fluoro-5-{5-[4-(2-methylpiperidin-1-yl)-3-(trifluoromethyl)phenyl]-1,2,4-oxadiazol-3-yl}-1H-benzimidazole

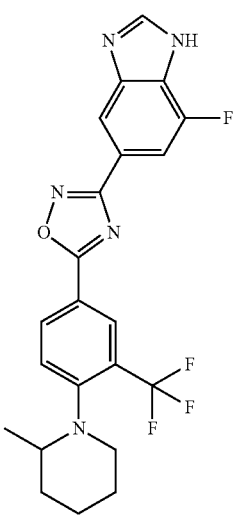 [SMILES: CC1CCCCN1c1ccc(-c2nc(-c3cc(F)c4[nH]cnc4c3)no2)cc1C(F)(F)F]

Title compound was prepared following general procedure 2 starting from intermediate 11 (344.74 mg; 1.20 mmol) and Intermediate 2 (233 mg; 1.20 mmol). Et$_2$O was added to the reaction mixture and washed with water, brine, dried over MgSO$_4$ and evaporated under reduced pressure. Purification by silica column chromatography (EtOAc/c-Hex 40:60 to 70:30) gave the title compound as a white powder. $^1$H NMR (DMSO-d$_6$) δ 13.14 (bs, 1H), 8.46-8.43 (m, 2H), 8.38 (d, J=2 Hz, 1H), 8.17 (d, J=1.1 Hz, 1H), 8.15 (dd, J=8.5, 1.6 Hz, 1H), 7.86 (d, J=8.5 Hz, 1H), 7.68 (dd, J=8.5, 1.1 Hz, 1H), 7.26-7.24 (m, 1H), 3.19-3.15 (m, 1H), 2.97-2.93 (m, 1H), 2.65-2.58 (m, 1H), 1.80-1.77 (m, 2H), 1.63-1.30 (m, 4H), 0.78 (d, J=6 Hz, 3H). HPLC (Method A) Rt 4.95 min (Purity: 99.6%). LC/MS (method B): 446.3 (M+H)+.

Example 8

7-methyl-5-{5-[4-(2-methylpiperidin-1-yl)-3-(trifluoromethyl)phenyl]-1,2,4-oxadiazol-3-yl}-1H-benzimidazole

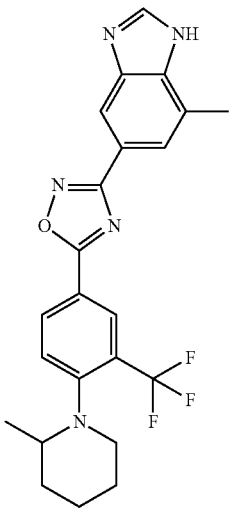

Title compound was prepared following general procedure 2 starting from intermediate 11 (344.74 mg; 1.20 mmol) and intermediate 3 (228 mg; 1.20 mmol). Et$_2$O was added to the reaction mixture and washed with water, brine, dried over MgSO$_4$ and evaporated under reduced pressure. Purification by flash chromatography (EtOAc/c-Hex 40:60 to 70:30) gave the title compound as a white powder. $^1$H NMR (DMSO-d$_6$) δ 12.80 (bs, 1H), 8.47-8.43 (m, 1H), 8.40-8.38 (m, 1H), 8.36 (s, 1H), 8.16 (bs, 1H), 7.86 (d, J=8.5 Hz, 1H), 7.76 (bs, 1H), 3.18-3.14 (m, 1H), 2.97-2.94 (m, 1H), 2.65-2.59 (m, 4H), 1.80-1.77 (m, 2H), 1.63-1.33 (m, 4H), 0.78 (d, J=6 Hz, 3H). HPLC (Method A) Rt 4.54 min (Purity: 99.9%). LC/MS (method B): 442.3 (M+H)$^+$.

Example 9

7-fluoro-5-{5-[2-(methoxymethyl)-2'-methylbiphenyl-4-yl]-1,2,4-oxadiazol-3-yl}-1H-benzimidazole

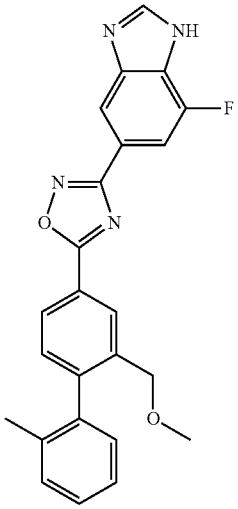 [SMILES: COCc1cc(-c2nc(-c3cc(F)c4[nH]cnc4c3)no2)ccc1-c1ccccc1C]

Title compound was prepared following general procedure 2 starting from intermediate 14 (307 mg; 1.20 mmol) and intermediate 2 (233 mg; 1.20 mmol). Et$_2$O was added to the reaction mixture and washed with water, brine, dried over MgSO$_4$ and evaporated under reduced pressure to give the title compound as a white powder. $^1$H NMR (DMSO-d$_6$) δ 13.16 (bs, 1H), 8.46 (s, 1H), 8.34 (d, J=1.2 Hz, 1H), 8.20-8.16 (m, 2H), 7.70 (dd, J=11.3, 1.2 Hz, 1H), 7.43 (d, J=8 Hz, 1H), 7.37-7.26 (m, 3H), 7.16-7.14 (m, 1H), 4.23 (d, J=12.5 Hz, 1H), 4.16 (d, J=12.5 Hz, 1H), 3.25 (s, 3H), 2.04 (s, 3H). HPLC (Method A) Rt 4.23 min (Purity: 98.6%). LC/MS (method B): 415.3 (M+H)$^+$.

Example 10

7-{5-[4-(2-methylpiperidin-1-yl)-3-(trifluoromethyl)phenyl]-1,2,4-oxadiazol-3-yl}-1,2,3,4-tetrahydroisoquinoline, Hydrochloride salt

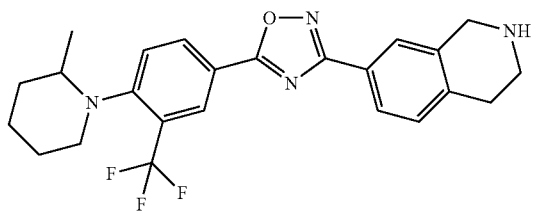 [SMILES: CC1CCCCN1c1ccc(-c2nc(-c3ccc4c(c3)CNCC4)no2)cc1C(F)(F)F]

Step 1: tert-butyl 6-{5-[4-(2-methylpiperidin-1-yl)-3-(trifluoromethyl)phenyl]-1,2,4-oxadiazol-3-yl}-3,4-dihydroisoquinoline-2(1H)-carboxylate The compound was prepared following general procedure 1 starting from intermediate 11 (143 mg; 0.50 mmol) and intermediate 4 (145 mg; 0.50 mmol). Reaction mixture was filtered over a SPE-NH2 column, washed with THF followed by evaporation of the solvent under reduced pressure to give a yellow oil. Purification by silica column chromatography (c-hexane/EtOAc, 85/15) to gave the title compound as a colourless oil. HPLC (Method A) Rt 7.19 min (Purity: 94.2%).

Step 2: 6-{5-[4-(2-methylpiperidin-1-yl)-3-(trifluoromethyl)phenyl]-1,2,4-oxadiazol-3-yl}-1,2,3,4-tetrahydroisoquinoline, Hydrochloride salt tert-butyl 6-{5-[4-(2-methylpiperidin-1-yl)-3-(trifluoromethyl)phenyl]-1,2,4-oxadiazol-3-yl}-3,4-dihydroisoquinoline-2(1H)-carboxylate obtained from step 1 was dissolved in DCM (3 mL) and TFA (1 mL). The resulting solution was stirred at RT for 1 hour and the solvent was evaporated in vacuo to give a light yellow oil. The latter was filtered through a short plug of alumina (c-hexane/EtOAc, 80/20 then 50/50) to give a light yellow oil that was triturated in a Et$_2$O/HCl (1 M) mixture (1:1, 2 mL), filtered and washed with Et$_2$O to the title compound as an off-white solid. $^1$H NMR (DMSO-d$_6$) δ 9.30 (bs, 2H), 8.45-8.41 (m, 1H), 8.38 (m, 1H), 8.01-7.98 (m, 2H), 7.86 (d, J=8.5 Hz, 1H), 7.46 (d, J=8.0 Hz, 1H), 4.41 (m, 2H), 3.54-3.42 (m, 3H), 3.18-3.08 (m, 3H), 2.97-2.93 (m, 1H), 2.65-2.59 (m, 1H), 1.80-1.77 (m, 2H), 1.63-1.30 (m, 4H), 0.78 (d, J=6 Hz, 3H). HPLC (Method A) Rt 4.61 min (Purity: 100.0%). LC/MS (method B): 443.2 (M+H)$^+$.

Example 11

N-{2-(2-methylpiperidin-1-yl)-5-[3-(1,2,3,4-tetrahydroisoquinolin-7-yl)-1,2,4-oxadiazol-5-yl]phenyl}methanesulfonamide, Hydrochloride salt

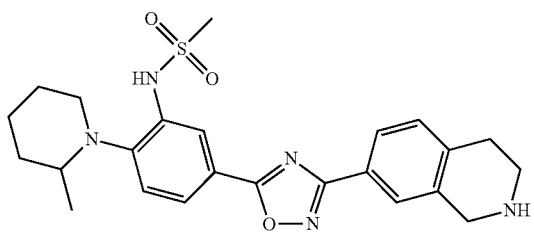 [SMILES: CC1CCCCN1c1ccc(-c2nc(-c3ccc4c(c3)CNCC4)no2)cc1NS(C)(=O)=O]

Step 1: tert-butyl 6-(5-{4-(2-methylpiperidin-1-yl)-3-[(methylsulfonyl)amino]phenyl}-1,2,4-oxadiazol-3-yl)-3,4-dihydroisoquinoline-2(1H)-carboxylate The compound was prepared following general procedure 1 starting from intermediate 17 (156 mg; 0.50 mmol) and intermediate 4 (145 mg; 0.50 mmol). Reaction mixture was filtered over a SPE-NH2 column, washed with THF followed by evaporation of the solvent under reduced pressure to give a yellow oil that was purified by silica column chromatography (c-hexane/EtOAc, 70/30) to give the title compound as a colourless sticky oil. HPLC (Method A) Rt 5.83 min (Purity: 97.3%). CL Step 2: N-{2-(2-methylpiperidin-1-yl)-5-[3-(1,2,3,4-tetrahydroisoquinolin-7-yl)-1,2,4-oxadiazol-5-yl]phenyl}methanesulfonamide, Hydrochloride salt tert-butyl 6-(5-{4-(2-methylpiperidin-1-yl)-3-[(methylsulfonyl)amino]phenyl}-1,2,4-oxadiazol-3-yl)-3,4-dihydroisoquinoline-2(1H)-carboxylate obtained from step 1 was dissolved in DCM (3 mL) and TFA (1 mL) and the resulting solution was stirred at RT for 2 hour. The solution was partitioned between EtOAc and sat. aq. NaHCO$_3$ (pH 8) and the two phases were separated. The organic phase was washed with brine, dried over sodium sulfate and concentrated in vacuo to give a colourless oil. The oil was taken up in DCM and filtered through a short plug of Alumina (DCM/MeOH, 99/1) to give a white that was taken up in MeOH (1 mL), Et$_2$O (4 mL) and HCl (1 M in Et$_2$O, 2 mL). After stirring for 10 min, the mixture was concentrated to dryness to give the title compound as an off-white solid. $^1$H NMR (DMSO-d$_6$) δ 9.58 (bs, 2H), 8.67 (bs, 1H), 8.20 (m, 1H), 7.98-7.91 (m, 3H), 7.57-7.55 (m, 1H), 7.47-7.44 (m, 1H), 4.40 (m, 2H), 3.39 (m, 2H), 3.22 (s, 3H), 3.13-3.08 (m, 3H), 2.92-2.88 (m, 1H), 2.61 (m, 1H), 1.79-1.68 (m, 4H), 1.47 (m, 2H), 0.82-0.80 (m, 3H). HPLC (Method A) Rt 3.02 min (Purity: 93.5%). LC/MS (method B): 468.4 (M+H)$^+$.

Example 12

2-(2-methylpiperidin-1-yl)-5-[3-(1,2,3,4-tetrahydroisoquinolin-7-yl)-1,2,4-oxadiazol-5-yl]benzonitrile, Hydrochloride salt

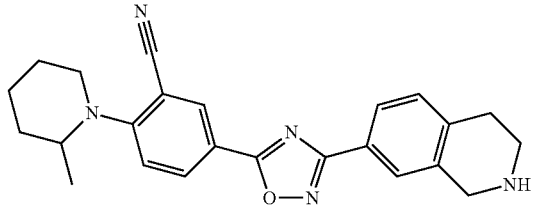 [SMILES: CC1CCCCN1c1ccc(-c2nc(-c3ccc4c(c3)CNCC4)no2)cc1C#N]

Step 1: tert-butyl 6-{5-[3-cyano-4-(2-methylpiperidin-1-yl)phenyl]-1,2,4-oxadiazol-3-yl}-3,4-dihydroisoquinoline-2(1H)-carboxylate The compound was prepared following general procedure 1 starting from intermediate 12 (122 mg; 0.50 mmol) and intermediate 4 (145 mg; 0.50 mmol). Reaction mixture was filtered over a SPE-NH2 column, washed with THF followed by evaporation of the solvent under reduced pressure and the residue purified by silica column chromatography (c-hexane/EtOAc, 80/20) to give the title compound as a white foam. HPLC (Method A) Rt 6.35 min (Purity: 94.8%).

Step 2: 2-(2-methylpiperidin-1-yl)-5-[3-(1,2,3,4-tetrahydroisoquinolin-7-yl)-1,2,4-oxadiazol-5-yl]benzonitrile, Hydrochloride salt tert-butyl 6-{5-[3-cyano-4-(2-methylpiperidin-1-yl)phenyl]-1,2,4-oxadiazol-3-yl}-3,4-dihydroisoquinoline-2(1H)-carboxylate obtained from step 1 was dissolved in DCM (3 mL) and TFA (1 mL) and the resulting solution was stirred at RT for 2 hour. The solution was partitioned between EtOAc and 0.1 M NaOH (pH 10) and the two phases were separated. The organic phase was washed with brine, dried over sodium sulfate and concentrated in vacuo to give a colourless oil that was taken up in MeOH (1 mL), Et$_2$O (4 mL) and HCl (1 M in Et$_2$O, 2 mL). After stirring for 30 min, the precipitate was filtered under inert atmosphere to give the title compound as an off-white solid. $^1$H NMR (DMSO-d$_6$) δ 9.36 (bs, 2H), 8.36 (d, J=2.2 Hz, 1H), 8.21 (dd, J=9.2, 2 Hz, 1H), 7.98-7.95 (m, 2H), 7.45 (d, J=8 Hz, 1H), 7.32 (d, J=9 Hz, 1H), 4.40 (m, 2H), 4.25 (m, 1H), 3.40-3.29 (m, 4H), 3.09 (m, 2H), 1.80-1.57 (m, 6H), 1.18 (d, J=6.6 Hz, 3H). HPLC (Method A) Rt 3.81 min (Purity: 95.0%). LC/MS (method A): 400.3 (M+H)$^+$.

Example 13 tert-butyl 7-{5-[5-methyl-6-(2-methylpyrrolidin-1-yl)pyridin-3-yl]-1,2,4-oxadiazol-3-yl}-3,4-dihydroisoquinoline-2(1H)-carboxylate

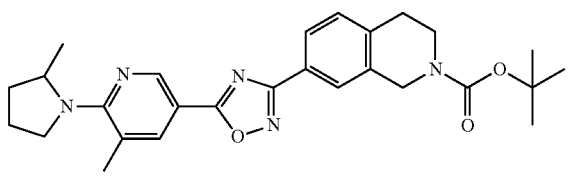 [SMILES: Cc1cc(-c2nc(-c3ccc4c(c3)CN(C(=O)OC(C)(C)C)CC4)no2)cnc1N1CCCC1C]

Title compound was prepared following general procedure 1 starting from intermediate 18 (120 mg; 0.54 mmol) and intermediate 4 (158 mg; 0.54 mmol). Reaction mixture was filtered over a SPE-NH2 column, washed with THF followed by evaporation of the solvent under reduced pressure to give a brown oil. Purification by silica column chromatography (c-hexane/EtOAc, from 60/40 to 100/0) to give the title compound as a yellow foam (212 mg, 82%). $^1$H NMR (DMSO-$d_6$) δ 8.72 (m, 1H), 8-7.99 (m, 1H), 7.87-7.84 (m, 2H), 7.38-7.36 (m, 1H), 4.61 (m, 2H), 4.46-4.40 (m, 1H), 3.86-3.80 (m, 1H), 3.61-3.57 (m, 3H), 2.88-2.84 (m, 2H), 2.40 (s, 3H), 2.14-2.01 (m, 1H), 1.98-1.94 (m, 1H), 1.82-1.73 (m, 1H), 1.64-1.57 (m, 1H), 1.44 (s, 9H), 1.17 (d, J=6.6 Hz, 3H). HPLC (Method A) Rt 4.43 min (Purity: 94.3%). LC/MS (method B): 476.4 (M+H)$^+$.

Example 14

7-{5-[5-methyl-6-(2-methylpyrrolidin-1-yl)pyridin-3-yl]-1,2,4-oxadiazol-3-yl}-1,2,3,4-tetrahydroisoquinoline

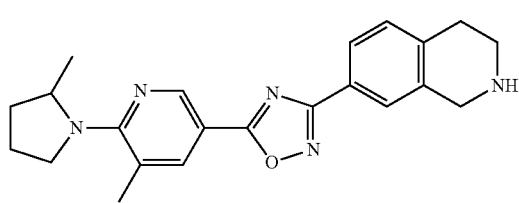 [SMILES: Cc1cc(-c2nc(-c3ccc4c(c3)CNCC4)no2)cnc1N1CCCC1C]

To a solution of example 14 (196 mg; 0.41 mmol) in DCM (10 mL), TFA (1.27 mL; 16.48 mmol) was added dropwise at 0° C. and was let to return to RT. After 18 hours, the solution was partitioned between DCM and 1 M NaOH (pH 10) and the two phases were separated. The organic phase was washed with brine, dried over sodium sulfate and concentrated in vacuo to give a yellow oil that was taken up in Et$_2$O (4 mL) and HCl (1 M in Et$_2$O, 2 mL). After stirring for 30 min, the precipitate was filtered to give the title compound as a white precipitate. HPLC (Method A) Rt 2.01 min (Purity: 92.5%). LC/MS (method B): 376.4 (M+H)$^+$.

Example 15

7-{5-[2-(methoxymethyl)-2'-methylbiphenyl-4-yl]-1,2,4-oxadiazol-3-yl}-1,2,3,4-tetrahydroisoquinoline, Hydrochloride salt

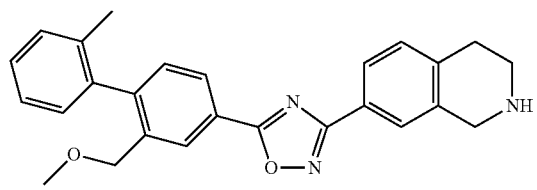 [SMILES: COCc1cc(-c2nc(-c3ccc4c(c3)CNCC4)no2)ccc1-c1ccccc1C]

The compound was prepared following general procedure 3 starting from intermediate 14 (140 mg; 0.55 mmol) and intermediate 4 (159 mg; 0.55 mmol). Solvents were removed under vacuum and the solid residue triturated in ACN, filtered. Compound was purified by MD-autoprep. and dissolved in HCl in dioxane (4M, 2 mL) and stirred at RT for 18 h after which solvents were removed under vacuum, triturated in Et$_2$O, filtered and dried under vacuum to give the title compound as a white solid. $^1$H NMR (DMSO-$d_6$) δ 9.40 (bs, 2H), 8.32 (m, 1H), 8.17-8.15 (m, 1H), 8.02-8 (m, 2H), 7.49-7.28 (m, 5H), 7.15-7.13 (m, 1H), 4.42 (bs, 2H), 4.20-4.18 (m, 2H), 3.42 (m, 2H), 3.25 (bs, 3H), 3.11 (bs, 2H), 2.03 (bs, 3H). HPLC (Method A) Rt 4.11 min (Purity: 98.6%). LC/MS (method B): 412.3 (M+H)$^+$.

Example 16

[7-{5-[2-(methoxymethyl)-2'-methylbiphenyl-4-yl]-1,2,4-oxadiazol-3-yl}-3,4-dihydroisoquinolin-2(1H)-yl]acetic acid, Hydrochloride salt

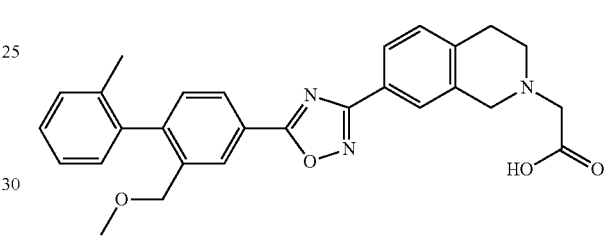

Step 1: tert-butyl [7-{5-[2-(methoxymethyl)-2'-methylbiphenyl-4-yl]-1,2,4-oxadiazol-3-yl}-3,4-dihydroisoquinolin-2(1H)-yl]acetate The compound was prepared following general procedure 3 starting from intermediate 14 (230 mg; 0.65 mmol) and intermediate 5 (200 mg; 0.65 mmol). Reaction mixture was concentrated under vacuum, dissolved in DCM and purified by silica column chromatography (EtOAc/c-Hex from 10/90 to 80/20). LC/MS (method B): 526.3 (M+H)$^+$.

Step 2: [7-{5-[2-(methoxymethyl)-2'-methylbiphenyl-4-yl]-1,2,4-oxadiazol-3-yl}-3,4-dihydroisoquinolin-2(1H)-yl]acetic acid, Hydrochloride salt tert-butyl [7-{5-[2-(methoxymethyl)-2'-methylbiphenyl-4-yl]-1,2,4-oxadiazol-3-yl}-3,4-dihydroisoquinolin-2(1H)-yl]acetate obtained from step 1 was dissolved in HCl in dioxane (4M, 10 mL), stirred at rt for 30 hours. Solvents were removed under vacuum, Et$_2$O added and the solid residue filtered after which solid was triturated in hot CH$_3$CN and filtered to give the title compound as a light green powder. $^1$H NMR (DMSO-$d_6$) δ 8.32 (m, 1H), 8.17-8.15 (m, 1H), 8.04-8 (m, 2H), 7.49 (d, J=8.1 Hz, 1H), 7.42 (d, J=7.8 Hz, 1H), 7.36-7.27 (m, 3H), 7.15-7.13 (m, 1H), 4.60 (bs, 2H), 4.24-4.13 (m, 4H), 3.60 (bs, 2H), 3.25-3.22 (m, 5H), 2.03 (s, 3H). HPLC (Method A) Rt 4.47 min (Purity: 93.4%). LC/MS (method B): 470.3 (M+H)$^+$.

Example 17

5-[5-(2,2'-dimethylbiphenyl-4-yl)-1,2,4-oxadiazol-3-yl]-1-methyl-1H-indole

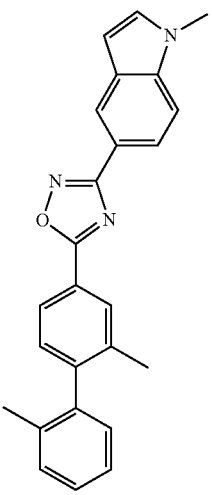

Title compound was prepared following general procedure 1 starting from intermediate 6 (94.61 mg; 0.50 mmol) and intermediate 19 (113.14 mg; 0.50 mmol). Reaction mixture was filtered over a SPE-NH2 column, washed with THF followed by evaporation of the solvent under reduced pressure. Purification by silica column chromatography (c-Hexane/EtOAc, 90/10) gave a colourless oil which was crystallised in n-Hexane to give the title compound as a white solid. HPLC (Method A) Rt 6.23 min (Purity: 99.5%). LC/MS (method A): 380.0 (M+H)$^+$.

Example 18

{5-[5-(2,2'-dimethylbiphenyl-4-yl)-1,2,4-oxadiazol-3-yl]-1H-indol-1-yl}acetic acid

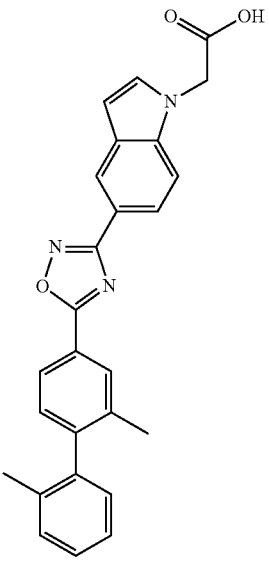 [SMILES: Cc1ccccc1-c1ccc(-c2nc(-c3ccc4c(ccn4CC(=O)O)c3)no2)cc1C]

Step 1: tert-butyl {5-[5-(2,2'-dimethylbiphenyl-4-yl)-1,2,4-oxadiazol-3-yl]-1H-indol-1-yl}acetate The compound was prepared following general procedure 1 starting from intermediate 7 (144 mg; 0.50 mmol) and intermediate 19 (113 mg; 0.50 mmol). Reaction mixture was filtered over a SPE-NH2 column, washed with THF followed by evaporation of the solvent under reduced pressure. Purification by silica column chromatography (c-Hexane/EtOAc, 90/10) gave the title compound as a colourless oil. HPLC (Method A) Rt 6.68 min (Purity: 98.5%). LC/MS (method A): 480.1 (M+H)$^+$.

Step 2: {5-[5-(2,2'-dimethylbiphenyl-4-yl)-1,2,4-oxadiazol-3-yl]-1H-indol-1-yl}acetic acid tert-butyl {5-[5-(2,2'-dimethylbiphenyl-4-yl)-1,2,4-oxadiazol-3-yl]-1H-indol-1-yl}acetate obtained in step 1 was taken up in DCM (2 mL) and TFA (0.50 ml) was added at 0° C. and allowed to return to RT. After 6 hours, solvents were evaporated under vacuum to give a light yellow oil. Purification by silica column chromatography (c-Hexane/EtOAc, 85/15 then 50/50+1% AcOH) gave a colourless oil which was triturated in a mixture of Et$_2$O and n-Hexane to give the title compound as an off-white solid. HPLC (Method A) Rt 5.41 min (Purity: 97.1%). LC/MS (method A): 422.0 (M−H)$^−$.

Example 19

1-methyl-5-{5-[4-(2-methylpiperidin-1-yl)-3-nitrophenyl]-1,2,4-oxadiazol-3-yl}-1H-indole

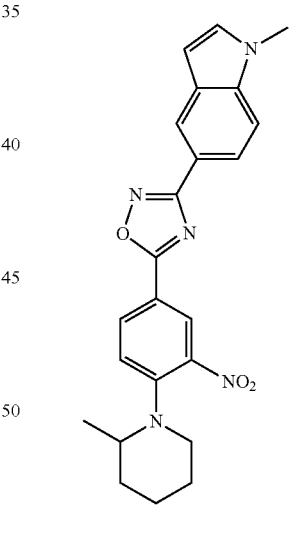

Title compound was prepared following general procedure 1 starting from intermediate 6 (94 mg; 0.50 mmol) and intermediate 20 (132 mg; 0.50 mmol). Reaction mixture was filtered over a SPE-NH2 column, washed with THF followed by evaporation of the solvent under reduced pressure. Purification by silica column chromatography (c-Hexane/EtOAc, 90/10) gave an orange oil which was triturated in n-Hexane to give the title compound as an orange solid. HPLC (Method A) Rt 5.91 min (Purity: 96.8%). LC/MS (method A): 418.1 (M−H)$^−$.

Example 20 ethyl 6-methoxy-5-{5-[4-(2-methylpiperidin-1-yl)-3-(trifluoromethyl)phenyl]-1,2,4-oxadiazol-3-yl}-1H-indole-2-carboxylate

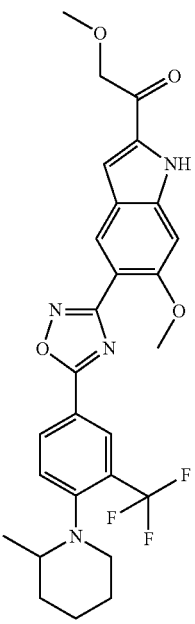 [SMILES: COCC(=O)c1cc2cc(-c3noc(-c4ccc(N5CCCCC5C)c(C(F)(F)F)c4)n3)c(OC)cc2[nH]1]

The compound was prepared following general procedure 1 starting from intermediate 8 (130 mg; 0.47 mmol) and intermediate 11 (143 mg; 0.50 mmol). Reaction mixture was filtered over a SPE-NH2 column, washed with THF followed by evaporation of the solvent under reduced pressure. Evaporation of the solvent gave a beige solid which was successively washed with n-pentane, 25% DCM in pentane and a small amount of MeOH to give the title compound as an off-white solid. HPLC (Method A) Rt 6.31 min (Purity: 99.2%). LC/MS (method A): 529.3 (M+H)$^+$.

Example 21

6-methoxy-5-{5-[4-(2-methylpiperidin-1-yl)-3-(trifluoromethyl)phenyl]-1,2,4-oxadiazol-3-yl}-1H-indole-2-carboxylic acid

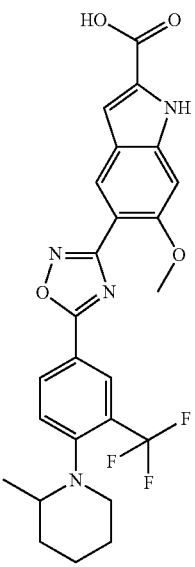 [SMILES: COc1cc2[nH]c(C(=O)O)cc2cc1-c1noc(-c2ccc(N3CCCCC3C)c(C(F)(F)F)c2)n1]

To a solution of example 20 (71 mg; 0.13 mmol) in THF (4.5 mL) was added lithium hydroxide (16 mg; 0.67 mmol) (1.50 ml), followed by water (2 mL) and the resulting mixture was stirred at RT for 24 hours. The solution was diluted with NaOH (0.1 M) washed with Et$_2$O and acidified to pH 1 with 1M HCl (1 M). The formed precipitate was filtered, washed with water and dried under high vacuum to give the title compound as an off-white solid (56 mg, 83%). $^1$H NMR (DMSO-d$_6$) δ 12.97 (bs, 1H), 11.86 (bs, 1H), 8.45-8.41 (m, 1H), 8.37-8.36 (m, 1H), 8.31 (s, 1H), 7.85 (d, J=8.4 Hz, 1H), 7.20 (m, 1H), 7.06 (m, 1H), 3.90 (s, 1H), 3.15 (m, 1H), 2.97-2.93 (m, 1H), 2.64-2.57 (m, 1H), 1.80-1.76 (m, 2H), 1.63-1.29 (m, 4H), 0.78 (d, J=6 Hz, 3H). HPLC (Method A) Rt 5.43 min (Purity: 99.1%). LC/MS (method A): 501.3 (M+H)$^+$.

Example 22

N-[5-[3-(1H-indol-5-yl)-1,2,4-oxadiazol-5-yl]-2-(2-methylpiperidin-1-yl)phenyl]methanesulfonamide

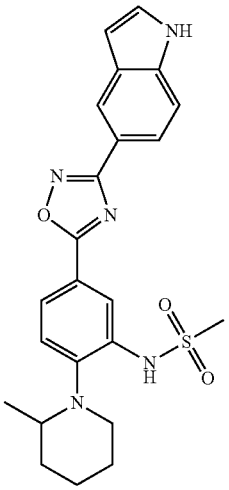

Title compound was prepared following general procedure 1 starting from intermediate 9 (87 mg; 0.47 mmol) and intermediate 17 (156 mg; 0.50 mmol). Reaction mixture was filtered over a SPE-NH2 column, washed with THF followed by evaporation of the solvent under reduced pressure. Purification by silica column chromatography (c-hexane/EtOAc, 60/40) gave a yellow sticky oil that was triturated in a of DCM/n-pentane mixture and filtered to give the title compound as a yellow solid. $^1$H NMR (DMSO-d$_6$) δ 11.45 (bs, 1H), 8.65 (s, 1H), 8.35 (m, 1H), 8.22 (d, J=1.8 Hz, 1H), 7.93 (dd, J=8.2, 1.8 Hz, 1H), 7.82 (dd, J=8.4, 1.6 Hz, 1H), 7.58-7.54 (m, 2H), 7.48-7.47 (m, 1H), 6.63 (bs, 1H), 3.23 (bs, 1H), 3.13 (m, 1H), 2.91-2.98 (m, 1H), 2.63-2.58 (m, 1H), 1.78-1.68 (m, 4H), 1.49-1.44 (m, 2H), 0.81 (d, J=6 Hz, 3H). HPLC (Method A) Rt 4.72 min (Purity: 92.6%). LC/MS (method A): 452.3 (M+H)$^+$.

Example 23

5-[3-(1H-indol-5-yl)-1,2,4-oxadiazol-5-yl]-2-(2-methylpiperidin-1-yl)benzonitrile

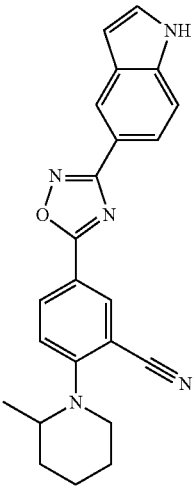 [SMILES: CC1CCCCN1c1ccc(-c2nc(-c3ccc4[nH]ccc4c3)no2)cc1C#N]

Title compound was prepared following general procedure 1 starting from intermediate 9 (87 mg; 0.47 mmol) and intermediate 12 (122 mg; 0.50 mmol). Reaction mixture was filtered over a SPE-NH2 column, washed with THF followed by evaporation of the solvent under reduced pressure. Purification by silica column chromatography (c-hexane/EtOAc, 70/43) gave a white solid that was recrystallised from EtOAc/n-pentane to afford the title compound as a white solid. $^1$H NMR (DMSO-$d_6$) δ 11.45 (bs, 1H), 8.36-8.34 (m, 2H), 8.23 (dd, J=8.9, 2.3 Hz, 1H), 7.81 (dd, J=8.5, 1.5 Hz, 1H), 7.56 (d, J=8.5, 1H), 7.48-7.46 (m, 1H), 7.32 (d, J=9 Hz, 1H), 6.60 (bs, 1H), 4.22 (m, 1H), 3.37 (m, 2H), 1.82-1.56 (m, 6H), 1.16 (d, J=6.6 Hz, 3H). HPLC (Method A) Rt 5.30 min (Purity: 95.8%). LC/MS (method B): 382.3 (M−H).

Example 24

5-{5-[3-methoxy-4-(4-methyl-3-thienyl)phenyl]-1,2,4-oxadiazol-3-yl}-1H-indazole

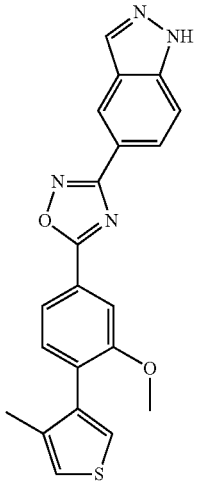 [SMILES: COc1cc(-c2nc(-c3ccc4[nH]ncc4c3)no2)ccc1-c1cscc1C]

Title compound was prepared following general procedure 1 starting from intermediate 10 (120 mg; 0.48 mmol) and intermediate 21 (85 mg; 0.48 mmol). Reaction mixture was filtered over a SPE-NH2 column, washed with THF followed by evaporation of the solvent under reduced pressure. Solid residue was dissolved in DCM and precipitated by addition of pentane which after filtration gave the title compound as a white solid. HPLC (Method A) Rt 5.16 min (Purity: 88.0%). LC/MS (method B): 387.3 (M−H)⁻.

Example 25

5-[5-(2,2'-dimethylbiphenyl-4-yl)-1,2,4-oxadiazol-3-yl]-1H-indazole

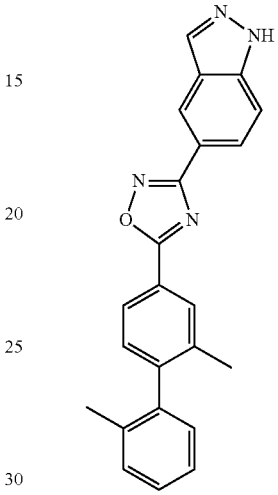

Title compound was prepared following general procedure 1 starting from intermediate 10 (93 mg; 0.53 mmol) and intermediate 19 (120 mg; 0.53 mmol). Reaction mixture was filtered over a SPE-NH2 column, washed with THF followed by evaporation of the solvent under reduced pressure. Solid residue was dissolved in DCM and precipitated by addition of pentane which after filtration gave the title compound as a white solid. $^1$H NMR (DMSO-$d_6$) δ 13.41 (bs, 1H), 8.61 (m, 1H), 8.29 (m, 1H), 8.18 (m, 1H), 8.10-8.05 (m, 2H), 7.76-7.73 (m, 1H), 7.39-7.29 (m, 4H), 7.15-7.12 (m, 1H), 2.14 (s, 3H), 2.04 (s, 3H). HPLC (Method A) Rt 5.41 min (Purity: 89.3%). LC/MS (method B): 365.4 (M−H)⁻.

Example 26

5-{5-[2-(methoxymethyl)-2'-methylbiphenyl-4-yl]-1,2,4-oxadiazol-3-yl}-7-methyl-1H-benzimidazole

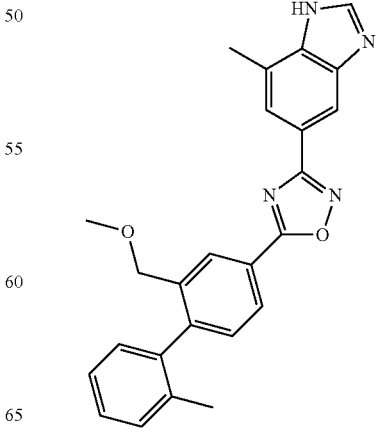

Title compound was prepared following general procedure 2 starting from Intermediate 14 (308 mg; 1.2 mmol) and Intermediate 3 (228 mg; 1.2 mmol). The reaction mixture was diluted with Et₂O, washed with water and brine and evaporated under vacuum. Purification by silica column chromatography (EtOAc/c-Hex, 30/70 to 70/30) afforded the title compound as a pink powder. $^1$H NMR (DMSO-d$_6$) δ 12.92 (br s, 0.5H), 12.71 (br s, 0.5H), 8.38 (d, J=6.0 Hz, 1H), 8.34 (d, J=1.3 Hz, 1H), 8.26-8.12 (m, 2H), 7.80 (d, J=6.8 Hz, 1H), 7.43 (d, J=8.1 Hz, 1H), 7.39-7.25 (m, 3H), 7.16 (d, J=7.0 Hz, 1H), 4.27-4.14 (m, 2H), 3.26 (s, 3H), 2.65 (s, 1.5H), 2.62 (s, 1.5H), 2.05 (s, 3H). LC/MS (method B): 409.3 (M−H)⁻; 411.3 (M+H)⁺. HPLC (Method A) Rt 4.11 min (Purity: 100.0%).

Example 27

5-{5-[4-(2-ethylpiperidin-1-yl)-3-(methoxymethyl)phenyl]-1,2,4-oxadiazol-3-yl}-1H-benzimidazole

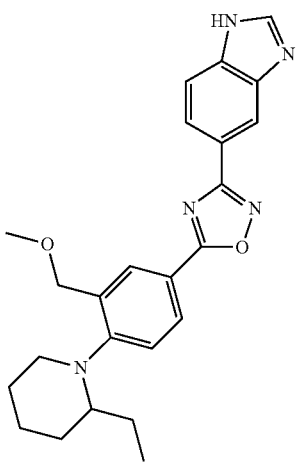 [SMILES: CCC1CCCCN1c1ccc(-c2nc(-c3ccc4[nH]cnc4c3)no2)cc1COC]

Title compound was prepared following general procedure 2 starting from intermediate 22 (377 mg; 1.2 mmol) and Intermediate 1 (211 mg; 1.2 mmol). The reaction mixture was diluted with Et₂O, washed with water and brine and evaporated under vacuum. Purification by silica column chromatography (EtOAc/c-Hex, 50/50 to 80/20) afforded the title compound as a white powder. $^1$H NMR (DMSO-d$_6$) δ 12.76 (br s, 1H), 8.39 (s, 1H), 8.32 (s, 1H), 8.19 (d, J=2.1 Hz, 1H), 8.07 (dd, J=8.4, 2.2 Hz, 1H), 7.95 (dd, J=8.4, 1.5 Hz, 1H), 7.7 (d, J=8.4 Hz, 1H), 7.36 (d, J=8.5 Hz, 1H), 4.55 (s, 2H), 3.42 (s, 3H), 3.14-3.03 (m, 2H), 2.75-2.64 (m, 1H), 1.90-1.26 (m, 8H), 0.69 (t, J=7.4 Hz, 3H). LC/MS (method B): 416.4 (M−H)⁻; 418.4 (M+H)⁺. HPLC (Method A) Rt 2.72 min (Purity: 100.0%).

Example 28

5-{5-[4-[(2R)-2-methylpiperidin-1-yl]-3-(trifluoromethyl)phenyl]-1,2,4-oxadiazol-3-yl}-1H-benzimidazole

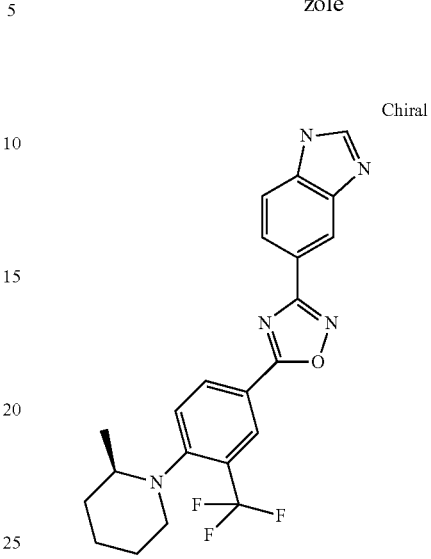

Title compound was prepared following general procedure 3 starting from Intermediate 26 (300 mg; 1.04 mmol; 1 eq.), and Intermediate 1 (183.98 mg; 1.04 mmol; 1 eq.). After evaporation of the solvents, the solid residue was triturated with ACN, filtered and dried under vacuum to give the title compound as an off-white solid. $^1$H NMR (DMSO-d$_5$) δ 12.78 (br m, 1H), 8.50-8.26 (m, 2H), 8.04-7.68 (m, 3H), 3.16 (m, 1H), 3.02-2.90 (m, 1H), 2.69-2.55 (m, 1H), 1.87-1.20 (m, 6H), 0.78 (d, J=6.1 Hz, 3H). HPLC (Method A), Rt 5.03 min (Purity: 98.4%). LC/MS (Method B): 426.3 (M+H)⁻; 428.1 (M+H)⁺.

Example 29

5-{5-[4-[(2S)-2-methylpiperidin-1-yl]-3-(trifluoromethyl)phenyl]-1,2,4-oxadiazol-3-yl}-1H-benzimidazole

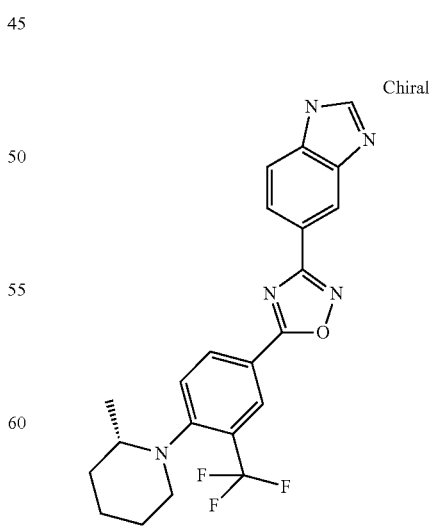

Title compound was prepared following general procedure 3 starting from Intermediate 27 (300 mg; 1.04 mmol; 1 eq.), and Intermediate 1 (183.98 mg; 1.04 mmol; 1 eq.). After evaporation of the solvents, the solid residue was triturated with ACN, filtered and dried under vacuum to give the title compound as an off-white solid. $^1$H NMR (DMSO-$d_5$) δ 12.78 (br m, 1H), 8.50-8.26 (m, 2H), 8.04-7.68 (m, 3H), 3.16 (m, 1H), 3.02-2.90 (m, 1H), 2.69-2.55 (m, 1H), 1.87-1.20 (m, 6H), 0.78 (d, J=6.1 Hz, 3H). HPLC (Method A), Rt 5.04 min (Purity: 98.4%). LC/MS (Method B): 426.3 (M+H)$^-$; 428.1 (M+1-1)$^+$.

Example 30

[7-{5-[2'-ethyl-2-(methoxymethyl)biphenyl-4-yl]-1,2,4-oxadiazol-3-yl}-3,4-dihydroisoquinolin-2(1H)-yl]acetic acid

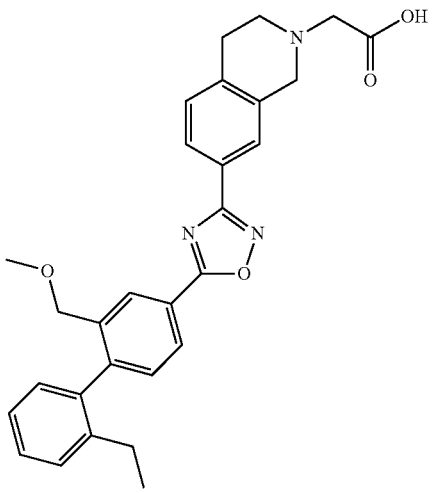 [SMILES: CCc1ccccc1-c1ccc(-c2nc(-c3ccc4c(c3)CN(CC(=O)O)CC4)no2)cc1COC]

Step 1: tert-butyl [7-{5-[2'-ethyl-2-(methoxymethyl)biphenyl-4-yl]-1,2,4-oxadiazol-3-yl}-3,4-dihydroisoquinolin-2(1H)-yl]acetate Title compound was prepared following general procedure 2 starting from Intermediate 23 (162 mg; 0.6 mmol) and Intermediate 5 (174 mg; 0.6 mmol). The reaction mixture was diluted with EtOAc, washed with water and brine and evaporated under vacuum. Purification by silica column chromatography (c-Hex/(DCM/EtOAc 1:1), 90/10 to 50/50) afforded the title compound as a yellowish oil. LC/MS (method B): 541.4 (M+H)$^+$. HPLC (Method A) Rt 4.90 min (Purity: 96.1%).

Step 2: [7-{5-[2'-ethyl-2-(methoxymethyl)biphenyl-4-yl]-1,2,4-oxadiazol-3-yl}-3,4-dihydroisoquinolin-2(1H)-yl]acetic acid tert-Butyl [7-{5-[2'-ethyl-2-(methoxymethyl)biphenyl-4-yl]-1,2,4-oxadiazol-3-yl}-3,4-dihydroisoquinolin-2(1H)-yl]acetate, obtained from step 1 (135 mg; 0.25 mmol; 1 eq.) was dissolved in hydrogen chloride in dioxane (3.13 mL; 4 M; 12.5 mmol; 50 eq.). The mixture was stirred at room temperature overnight. Solvent were removed. The solid residue was triturated with ACN, filtered and dried under vacuum to give the title compound as a white solid (93 mg, 72%). $^1$H NMR (DMSO-$d_6$) δ 8.33 (d, J=1.5 Hz, 1H), 8.16 (dd, J=8.0, 1.9 Hz, 1H), 8.06-7.99 (m, 2H), 7.49 (d, J=8.0 Hz, 1H), 7.45 (d, J=8.0 Hz, 1H), 7.41 (s, 1H), 7.40 (s, 1H), 7.34-7.27 (m, 1H), 7.12 (d, J=7.5 Hz, 1H), 4.61 (s, 2H), 4.27-4.11 (m, 4H), 3.60 (s, 2H), 3.28-3.19 (m, 5H), 2.48-2.23 (m, 2H), 0.99 (t, J=7.5 Hz, 3H). LC/MS (method B): 484.0 (M–H)$^-$; 482.1 (M+H)$^+$. HPLC (Method A) Rt 4.25 min (Purity: 98.5%).

Example 31

3-[7-{5-[2'-ethyl-2-(methoxymethyl)biphenyl-4-yl]-1,2,4-oxadiazol-3-yl}-3,4-dihydroisoquinolin-2(1H)-yl]propanoic acid

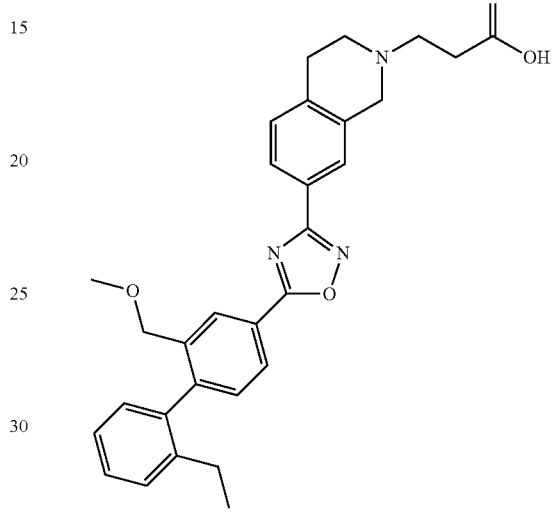

Step 1: tert-butyl 3-[7-{5-[2'-ethyl-2-(methoxymethyl)biphenyl-4-yl]-1,2,4-oxadiazol-3-yl}-3,4-dihydroisoquinolin-2(1H)-yl]propanoate Title compound was prepared following general procedure 2 starting from Intermediate 23 (162 mg; 0.6 mmol) and Intermediate 25 (182 mg; 0.6 mmol). The reaction mixture was diluted with EtOAc, washed with water and brine and evaporated under vacuum. Purification by silica column chromatography (c-Hex/(DCM/EtOAc 1:1), 90/10 to 50/50) afforded the title compound as a yellowish oil. LC/MS (method B): 555.5 (M+H)$^+$. HPLC (Method A) Rt 4.98 min.

Step 2: 3-[7-{5-[2'-ethyl-2-(methoxymethyl)biphenyl-4-yl]-1,2,4-oxadiazol-3-yl}-3,4-dihydroisoquinolin-2(1H)-yl]propanoic acid tert-butyl 3-[7-{5-[2'-ethyl-2-(methoxymethyl)biphenyl-4-yl]-1,2,4-oxadiazol-3-yl}-3,4-dihydroisoquinolin-2(1H)-yl]propanoate, obtained from step 1 (183.8 mg; 0.33 mmol; 1 eq.) was dissolved in hydrogen chloride in dioxane (4.15 mL; 4 M; 16.6 mmol; 50 eq.). The mixture was stirred at room temperature overnight. Solvent were removed. Purification with MD-Autoprep afforded the title compound as a white powder. $^1$H NMR (DMSO-$d_6$) δ 12.76 (br s, 1H), 10.85 (br s, 1H), 8.33 (d, J=1.5 Hz, 1H), 8.16 (dd, J=7.9, 1.9 Hz, 1H), 8.04 (dd, J=8.0, 1.6 Hz, 1H), 8.01-7.99 (m, 1H), 7.51 (d, J=8.1 Hz, 1H), 7.45 (d, J=8.0 Hz, 1H), 7.41 (s, 1H), 7.40 (s, 1H), 7.34-7.27 (m, 1H), 7.12 (d, J=7.3 Hz, 1H), 4.60 (br s, 2H), 4.24 (d, J=13.0 Hz, 1H), 4.14 (d, J=12.8 Hz, 1H), 3.82-3.58 (m, 4H), 3.29-3.18 (m, 5H), 2.94 (t, J=7.6 Hz, 2H), 2.47-2.23 (m, 2H), 0.99 (t, J=7.5 Hz, 3H). LC/MS (method B): 496.4 (M–H)–; 498.3 (M+H)+. HPLC (Method A) Rt 4.31 min (Purity: 98.5%).

Example 32

6-{5-[2-(methoxymethyl)-2'-methylbiphenyl-4-yl]-1,2,4-oxadiazol-3-yl}-1H-indole-2-carboxylic acid

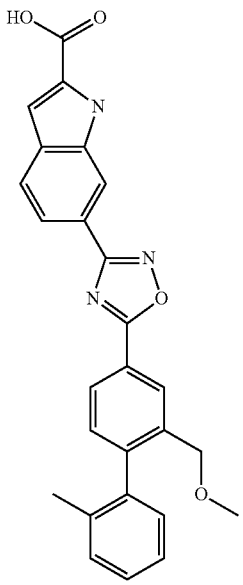 [SMILES: COCc1cc(-c2nc(-c3ccc4cc(C(=O)O)[nH]c4c3)no2)ccc1-c1ccccc1C]

Title compound was prepared following general procedure 3 starting from Intermediate 14 (150 mg; 0.59 mmol; 1 eq.), and Intermediate 30 (128.29 mg; 0.59 mmol; 1 eq.). After evaporation of the solvents, the solid residue was recrystallized from MeOH to give the title compound (30 mg). $^1$H NMR (DMSO-d$_6$) δ13.25 (br s, 1H), 12.15 (br s, 1H), 8.34 (m, 1H), 8.27 (s, 1H), 8.18 (m, 1H), 7.89-7.79 (m, 2H), 7.47-7.11 (m, 6H), 4.23 (d, J=12.7 Hz, 1H), 4.18 (d, J=12.7 Hz, 1H), 3.26 (s, 3H), 2.04 (s, 3H). HPLC (Method A), Rt 5.61 min (Purity: 97.4%). LC/MS (Method B): 426.3 (M+H)$^-$; 428.1 (M+H)$^+$.

Example 33

3-[7-{5-[4-(2-ethylpiperidin-1-yl)-3-(methoxymethyl)phenyl]-1,2,4-oxadiazol-3-yl}-3,4-dihydroisoquinolin-2(1H)-yl]propanoic acid

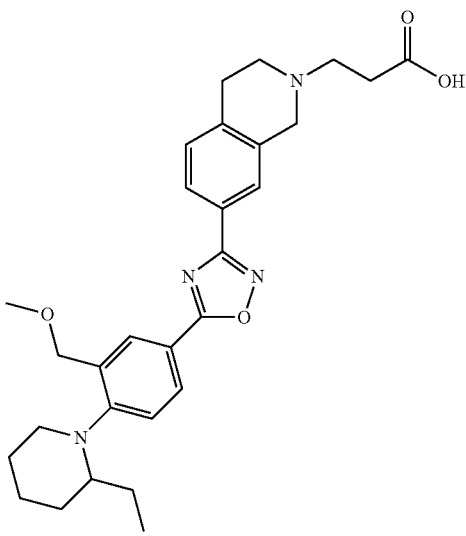 [SMILES: CCC1CCCCN1c1ccc(-c2nc(-c3ccc4c(c3)CN(CCC(=O)O)CC4)no2)cc1COC]

Step 1: tert-butyl 3-[7-{5-[4-(2-ethylpiperidin-1-yl)-3-(methoxymethyl)phenyl]-1,2,4-oxadiazol-3-yl}-3,4-dihydroisoquinolin-2(1H)-yl]propanoate Title compound was prepared following general procedure 2 starting from Intermediate 22 (188 mg; 0.6 mmol) and Intermediate 25 (182 mg; 0.6 mmol). The reaction mixture was diluted with EtOAc, washed with water and brine and evaporated under vacuum.

Purification by silica column chromatography (c-Hex/(DCM/EtOAc 1:1), 90/10 to 50/50) afforded the title compound as a yellow oil. LC/MS (method B): 562.3 (M+H)$^+$. HPLC (Method A) Rt 3.77 min (Purity: 95.0%).

Step 2: 3-[7-{5-[4-(2-ethylpiperidin-1-yl)-3-(methoxymethyl)phenyl]-1,2,4-oxadiazol-3-yl}-3,4-dihydroisoquinolin-2(1H)-yl]propanoic acid tert-butyl 3-[7-{5-[4-(2-ethylpiperidin-1-yl)-3-(methoxymethyl)phenyl]-1,2,4-oxadiazol-3-yl}-3,4-dihydroisoquinolin-2(1H)-yl]propanoate, obtained from step 1 (95 mg; 0.17 mmol; 1 eq.) was dissolved in hydrogen chloride in dioxane (2.1 mL; 4 M; 8.47 mmol; 50 eq.). The mixture was stirred at room temperature overnight. Solvent were removed. The solid residue was triturated with ACN, filtered and dried under vacuum to give the title compound as an orange solid. $^1$H NMR (DMSO-d$_6$) δ 8.18 (d, J=2.0 Hz, 1H), 8.07-7.94 (m, 3H), 7.48 (d, J=8.1 Hz, 1H), 7.35 (d, J=8.3 Hz, 1H), 4.74 (d, J=17.0 Hz, 1H), 4.54 (s, 2H), 4.45 (d, J=15.2 Hz, 1H), 3.83-3.73 (m, 1H), 3.55-3.37 (, 7H), 3.29-3.05 (m, 4H), 2.93 (t, J=7.6 Hz, 2H), 2.79-2.66 (m, 1H), 1.89-1.25 (m, 8H), 0.68 (t, J=7.4 Hz, 3H). LC/MS (method B): 503.4 (M–H)$^-$; 505.3 (M+H)$^+$. HPLC (Method A) Rt 2.90 min (Purity: 94.4%).

Example 34

[7-{5-[4-(2-ethylpiperidin-1-yl)-3-(methoxymethyl)phenyl]-1,2,4-oxadiazol-3-yl}-3,4-dihydroisoquinolin-2(1H)-yl]acetic acid

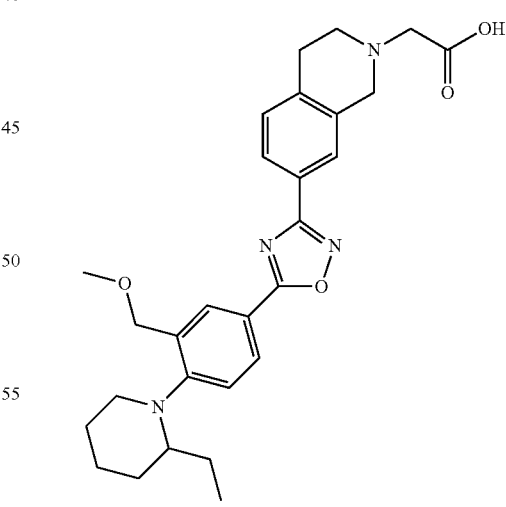

Step 1: tert-butyl [7-{5-[4-(2-ethylpiperidin-1-yl)-3-(methoxymethyl)phenyl]-1,2,4-oxadiazol-3-yl}-3,4-dihydroisoquinolin-2(1H)-yl]acetate Title compound was prepared following general procedure 2 starting from Intermediate 22 (188 mg; 0.6 mmol) and Intermediate 5 (174 mg; 0.6 mmol). The reaction mixture was diluted with EtOAc, washed with water and brine and evaporated under vacuum.

Purification by silica column chromatography (c-Hex/(DCM/EtOAc 1:1), 90/10 to 50/50) afforded the title compound as a yellow oil. LC/MS (method B): 548.3 (M+H)+. HPLC (Method A) Rt 3.63 min.

Step 2: [7-{5-[4-(2-ethylpiperidin-1-yl)-3-(methoxymethyl)phenyl]-1,2,4-oxadiazol-3-yl}-3,4-dihydroisoquinolin-2(1H)-yl]acetic acid tert-butyl [7-{5-[4-(2-ethylpiperidin-1-yl)-3-(methoxymethyl)phenyl]-1,2,4-oxadiazol-3-yl}-3,4-dihydroisoquinolin-2(1H)-yl]acetate, obtained from step 1 (176 mg; 0.32 mmol; 1 eq.) was dissolved in hydrogen chloride in dioxane (4.0 mL; 4 M; 16.1 mmol; 50 eq.). The mixture was stirred at room temperature overnight. Solvent were removed. The solid residue was triturated with ACN, filtered and dried under vacuum to give the title compound as a grey powder (154 mg, 84%). $^1$H NMR (DMSO-$d_6$) δ10.83 (br s, 1H), 8.18 (d, J=2.0 Hz, 1H), 8.07-7.97 (m, 3H), 7.49 (d, J=8.1 Hz, 1H), 7.35 (d, J=8.2 Hz, 1H), 4.71-3.5 (m, 8H), 3.41 (s, 3H), 3.26-3.19 (m, 2H), 3.14-3.05 (m, 2H), 2.76-2.67 (m, 1H), 1.89-1.29 (m, 8H), 0.68 (t, 3H). LC/MS (method B): 489.4 (M−H)−; 491.3 (M+H)+. HPLC (Method A) Rt 2.77 min (Purity: 95.6%).

Example 35

3-[7-{5-[2-(methoxymethyl)-2'-methylbiphenyl-4-yl]-1,2,4-oxadiazol-3-yl}-3,4-dihydroisoquinolin-2(1H)-yl]propanoic acid

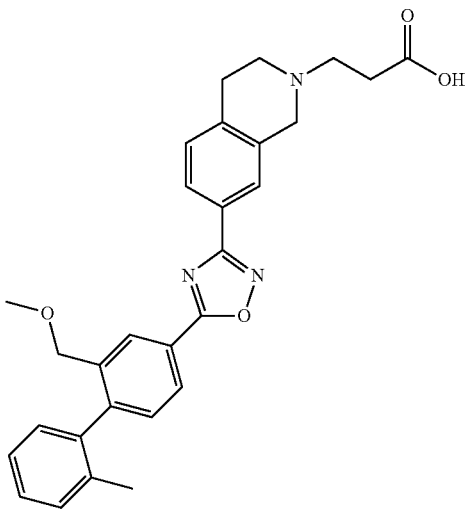 [SMILES: COCc1cc(-c2nc(-c3ccc4c(c3)CN(CCC(=O)O)CC4)no2)ccc1-c1ccccc1C]

Step 1: tert-butyl 3-[7-{5-[2-(methoxymethyl)-2'-methylbiphenyl-4-yl]-1,2,4-oxadiazol-3-yl}-3,4-dihydroisoquinolin-2(1H)-yl]propanoate Title compound was prepared following general procedure 2 starting from Intermediate 14 (154 mg; 0.6 mmol) and Intermediate 25 (182 mg; 0.6 mmol). The reaction mixture was diluted with EtOAc, washed with water and brine and evaporated under vacuum. Purification by silica column chromatography (c-Hex/(DCM/EtOAc 1:1), 90/10 to 50/50) afforded the title compound as a yellow oil. $^1$H NMR (DMSO-$d_6$) δ 8.32 (d, J=1.6 Hz, 1H), 8.16 (dd, J=8.0, 2.0 Hz, 1H), 7.87 (dd, J=8.0, 1.6 Hz, 1H), 7.82 (d, J=1.4 Hz, 1H), 7.42 (d, J=7.9 Hz, 1H), 7.38-7.26 (m, 4H), 7.15 (d, J=7.2 Hz, 1H), 4.25-4.14 (m, 2H), 3.71 (s, 2H), 3.25 (s, 3H), 2.91-2.86 (m, 2H), 2.78-2.70 (m, 4H), 2.53-2.46 (m, 2H), 2.04 (s, 3H), 1.40 (s, 9H). LC/MS (method B): 540.1 (M+H)+. HPLC (Method A) Rt 4.81 min (Purity: 97.4%).

Step 2: 3-[7-{5-[2-(methoxymethyl)-2'-methylbiphenyl-4-yl]-1,2,4-oxadiazol-3-yl}-3,4-dihydroisoquinolin-2(1H)-yl]propanoic acid tert-butyl 3-[7-{5-[2-(methoxymethyl)-2'-methylbiphenyl-4-yl]-1,2,4-oxadiazol-3-yl}-3,4-dihydroisoquinolin-2(1H)-yl]propanoate, obtained from step 1 (100 mg; 0.19 mmol; 1 eq.) was dissolved in hydrogen chloride in dioxane (2.3 mL; 4 M; 9.26 mmol; 50 eq.). The mixture was stirred at room temperature for 4 h. Solvent were removed. The solid residue was triturated with ACN, filtered and dried under vacuum to give the title compound as a white solid (92 mg, 95%). $^1$H NMR (DMSO-$d_6$) δ12.78 (br s, 1H), 10.95 (br s, 1H), 8.33 (d, J=1.5 Hz, 1H), 8.16 (dd, J=7.9, 1.9 Hz, 1H), 8.04 (dd, J=8.0, 1.5 Hz, 1H), 8.00 (d, J=1.4 Hz, 1H), 7.50 (d, J=8.1 Hz, 1H), 7.43 (d, J=7.9 Hz, 1H), 7.38-7.27 (m, 3H), 7.15 (d, 1H), 4.76-4.14 (m, 4H), 3.79-3.39 (m, 4H), 3.29-3.19 (m, 5H), 2.95 (t, J=7.6 Hz, 2H), 2.04 (s, 3H). LC/MS (method B): 482.1 (M−H)−, 484.0 (M+H)+. HPLC (Method A) Rt 4.09 min (Purity: 96.0%).

Example 36

[7-{5-[2'-methyl-2-(trifluoromethyl)biphenyl-4-yl]-1,2,4-oxadiazol-3-yl}-3,4-dihydroisoquinolin-2(1H)-yl]acetic acid

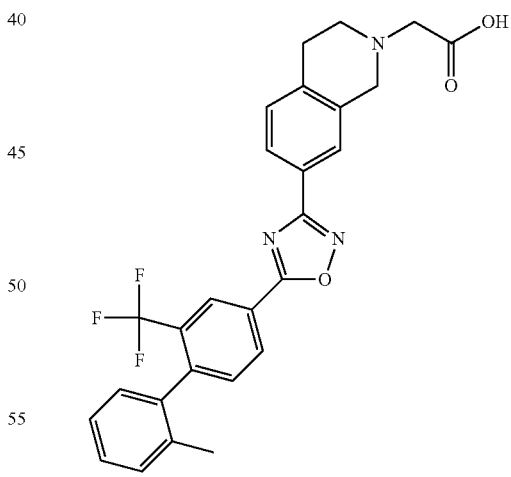

Step 1: tert-butyl [7-{5-[2'-methyl-2-(trifluoromethyl)biphenyl-4-yl]-1,2,4-oxadiazol-3-yl}-3,4-dihydroisoquinolin-2(1H)-yl]acetate Title compound was prepared following general procedure 2 starting from Intermediate 24 (168 mg; 0.6 mmol) and Intermediate 5 (174 mg; 0.6 mmol). The reaction mixture was diluted with EtOAc, washed with water and brine and evaporated under vacuum. Purification with MD-Autoprep afforded the title compound as a yellow oil. LC/MS (method B): 550.1 (M+H)⁺. HPLC (Method A) Rt 4.95 min.

Step 2: [7-{5-[2'-methyl-2-(trifluoromethyl)biphenyl-4-yl]-1,2,4-oxadiazol-3-yl}-3,4-dihydroisoquinolin-2(1H)-yl]acetic acid tert-butyl [7-{5-[2'-methyl-2-(trifluoromethyl)biphenyl-4-yl]-1,2,4-oxadiazol-3-yl}-3,4-dihydroisoquinolin-2(1H)-yl]acetate, obtained from step 1 (58 mg; 0.11 mmol; 1 eq.) was dissolved in hydrogen chloride in dioxane (1.3 mL; 4 M; 5.28 mmol; 50 eq.). The mixture was stirred at room temperature for 8 h. Solvent were removed. The solid residue was triturated with ACN, filtered and dried under vacuum to give the title compound as a white solid. $^1$H NMR (DMSO-$d_6$) δ 8.55 (d, J=1.5 Hz, 1H), 8.50 (dd, J=7.9, 1.6 Hz, 1H), 8.07-8.02 (m, 2H), 7.68 (d, J=8.0 Hz, 1H), 7.51 (d, J=8.1 Hz, 1H), 7.42-7.26 (m, 3H), 7.17 (d, J=7.3 Hz, 1H), 4.60 (s, 2H), 4.24 (s, 2H), 3.60 (br s, 2H), 3.26-3.19 (m, 2H), 2.03 (s, 3H). LC/MS (method B): 492.1 (M−H)⁻; 494.0 (M+H)⁺. HPLC (Method A) Rt 4.29 min (Purity: 97.9%).

Example 37

3-[7-{5-[4-(2-methylpiperidin-1-yl)-3-(trifluoromethyl)phenyl]-1,2,4-oxadiazol-3-yl}-3,4-dihydroisoquinolin-2(1H)-yl]propanoic acid

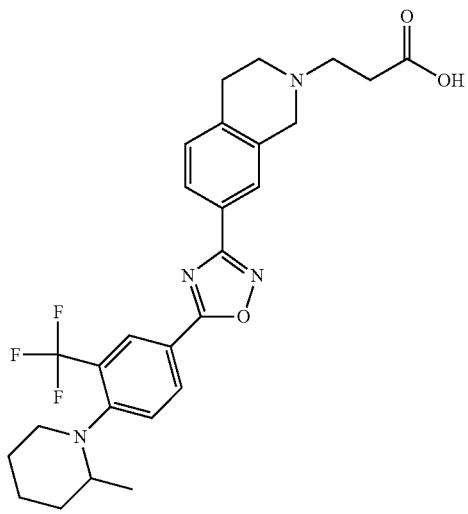 [SMILES: CC1CCCCN1c1ccc(-c2nc(-c3ccc4c(c3)CN(CCC(=O)O)CC4)no2)cc1C(F)(F)F]

Step 1: tert-butyl [7-{5-[2'-methyl-2-(trifluoromethyl)biphenyl-4-yl]-1,2,4-oxadiazol-3-yl}-3,4-dihydroisoquinolin-2(1H)-yl]acetate Title compound was prepared following general procedure 3 starting from Intermediate 11 (172 mg; 0.6 mmol) and Intermediate 25 (182 mg; 0.6 mmol). The reaction mixture was diluted with EtOAc, washed with water and brine and evaporated under vacuum. Purification by silica column chromatography (c-Hex/(DCM/EtOAc 1:1), 90/10 to 50/50) afforded the title compound as a yellow oil. LC/MS (method B): 572.2 (M+H)⁺. HPLC (Method A) Rt 5.37 min (Purity: 95.0%).

Step 2: 3-[7-{5-[4-(2-methylpiperidin-1-yl)-3-(trifluoromethyl)phenyl]-1,2,4-oxadiazol-3-yl}-3,4-dihydroisoquinolin-2(1H)-yl]propanoic acid tert-butyl 3-[7-{5-[4-(2-methylpiperidin-1-yl)-3-(trifluoromethyl)phenyl]-1,2,4-oxadiazol-3-yl}-3,4-dihydroisoquinolin-2(1H)-yl]propanoate, obtained from step 1 (166 mg; 0.29 mmol; 1 eq.) was dissolved in hydrogen chloride in dioxane (3.6 mL; 4 M; 14.54 mmol; 50 eq.). The mixture was stirred at room temperature for 7 h30. Solvent were removed. The solid residue was triturated with ACN, filtered and dried under vacuum to give the title compound as a white solid (123 mg, 72%). $^1$H NMR (DMSO-$d_6$) δ 12.8 (br s, 1H), 11.9 (br s, 1H), 8.44 (dd, J=8.4, 2.0 Hz, 1H), 8.39 (d, J=2.0 Hz, 1H), 8.02 (dd, J=8.0, 1.6 Hz, 1H), 7.98 (s, 1H), 7.87 (d, J=8.7 Hz, 1H), 7.49 (d, J=8.1 Hz, 1H), 4.80-4.39 (m, 2H), 3.80-3.13 (m, 8H), 2.99-2.90 (m, 3H), 2.68-2.58 (m, 1H), 1.84-1.74 (m, 2H), 1.69-1.27 (m, 4H), 0.79 (d, J=6.2 Hz, 3H). LC/MS (method B): 513.2 (M−H)⁻; 515.0 (M+1-1)⁺. HPLC (Method A) Rt 4.72 min (Purity: 97.7%).

Example 38

[7-{5-[4-(2-methylpiperidin-1-yl)-3-(trifluoromethyl)phenyl]-1,2,4-oxadiazol-3-yl}-3,4-dihydroisoquinolin-2(1H)-yl]acetic acid

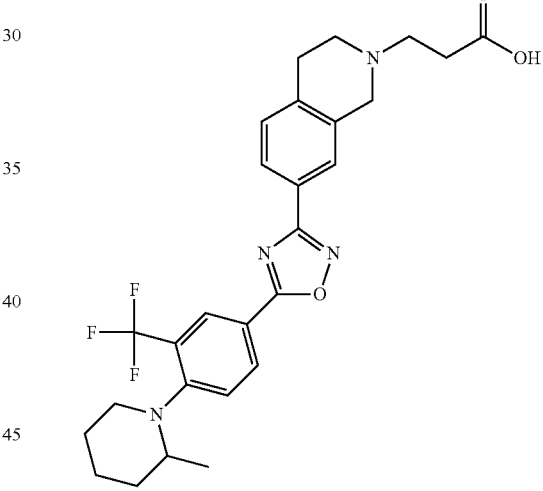

Step 1: tert-butyl [7-{5-[4-(2-methylpiperidin-1-yl)-3-(trifluoromethyl)phenyl]-1,2,4-oxadiazol-3-yl}-3,4-dihydroisoquinolin-2(1H)-yl]acetate Title compound was prepared following general procedure 3 starting from intermediate 11 (172 mg; 0.6 mmol) and intermediate 5 (183 mg; 0.6 mmol). The reaction mixture was diluted with EtOAc, washed with water and brine and evaporated under vacuum. Purification by silica column chromatography (c-Hex/(DCM/EtOAc 1:1), 90/10 to 50/50) afforded the title compound as a yellow oil. LC/MS (method B): 558.1 (M+H)⁺. HPLC (Method A) Rt 5.30 min.

Step 2: [7-{5-[4-(2-methylpiperidin-1-yl)-3-(trifluoromethyl)phenyl]-1,2,4-oxadiazol-3-yl}-3,4-dihydroisoquinolin-2(1H)-yl]acetic acid tert-butyl [7-{5-[4-(2-methylpiperidin-1-yl)-3-(trifluoromethyl)phenyl]-1,2,4-oxadiazol-3-yl}-3,4-dihydroisoquinolin-2(1H)-yl]acetate, obtained from step 1 (211 mg; 0.38 mmol; 1 eq.) was dissolved in hydrogen chloride in dioxane (4.7 mL; 4 M; 18.95 mmol; 50 eq.). The mixture was stirred at room temperature for 7 h30. Solvent were removed. The solid residue was triturated with ACN, filtered and dried under vacuum to give the title compound as a light yellow powder (165 mg, 76%). $^1$H NMR (DMSO-$d_6$) δ 8.45 (dd, J=8.4, 1.2 Hz, 1H), 8.38 (d, J=1.8 Hz, 1H), 8.04-7.98 (m, 2H), 7.87 (d, J=8.5 Hz, 1H), 7.49 (d, J=7.9 Hz, 1H), 4.63 (s, 2H), 4.27 (s, 2H), 3.63 (s, 2H), 3.27-3.13 (m, 3H), 2.99-2.92 (m, 1H), 2.67-2.58 (m, 1H), 1.84-1.74 (m, 2H), 1.69-1.23 (m, 4H), 0.79 (d, J=6.0 Hz, 3H). LC/MS (method B): 499.1 (M−H)$^−$; 501.0 (M+H)$^+$. HPLC (Method A) Rt 4.68 min (Purity: 96.9%).

Example 39

3-[7-{5-[2'-methyl-2-(trifluoromethyl)biphenyl-4-yl]-1,2,4-oxadiazol-3-yl}-3,4-dihydroisoquinolin-2(1H)-yl]propanoic acid

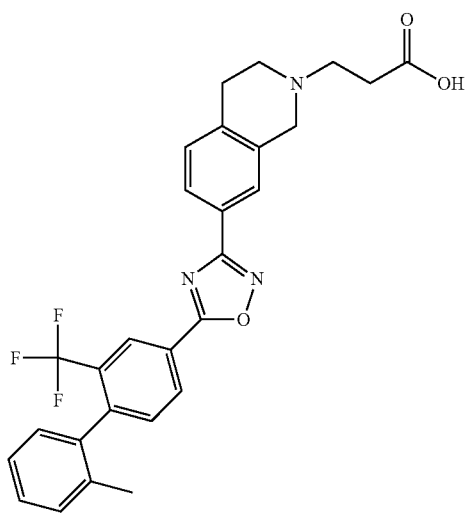 [SMILES: Cc1ccccc1-c1ccc(-c2nc(-c3ccc4c(c3)CN(CCC(=O)O)CC4)no2)cc1C(F)(F)F]

Step 1: tert-butyl 3-[7-{5-[2'-methyl-2-(trifluoromethyl)biphenyl-4-yl]-1,2,4-oxadiazol-3-yl}-3,4-dihydroisoquinolin-2(1H)-yl]propanoate Title compound was prepared following general procedure 3 starting from Intermediate 24 (168 mg; 0.6 mmol) and Intermediate 25 (182 mg; 0.6 mmol). The reaction mixture was diluted with EtOAc, washed with water and brine and evaporated under vacuum. Purification by silica column chromatography (c-Hex/(DCM/EtOAc 1:1), 90/10 to 50/50) afforded the title compound as a yellow oil. LC/MS (method B): 565.2 (M+H)$^+$. HPLC (Method A) Rt 5.00 min (Purity: 95.4%).

Step 2: 3-[7-{5-[2'-methyl-2-(trifluoromethyl)biphenyl-4-yl]-1,2,4-oxadiazol-3-yl}-3,4-dihydroisoquinolin-2(1H)-yl]propanoic acid tert-butyl 3-[7-{5-[2'-methyl-2-(trifluoromethyl)biphenyl-4-yl]-1,2,4-oxadiazol-3-yl}-3,4-dihydroisoquinolin-2(1H)-yl]propanoate, obtained from step 1 (136.1 mg; 0.24 mmol; 1 eq.) was dissolved in hydrogen chloride in dioxane (3.0 mL; 4 M; 12.07 mmol; 50 eq.). The mixture was stirred at room temperature for 7 h30. Solvent were removed. The solid residue was triturated with ACN, filtered and dried under vacuum to give the title compound as a white solid (105 mg, 80%). $^1$H NMR (DMSO-$d_6$) δ 12.74 (br s, 1H), 10.98 (br s, 1H), 8.55 (d, J=1.3 Hz, 1H), 8.50 (dd, J=8.0, 1.4 Hz, 1H), 8.05 (dd, J=8.0, 1.5 Hz, 1H), 8.01 (s, 1H), 7.68 (d, J=8.0 Hz, 1H), 7.51 (d, J=8.1 Hz, 1H), 7.42-7.26 (m, 3H), 7.17 (d, J=7.5 Hz, 1H), 4.58 (br s, 2H), 3.72-3.19 (m, 6H), 2.95 (t, J=7.6 Hz, 2H), 2.03 (s, 3H). LC/MS (method B): 506.1 (M−H)$^−$; 508.0 (M+H)$^+$. HPLC (Method A) Rt 4.35 min (Purity: 98.6%).

Example 40

3-{6-[5-(2-Methoxymethyl-2'-methyl-biphenyl-4-yl)-[1,2,4]oxadiazol-3-yl]-3,4-dihydro-1H-isoquinolin-2-yl}-propionic acid

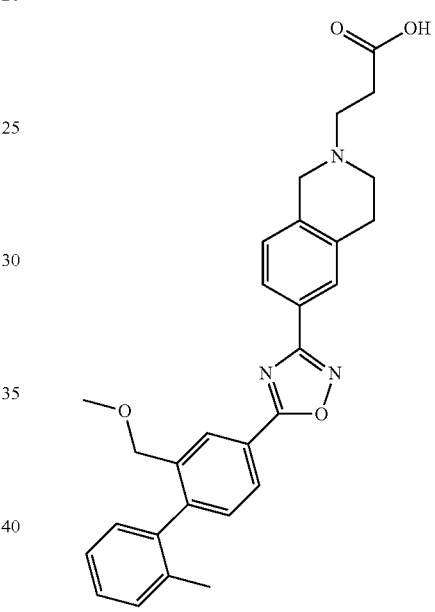

Title compound was prepared following the procedure described for Example 39, starting from intermediate 14 and tert-butyl 3-[6-[amino(hydroxyimino)methyl]-3,4-dihydroisoquinolin-2(1H)-yl]propanoate (obtained following the same procedure as Intermediate 25, starting from 1,2,3,4-tetrahydroisoquinoline-6-carbonitrile, prepared according to *Synthetic Communications* 1995, 25, 3255-61). It was isolated as a pale yellow oi. $^1$H NMR (DMSO-$d_6$) δ 8.34 (d, J=1.5 Hz, 1H), 8.16 (dd, J=7.9, 1.9 Hz, 1H), 7.95-7.85 (m, 2H), 7.50-7.25 (m, 5H), 7.17 (d, 1H), 4.24 (d, J=12.7 Hz, 1H), 4.20 (d, J=12.7 Hz, 1H), 3.80 (s, 2H), 3.28 (s, 3H), 3.10-2.75 (m, 6H), 2.70-2.55 (m, 2H), 2.07 (s, 3H). LC/MS (method B): 482 (M−H)$^−$; 484 (M+H)$^+$. HPLC (Method D) Rt 17.1 min.

Example 41

In Vitro Assays

Receptor binding assay: Membranes were prepared from CHO cells expressing S1P1 or S1P3 for use in ligand and 35S-GTPγS binding studies. Cells were suspended in 50 mM TRIS, pH 7.4, 2 mM EDTA, 250 mM Sucrose (buffer A) and 1× Complete protease inhibitor cocktail (Roche), and disrupted at 4° C. by N2 decompression using a cell disruption bomb (Parr Instrument). Following centrifugation at 1000 RPM for 10 min at 4° C., the supernatant was suspended in buffer A and centrifuged again at 19000 RPM for 60 min at 4° C. The pellet was then suspended in 10 mM HEPES, pH 7.4, 1 mM EDTA, 250 mM Sucrose (Buffer B), and 1× Complete EDTA-free protease inhibitor cocktail and homogenized using a potter. Membranes were flash frozen in liquid N2 and stored at −80° C. [33P]sphingosine 1-phosphate (3000 Ci/mmol; American Radiolabeled Chemicals, Inc.) was added to test compounds in DMSO. Membranes and WGA SPA beads (GE Healthcare) were added to give a final volume of 100 μl in 96-well plates with assay concentrations of 25 μM or 10 μM [33P]sphingosine 1-phosphate (respectively for S1P1 or S1P3), 50 mM HEPES, pH 7.5, 5 mM MgCl2, 100 mM NaCl, 0.4% fatty acid-free BSA, 1-5 μg/well of proteins and 100 μg/well of WGA SPA beads. Binding was performed for 60 min at RT on a shaker and bound radioactivity was measured on a PerkinElmer 1450 MicroBeta counter. Specific binding was calculated by subtracting remaining radioactivity in the presence of 1000-fold excess of unlabeled S1P. Binding data were analyzed using the GraphPad Prism program.

Measurements of 35S-GTPγS Binding:

Membranes (1 to 10 μg protein) prepared as described above, were incubated in 96-well Scintiplates (PerkinElmer) with test compounds diluted in DMSO, in 180 μl of 20 mM HEPES, pH 7.4, 10 mM MgCl2, 2 μg/well Saponin, 0.2% fatty acid free BSA (Assay buffer), 140 mM NaCl and 1.7 μM GDP. The assay was initiated with the addition of 20 μl of 1.5 nM [35S]-GTPγS (1100 Ci/mmol; GE Healthcare) in assay buffer. After 60 min incubation at 30° C. on a shaker, plates were centrifuged for 10 min at 2000 RPM. Supernatant was discarded and membrane bound radioactivity was measured on a PerkinElmer 1450 MicroBeta counter. Triplicate samples were averaged and expressed as % response relative to S1P activation in absence of compound (n=2).

The compounds of formula I have utility as immunoregulatory agents as demonstrated by their activity as potent and selective agonists of the S1P1 receptor over the S1P3 receptor as measured in the assays described above. In particular, the compounds of formula I exhibit a selectivity for the S1P1 receptor over the S1P3 receptor as measured by the ratio of EC50 for the S1P1 receptor to the EC50 for the S1P3 receptor as evaluated in the 35S-GTPγS binding assay described above.

The following results have been obtained:

| compound Nb | Structure | S1P1 binding Ki (μM) | S1P1 GTPγS EC50 (μM) | S1P3 GTPγS EC50 (μM) |
|---|---|---|---|---|
| 1 | | 0.005 | 0.011 | 0.621 |
| 2 | | — | 0.010 | — |
| 3 | | 0.038 | 0.094 | — |

-continued

| compound Nb | Structure | S1P1 binding Ki (μM) | S1P1 GTPγS EC50 (μM) | S1P3 GTPγS EC50 (μM) |
|---|---|---|---|---|
| 4 | 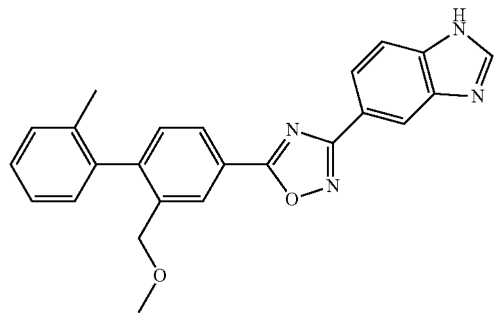 [SMILES: COCc1cc(-c2nc(-c3ccc4[nH]cnc4c3)no2)ccc1-c1ccccc1C] | 0.005 | 0.0084 | 0.325 |
| 5 | 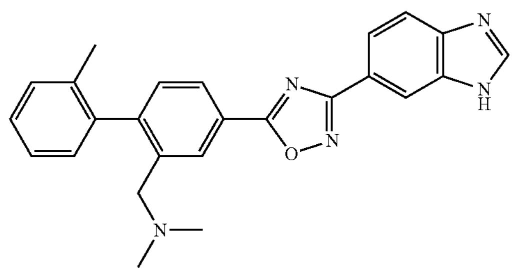 [SMILES: Cc1ccccc1-c1ccc(-c2nc(-c3ccc4nc[nH]c4c3)no2)cc1CN(C)C] | 0.005 | 0.0034 | — |
| 6 | 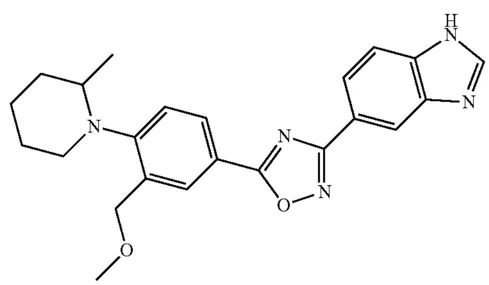 [SMILES: COCc1cc(-c2nc(-c3ccc4[nH]cnc4c3)no2)ccc1N1CCCCC1C] | — | 0.0025 | — |
| 7 | 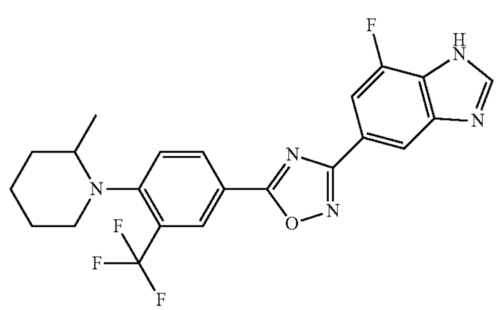 [SMILES: CC1CCCCN1c1ccc(-c2nc(-c3cc(F)c4[nH]cnc4c3)no2)cc1C(F)(F)F] | — | 0.014 | — |
| 8 | 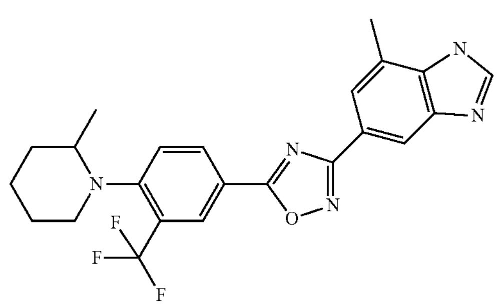 [SMILES: Cc1cc(-c2noc(-c3ccc(N4CCCCC4C)c(C(F)(F)F)c3)n2)cc2nc[nH]c12] | — | 0.007 | — |

-continued

| compound Nb | Structure | S1P1 binding Ki (μM) | S1P1 GTPγS EC50 (μM) | S1P3 GTPγS EC50 (μM) |
|---|---|---|---|---|
| 9 | 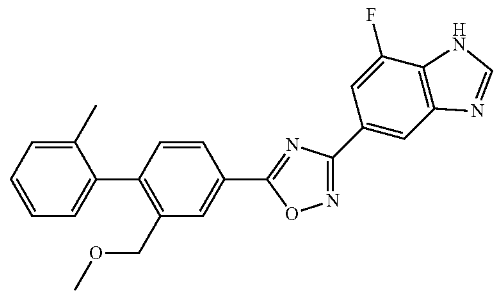 [SMILES: COCc1cc(-c2nc(-c3cc(F)c4[nH]cnc4c3)no2)ccc1-c1ccccc1C] | — | 0.0005 | — |
| 10 | 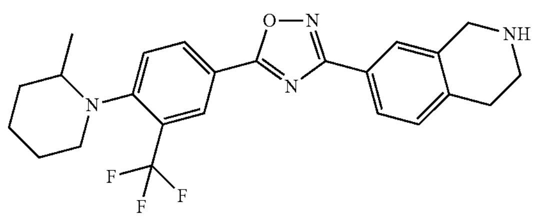 [SMILES: CC1CCCCN1c1ccc(-c2nc(-c3ccc4c(c3)CNCC4)no2)cc1C(F)(F)F] | 0.003 | 0.012 | 0.584 |
| 11 | 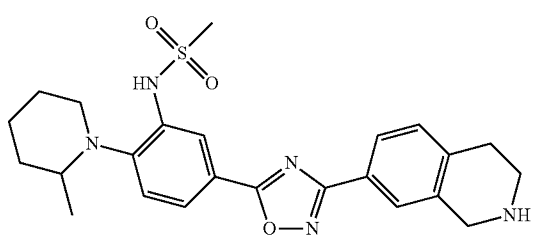 [SMILES: CC1CCCCN1c1ccc(-c2nc(-c3ccc4c(c3)CNCC4)no2)cc1NS(C)(=O)=O] | 0.004 | 0.006 | 0.159 |
| 12 | 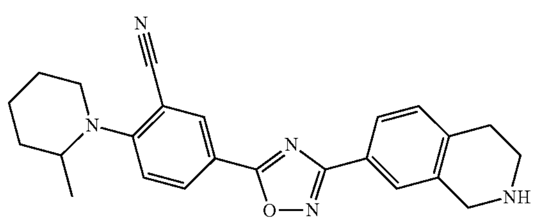 [SMILES: CC1CCCCN1c1ccc(-c2nc(-c3ccc4c(c3)CNCC4)no2)cc1C#N] | 0.0008 | 0.009 | — |
| 13 | 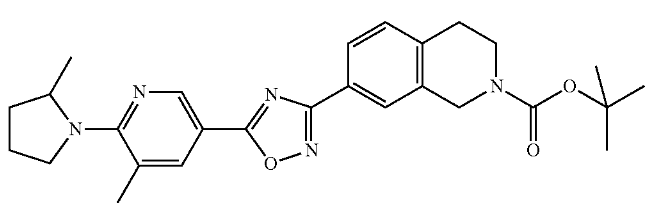 [SMILES: Cc1cc(-c2nc(-c3ccc4c(c3)CN(C(=O)OC(C)(C)C)CC4)no2)cnc1N1CCCC1C] | — | >20 | — |
| 14 | 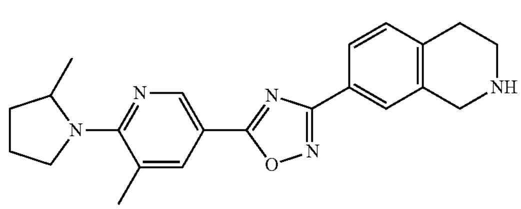 [SMILES: Cc1cc(-c2nc(-c3ccc4c(c3)CNCC4)no2)cnc1N1CCCC1C] | — | 0.064 | — |

-continued

| compound Nb | Structure | S1P1 binding Ki (μM) | S1P1 GTPγS EC50 (μM) | S1P3 GTPγS EC50 (μM) |
|---|---|---|---|---|
| 15 | 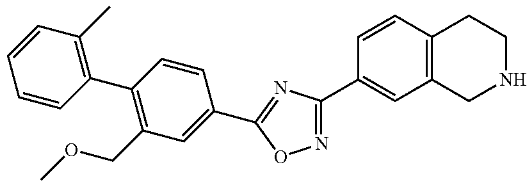 [SMILES: COCc1cc(-c2nc(-c3ccc4c(c3)CNCC4)no2)ccc1-c1ccccc1C] | 0.001 | 0.006 | — |
| 16 | 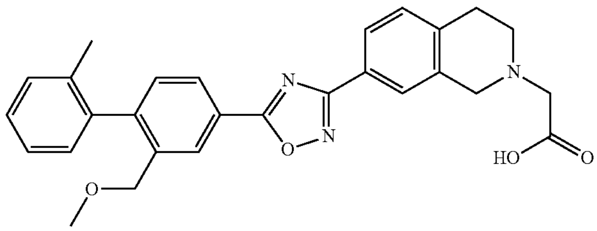 [SMILES: COCc1cc(-c2nc(-c3ccc4c(c3)CN(CC(=O)O)CC4)no2)ccc1-c1ccccc1C] | 0.0007 | 0.0021 | — |
| 17 | 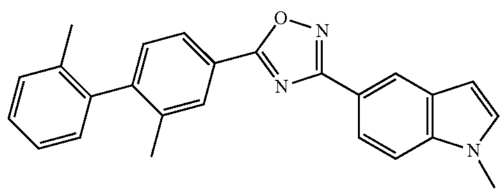 [SMILES: Cc1ccccc1-c1ccc(-c2nc(-c3ccc4c(ccn4C)c3)no2)cc1C] | — | 1.327 | — |
| 18 | 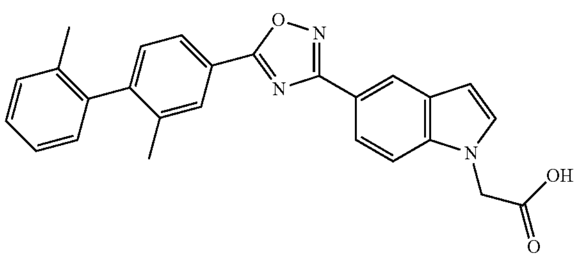 [SMILES: Cc1ccccc1-c1ccc(-c2nc(-c3ccc4c(ccn4CC(=O)O)c3)no2)cc1C] | — | 3.025 | — |
| 19 | 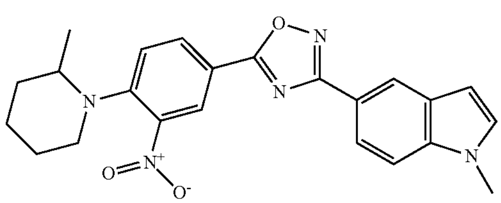 [SMILES: CC1CCCCN1c1ccc(-c2nc(-c3ccc4c(ccn4C)c3)no2)cc1[N+](=O)[O-]] | — | 1.267 | — |
| 20 | 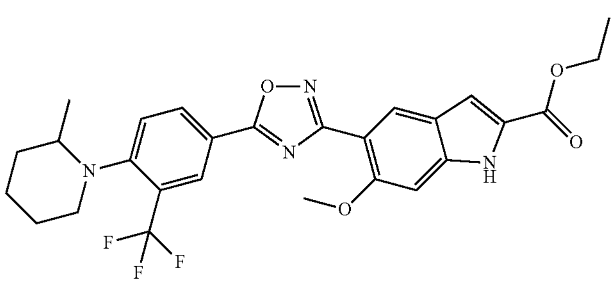 [SMILES: CCOC(=O)c1cc2cc(-c3noc(-c4ccc(N5CCCCC5C)c(C(F)(F)F)c4)n3)c(OC)cc2[nH]1] | — | — | — |

-continued
| compound Nb | Structure | S1P1 binding Ki (μM) | S1P1 GTPγS EC50 (μM) | S1P3 GTPγS EC50 (μM) |
|---|---|---|---|---|
| 21 | 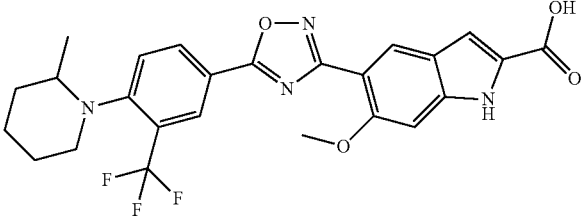 [SMILES: COc1cc2[nH]c(C(=O)O)cc2cc1-c1noc(-c2ccc(N3CCCCC3C)c(C(F)(F)F)c2)n1] | — | 0.468 | — |
| 22 | 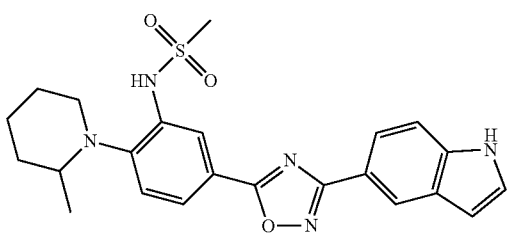 [SMILES: CC1CCCCN1c1ccc(-c2nc(-c3ccc4[nH]ccc4c3)no2)cc1NS(C)(=O)=O] | 0.164 | 0.016 | — |
| 23 | 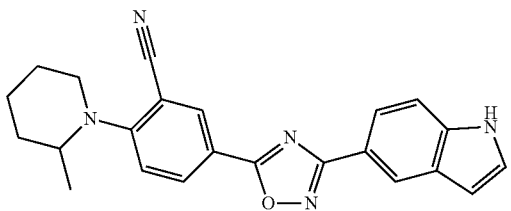 [SMILES: CC1CCCCN1c1ccc(-c2nc(-c3ccc4[nH]ccc4c3)no2)cc1C#N] | — | 0.042 | — |
| 24 | 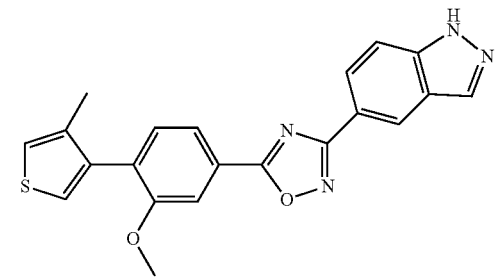 [SMILES: COc1cc(-c2nc(-c3ccc4[nH]ncc4c3)no2)ccc1-c1cscc1C] | 0.003 | 0.004 | — |
| 25 | 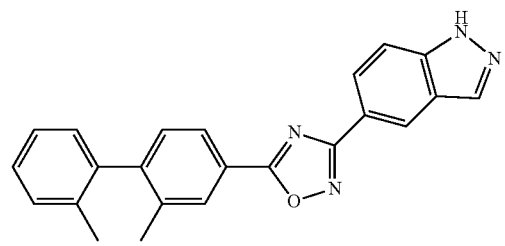 [SMILES: Cc1ccccc1-c1ccc(-c2nc(-c3ccc4[nH]ncc4c3)no2)cc1C] | 0.011 | 0.032 | — |
| 26 | 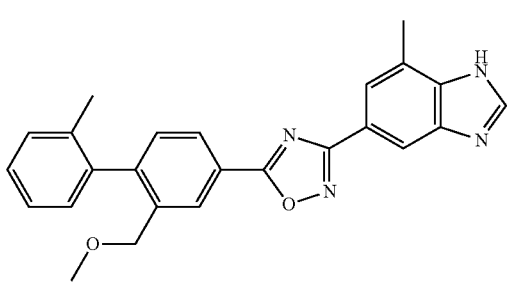 [SMILES: COCc1cc(-c2nc(-c3cc(C)c4[nH]cnc4c3)no2)ccc1-c1ccccc1C] | — | 0.0381 | — |

-continued

| compound Nb | Structure | S1P1 binding Ki (μM) | S1P1 GTPγS EC50 (μM) | S1P3 GTPγS EC50 (μM) |
|---|---|---|---|---|
| 27 | 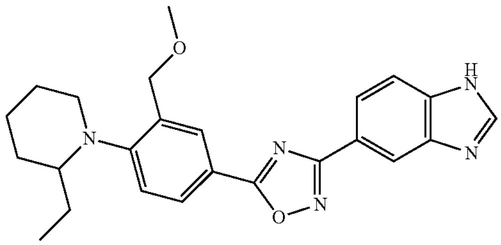 [SMILES: CCC1CCCCN1c1ccc(-c2nc(-c3ccc4[nH]cnc4c3)no2)cc1COC] | 0.00426 | 0.0170 | — |
| 28 | 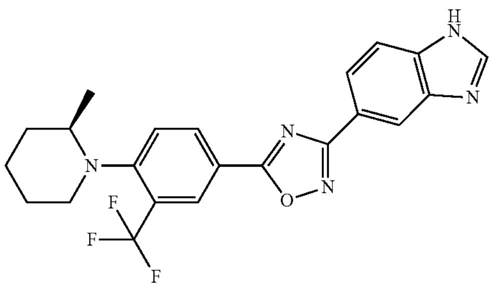 [SMILES: C[C@@H]1CCCCN1c1ccc(-c2nc(-c3ccc4[nH]cnc4c3)no2)cc1C(F)(F)F] | — | 0.023 | — |
| 29 | 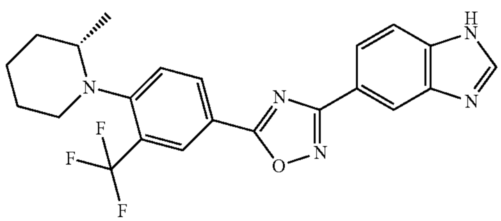 [SMILES: C[C@H]1CCCCN1c1ccc(-c2nc(-c3ccc4[nH]cnc4c3)no2)cc1C(F)(F)F] | — | 0.003 | — |
| 30 | 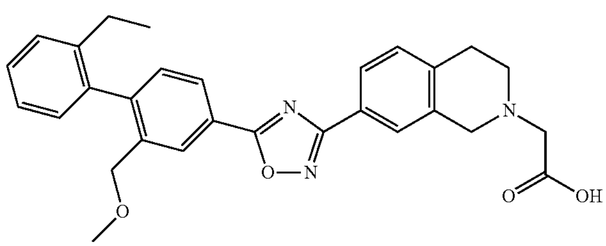 [SMILES: CCc1ccccc1-c1ccc(-c2nc(-c3ccc4c(c3)CN(CC(=O)O)CC4)no2)cc1COC] | — | 0.00439 | — |
| 31 | 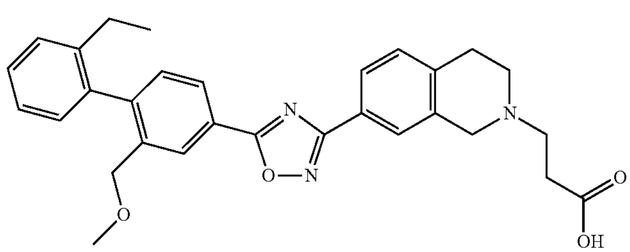 [SMILES: CCc1ccccc1-c1ccc(-c2nc(-c3ccc4c(c3)CN(CCC(=O)O)CC4)no2)cc1COC] | — | 0.00252 | — |
| 32 | 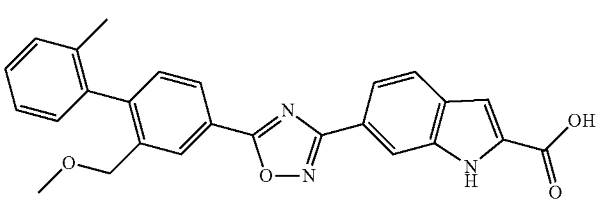 [SMILES: COCc1cc(-c2nc(-c3ccc4cc(C(=O)O)[nH]c4c3)no2)ccc1-c1ccccc1C] | — | 0.0308 | — |

| compound Nb | Structure | S1P1 binding Ki (μM) | S1P1 GTPγS EC50 (μM) | S1P3 GTPγS EC50 (μM) |
|---|---|---|---|---|
| 33 | 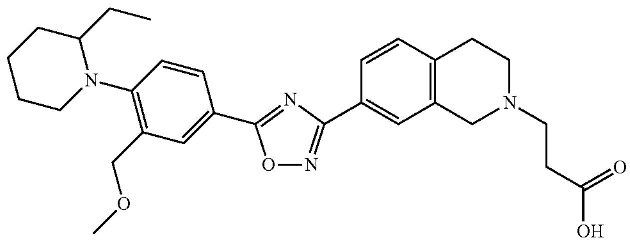 [SMILES: CCC1CCCCN1c1ccc(-c2nc(-c3ccc4c(c3)CN(CCC(=O)O)CC4)no2)cc1COC] | — | 0.00089 | — |
| 34 | 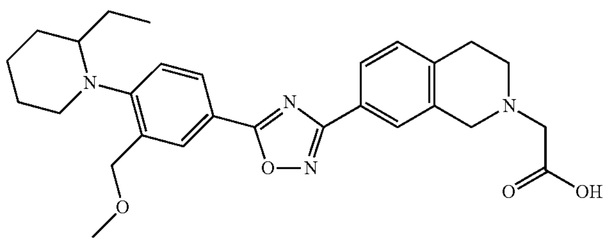 [SMILES: CCC1CCCCN1c1ccc(-c2nc(-c3ccc4c(c3)CN(CC(=O)O)CC4)no2)cc1COC] | — | 0.00193 | — |
| 35 | 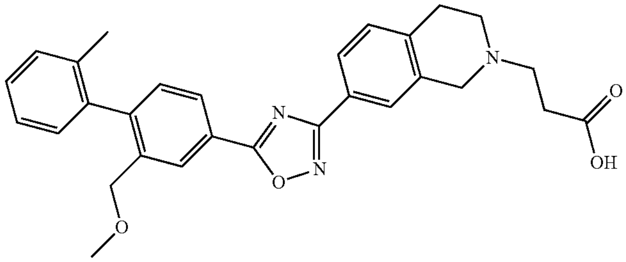 [SMILES: COCc1cc(-c2nc(-c3ccc4c(c3)CN(CCC(=O)O)CC4)no2)ccc1-c1ccccc1C] | 0.00023 | — | — |
| 36 | 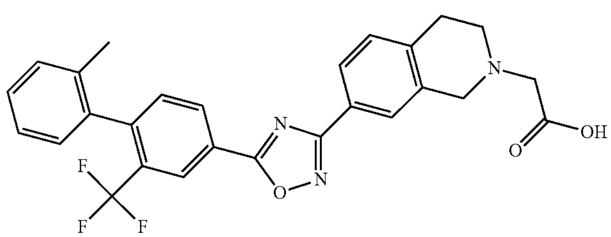 [SMILES: Cc1ccccc1-c1ccc(-c2nc(-c3ccc4c(c3)CN(CC(=O)O)CC4)no2)cc1C(F)(F)F] | 0.00049 | — | — |
| 37 | 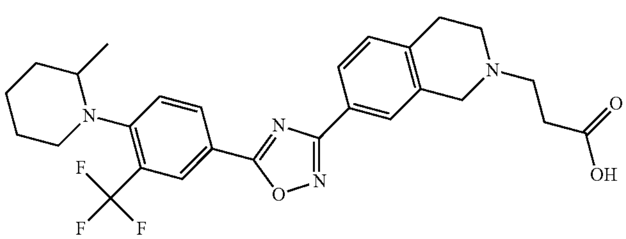 [SMILES: CC1CCCCN1c1ccc(-c2nc(-c3ccc4c(c3)CN(CCC(=O)O)CC4)no2)cc1C(F)(F)F] | 0.00075 | — | — |
| 38 | 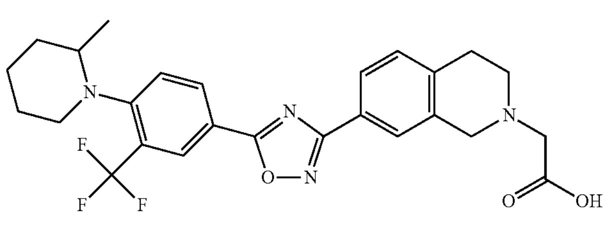 [SMILES: CC1CCCCN1c1ccc(-c2nc(-c3ccc4c(c3)CN(CC(=O)O)CC4)no2)cc1C(F)(F)F] | 0.0008 | — | — |

| compound Nb | Structure | S1P1 binding Ki (µM) | S1P1 GTPγS EC50 (µM) | S1P3 GTPγS EC50 (µM) |
|---|---|---|---|---|
| 39 | 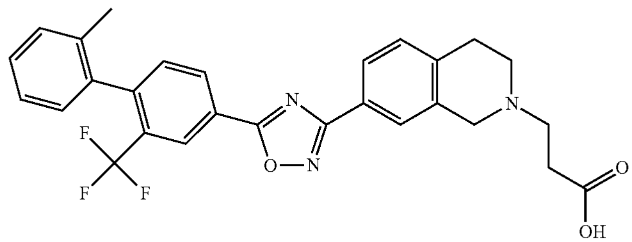 [SMILES: Cc1ccccc1-c1ccc(-c2nc(-c3ccc4c(c3)CN(CCC(=O)O)CC4)no2)cc1C(F)(F)F] | 0.0006 | — | — |
| 40 | 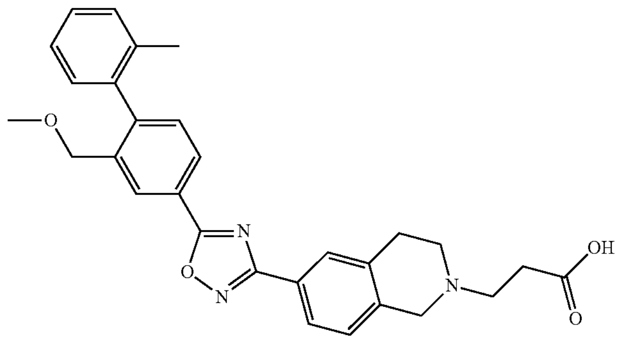 [SMILES: COCc1cc(-c2nc(-c3ccc4c(c3)CCN(CCC(=O)O)C4)no2)ccc1-c1ccccc1C] | 0.0011 | — | — |

Example 42

Animal Models Evaluating the In Vivo Efficacy of S1P Agonists Model of SIP Agonists-Induced Lymphopenia in Mice Female C57BL/6 mice (Elevage Janvier) (8 week old) receive S1P agonists by oral route. Blood is sampled in heparinized (100 IU/kg, ip) mice by intracardiac or retroorbital puncture under isoflurane anesthesia 2 to 120 hrs after drug treatment. The white blood cells (lymphocytes and neutrophils) are counted using a Beckman/Coulter counter. The quality of blood sampling is assessed by counting erythocytes and platelets.

Model of MOG-Induced Experimental Autoimmune Encephalomyelytis (EAE) in Mice

EAE was induced in 9 weeks old female mice (C57BL/6, Elevage Janvier) by an immunization against MOG. The mice received Pertussis toxin (Alexis, 300 ng/mouse in 200 µl of PBS) by ip route and 100 µl of an emulsion containing MOG35-55 peptide (NeoMPS, 200 µg/mouse), *Mycobacterium Tuberculosis* (0.25 mg/mouse) in Complete Freund's Adjuvant (DIFCO) by subcutaneous injection into the back. Two days later an additional injection of Pertussis toxin (Alexis, 300 ng/mouse in 200 µl of PBS) was done by ip route. After EAE induction, mice were weighed daily and the neurological impairment was quantified using a 15-points clinical scale assessing the paralysis (tail, hind limbs and fore limbs), the incontinency and the death.

Clinical Score

1—Tail
  Score=0 A normal mouse holds its tail erect when moving.
  Score=1 If the extremity of the tail is flaccid with a tendency to fall.
  Score=2 If the tail is completely flaccid and drags on the table.

2—Hind limbs
  Score=0 A normal mouse has an energetic walk and doesn't drag his paws.
  Score=1 Either one of the following tests is positive:
  a—Flip test: while holding the tail between thumb and index finger, flip the animal on his back and observe the time it takes to right itself. A healthy mouse will turn itself immediately. A delay suggests hind-limb weakness.
  b—Place the mouse on the wire cage top and observe as it crosses from one side to the other. If one or both limbs frequently slip between the bars we consider that there is a partial paralysis.
  Score=2 Both previous tests are positive.
  Score=3 One or both hind limbs show signs of paralysis but some movements are preserved; for example: the animal can grasp and hold on to the underside of the wire cage top for a short moment before letting go.
  Score=4 When both hind legs are paralyzed and the mouse drags them when moving.

3—Fore limbs:
  Score=0 A normal mouse uses his front paws actively for grasping and walking and holds his head erect.
  Score=1 Walking is possible but difficult due to a weakness in one or both of the paws, for example, the front paws are considered weak when the mouse has difficulty grasping the underside of the wire top cage. Another sign of weakness is head drooping.
  Score=2 When one forelimb is paralyzed (impossibility to grasp and the mouse turns around the paralyzed limb). At this time the head has also lost much of its muscle tone.
  Score=3 Mouse cannot move, and food and water are unattainable.

4—Bladder:
  Score=0 A normal mouse has full control of his bladder.
  Score=1 A mouse is considered incontinent when his lower body is soaked with urine.
5—Death:
  Score=15

The final score for each animal is determined by the addition of all the above-mentioned categories. The maximum score for live animals is 10.

At day 12 (first signs of paralysis) the mice were stratified in experimental groups (n=10) according to the clinical score and the body weight loss. The semi-curative treatment started at day 14.

Example 43

Preparation of a Pharmaceutical Formulation

Formulation 1—Tablets
A compound of formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active compound according to the invention per tablet) in a tablet press.
Formulation 2—Capsules
A compound of formula (I) is admixed as a dry powder with a starch diluent in an approximate 1:1 weight ratio. The mixture is filled into 250 mg capsules (125 mg of active compound according to the invention per capsule).
Formulation 3—Liquid
A compound of formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.
Formulation 4—Tablets
A compound of formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active compound according to the invention) in a tablet press.
Formulation 5—Injection
A compound of formula (I) is dissolved in a buffered sterile saline injectable aqueous medium to a concentration of approximately 5 mg/mL.

The invention claimed is:
1. A compound of formula (I):

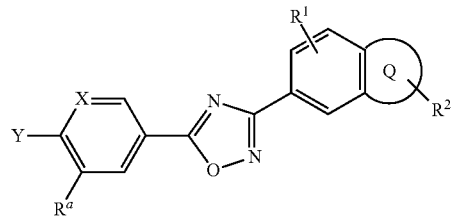

(I)

wherein
the group

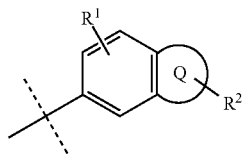

denotes one of the following groups:

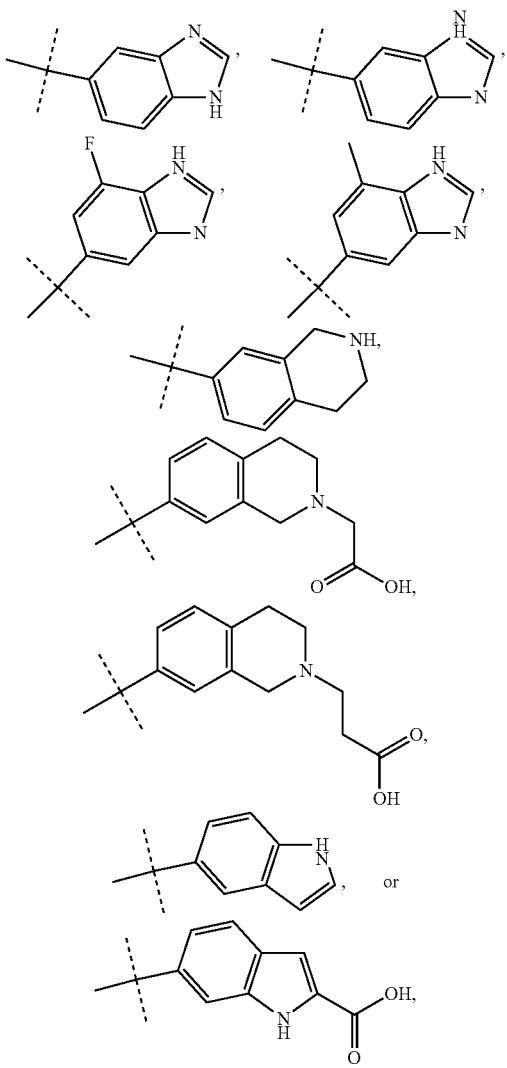

Y denotes

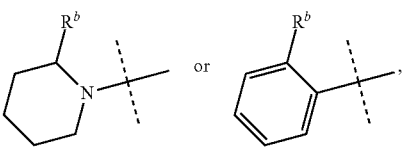

$R^a$ is —$CH_2OCH_3$, —$CH_2$—$N(CH_3)_2$ or $NHSO_2CH_3$,
$R^b$ is —$CH_3$ or —$CH_2$—$CH_3$,
X denotes —CH—,
  and tautomers, salts and stereoisomers thereof.

2. The compound of Formula (I) according to claim 1, wherein $R^a$ is —CH$_2$OCH$_3$.

3. The compound according to claim 1, wherein $R^a$ is —CH$_2$—N(CH$_3$)$_2$.

4. The compound of Formula (I) according to claim 1, wherein $R^a$ is —NHSO$_2$CH$_3$.

5. The compound of Formula (I) according to claim 1, wherein $R^b$ is —CH$_3$.

6. The compound of Formula (I) according to claim 1 wherein $R^b$ is —CH$_2$—CH$_3$.

7. The compound of Formula (I) according to claim 1, selected from the following group:

| compound Nb | Structure |
|---|---|
| 4 | 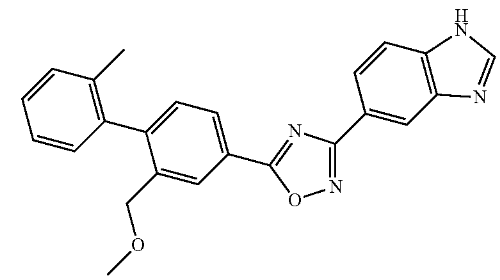 [SMILES: COCc1cc(-c2nc(-c3ccc4[nH]cnc4c3)no2)ccc1-c1ccccc1C] |
| 5 | 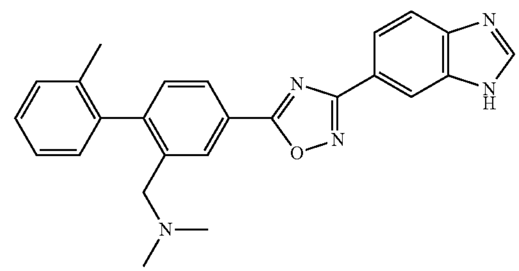 [SMILES: Cc1ccccc1-c1ccc(-c2nc(-c3ccc4nc[nH]c4c3)no2)cc1CN(C)C] |
| 6 | 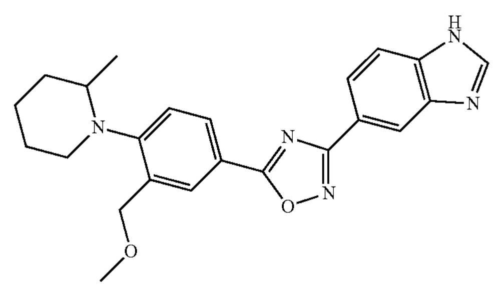 [SMILES: COCc1cc(-c2nc(-c3ccc4[nH]cnc4c3)no2)ccc1N1CCCCC1C] |
| 9 | 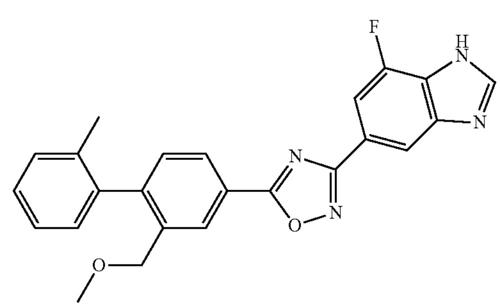 [SMILES: COCc1cc(-c2nc(-c3cc(F)c4[nH]cnc4c3)no2)ccc1-c1ccccc1C] |
| 11 | 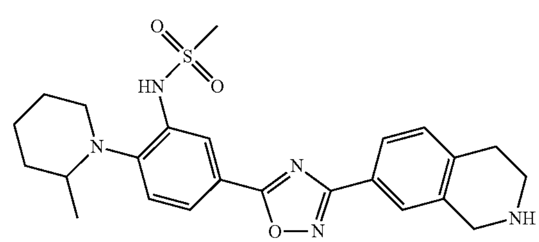 [SMILES: CC1CCCCN1c1ccc(-c2nc(-c3ccc4c(c3)CNCC4)no2)cc1NS(C)(=O)=O] |

-continued
| compound Nb | Structure |
|---|---|
| 15 | 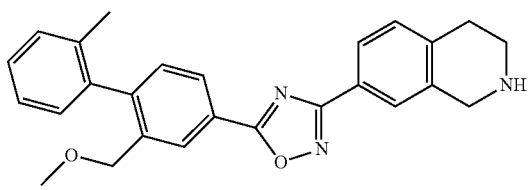 [SMILES: COCc1cc(-c2nc(-c3ccc4c(c3)CNCC4)no2)ccc1-c1ccccc1C] |
| 16 | 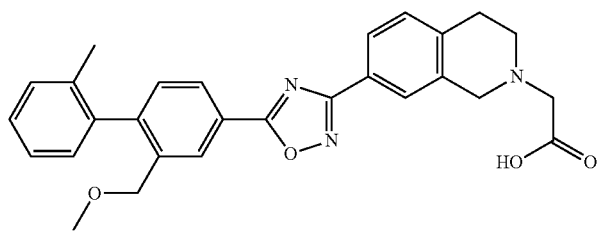 |
| 22 | 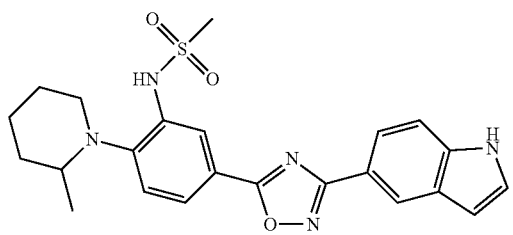 [SMILES: CC1CCCCN1c1ccc(-c2nc(-c3ccc4[nH]ccc4c3)no2)cc1NS(C)(=O)=O] |
| 26 | 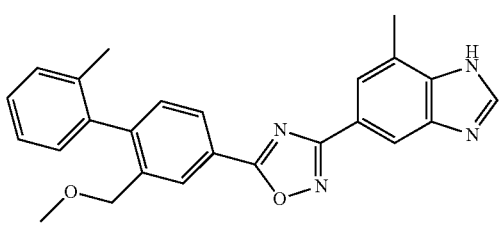 [SMILES: COCc1cc(-c2nc(-c3cc(C)c4[nH]cnc4c3)no2)ccc1-c1ccccc1C] |
| 27 | 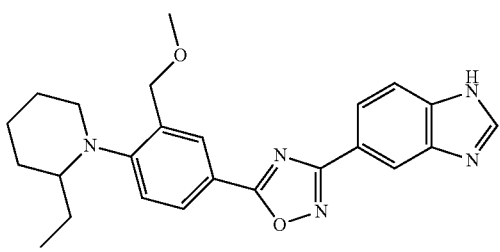 [SMILES: CCC1CCCCN1c1ccc(-c2nc(-c3ccc4[nH]cnc4c3)no2)cc1COC] |
| 30 | 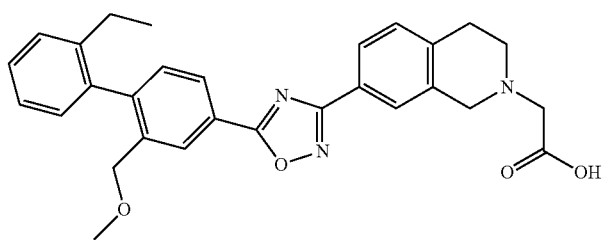 [SMILES: CCc1ccccc1-c1ccc(-c2nc(-c3ccc4c(c3)CN(CC(=O)O)CC4)no2)cc1COC] |

-continued

| compound Nb | Structure |
|---|---|
| 31 | 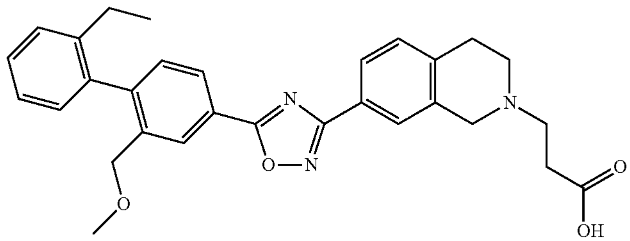 [SMILES: CCc1ccccc1-c1ccc(-c2nc(-c3ccc4c(c3)CN(CCC(=O)O)CC4)no2)cc1COC] |
| 32 | 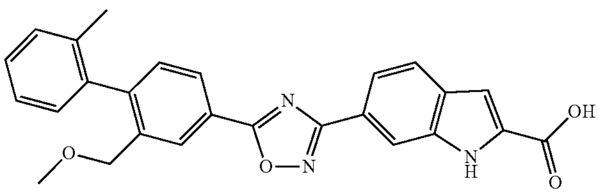 [SMILES: COCc1cc(-c2nc(-c3ccc4cc(C(=O)O)[nH]c4c3)no2)ccc1-c1ccccc1C] |
| 33 | 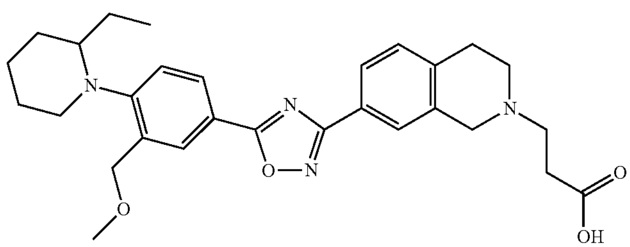 [SMILES: CCC1CCCCN1c1ccc(-c2nc(-c3ccc4c(c3)CN(CCC(=O)O)CC4)no2)cc1COC] |
| 34 | 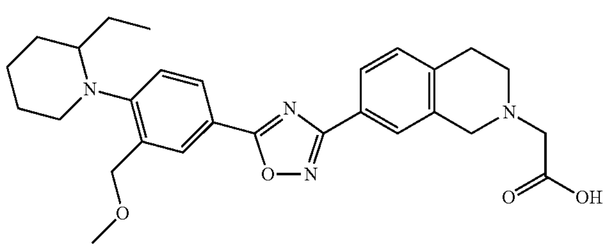 [SMILES: CCC1CCCCN1c1ccc(-c2nc(-c3ccc4c(c3)CN(CC(=O)O)CC4)no2)cc1COC] |
| 35 | 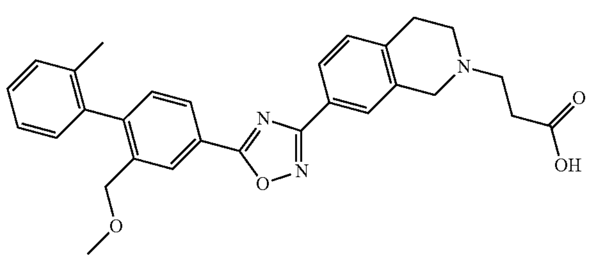 |
| 40 | | and tautomers, salts and stereoisomers thereof.

8. A pharmaceutical composition comprising at least one compound according to claim 1.

9. A process for the preparation of compounds of formula (I) according to claim 1, comprising:

i) addition of the aryl amidoxime (II) with compounds of Formula (III)

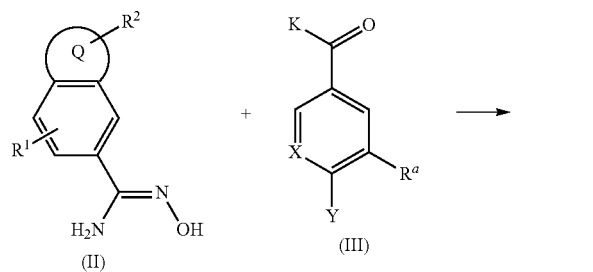

and ii) cyclisation of compounds of Formula (IV) to provide compounds of Formula (I)

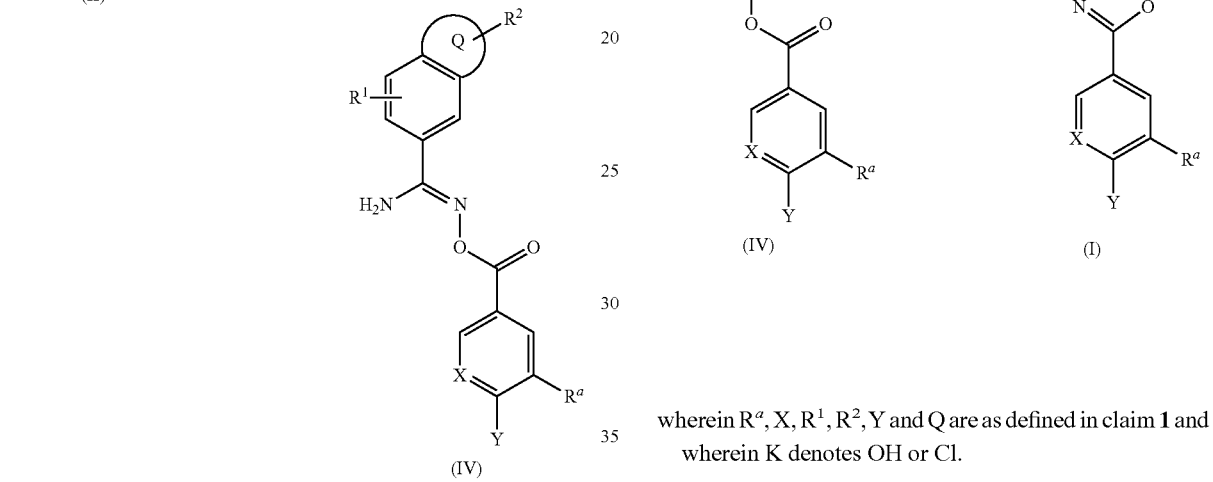

wherein $R^a$, X, $R^1$, $R^2$, Y and Q are as defined in claim 1 and wherein K denotes OH or Cl.

* * * * *

UNITED STATES PATENT AND TRADEMARK OFFICE
CERTIFICATE OF CORRECTION

PATENT NO.        : 8,741,923 B2
APPLICATION NO.   : 13/130411
DATED             : June 3, 2014
INVENTOR(S)       : Mathilde Muzerelle et al.

It is certified that error appears in the above-identified patent and that said Letters Patent is hereby corrected as shown below:

In the Specification

Column 3,
Line 22, "mycophenolic add;" should read --mycophenolic acid;--.

Column 23,
Lines 57-58, "Benz-2,1,3-oxadiazolyl" should read --benz-2,1,3-oxadiazolyl--.

Column 24,
Line 59, "–NIISO$_2$CH$_3$," should read -- –NHSO$_2$CH$_3$,--.

Column 25,
Line 3, "by COOR$^S$," should read --by COOR$^3$,--.

Column 29,
Compound Nb 7,

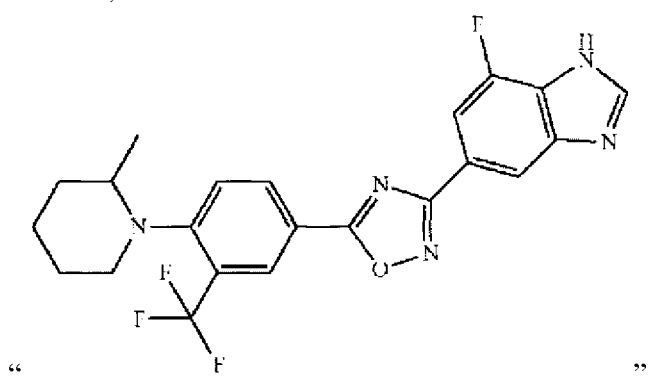

should read

Signed and Sealed this
Eleventh Day of August, 2015

Michelle K. Lee
*Director of the United States Patent and Trademark Office*

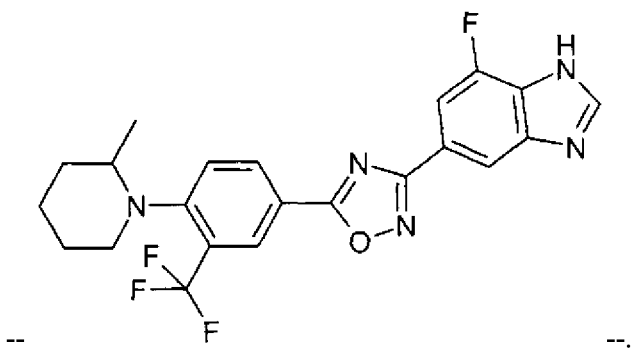
--                                    --.
Column 35,
Compound Nb 26,
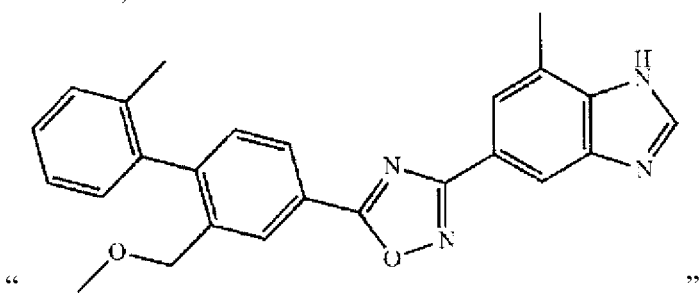
"                                                              "
should read
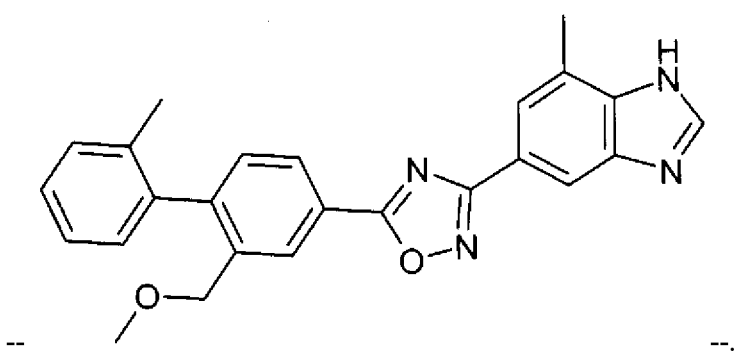
--                                    --.
Column 37,
Compound Nb 31,
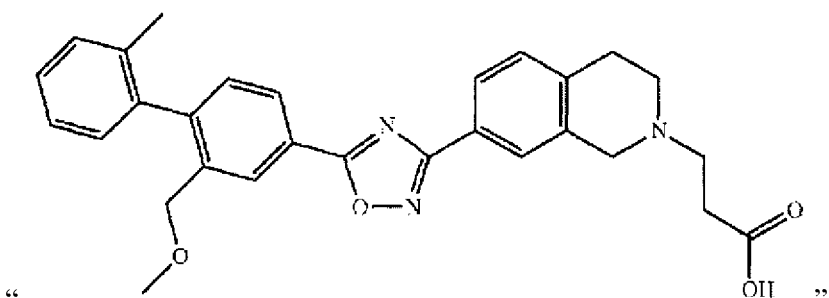
"                                                              "
should read

CERTIFICATE OF CORRECTION (continued)
U.S. Pat. No. 8,741,923 B2

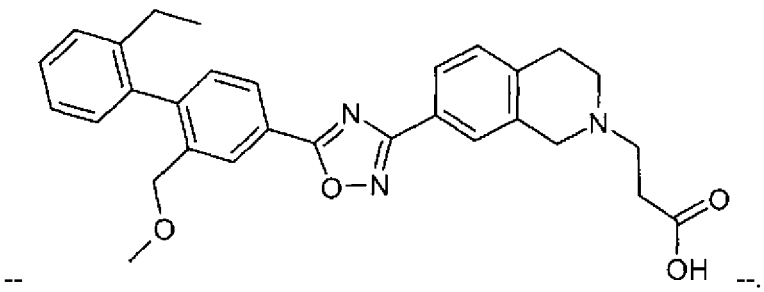

-- --.

Column 47,
Line 60, "of a compounds" should read --of a compound--.

Columns 47-48,
Lines 67-1, "subject a compounds" should read --subject a compound--.

Column 48,
Line 30, "alopecia greata," should read --alopecia areata,--.

Column 49,
Line 66, "HPLC/MS:" should read --UPLC/MS:--.
Line 67, "HPLC BEH" should read --UPLC BEH--.

Column 50,
Line 54, "1H" should read --$^1$H--.

Column 54,
Line 9, "(M+1-1)$^+$." should read --(M+H)$^+$.--.

Column 63,
Line 9, "obtain in step 2" should read --obtained in step 2--.

Column 64,
Line 7, "2 hours The" should read --2 hours. The--.

Column 66,
Lines 32-33, "to obtain get the title compound" should read --to give the title compound--.

Column 76,
Line 54, "mmol) The" should read --mmol). The--.
Line 57, "filtered trough" should read --filtered through--.

Column 81,
Line 42, "97.3%). CL Step 2:" should read
--97.3%)
    Step 2:--.

CERTIFICATE OF CORRECTION (continued)
U.S. Pat. No. 8,741,923 B2

Column 87,
Lines 6-9,

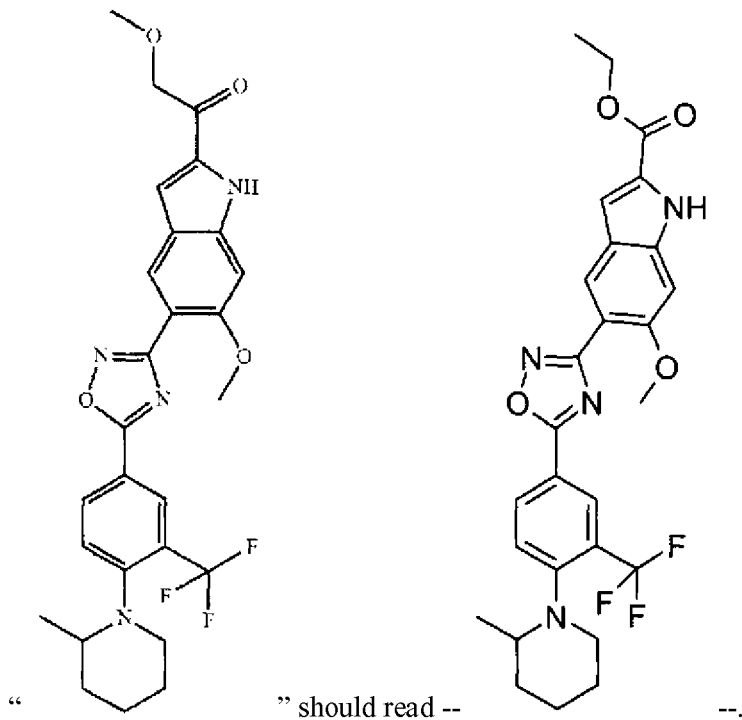

" should read -- --.

Column 88,
Lines 57-58, "in a of DCM/n-pentane" should read --in a DCM/n-pentane--.

Column 89,
Line 39, "(M-H)." should read --(M-H)⁻.--.

Column 100,
Lines 26-48,

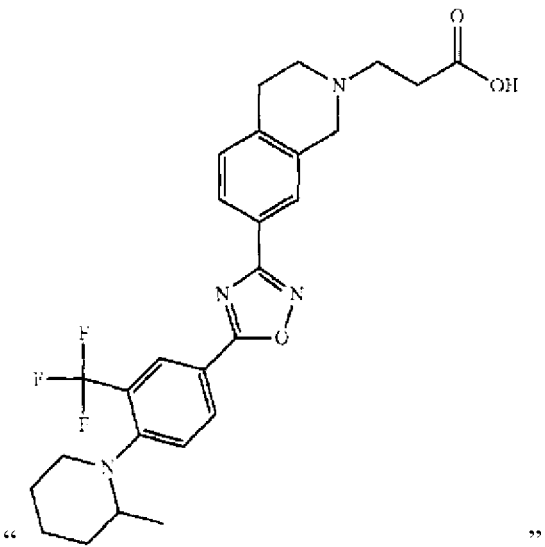

should read

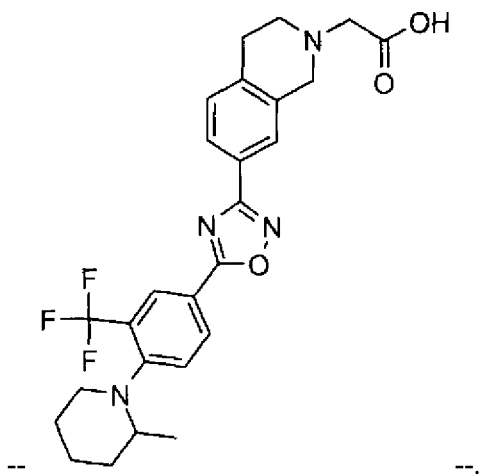
Column 103,
Lines 13-14, "25 μM or 10 μM" should read --25 pM or 10 pM--.
In the Claims
Column 122,
Lines 3-4, "according to claim wherein" should read --according to claim 1, wherein--.